US011390865B2

(12) United States Patent
Fukuda et al.

(10) Patent No.: US 11,390,865 B2
(45) Date of Patent: Jul. 19, 2022

(54) METHOD FOR INTRODUCING SITE-DIRECTED RNA MUTATION, TARGET EDITING GUIDE RNA USED IN THE METHOD AND TARGET RNA-TARGET EDITING GUIDE RNA COMPLEX

(71) Applicant: FUKUOKA UNIVERSITY, Fukuoka (JP)

(72) Inventors: Masatora Fukuda, Fukuoka (JP); Hiromitsu Umeno, Fukuoka (JP)

(73) Assignee: FUKUOKA UNIVERSITY, Fukuoka (JP)

( * ) Notice: Subject to any disclaimer, the term of this patent is extended or adjusted under 35 U.S.C. 154(b) by 1032 days.

(21) Appl. No.: 15/744,771

(22) PCT Filed: Jul. 14, 2016

(86) PCT No.: PCT/JP2016/070915
§ 371 (c)(1),
(2) Date: Jan. 13, 2018

(87) PCT Pub. No.: WO2017/010556
PCT Pub. Date: Jan. 19, 2017

(65) Prior Publication Data
US 2018/0208924 A1    Jul. 26, 2018

(30) Foreign Application Priority Data

Jul. 14, 2015  (JP) .............................. JP2015-140894

(51) Int. Cl.
*C12N 15/10*   (2006.01)
*C12N 9/78*    (2006.01)
*C12N 15/11*   (2006.01)

(52) U.S. Cl.
CPC .......... *C12N 15/1024* (2013.01); *C12N 9/78* (2013.01); *C12N 15/102* (2013.01); *C12N 15/111* (2013.01); *C12N 2310/141* (2013.01); *C12Y 305/04004* (2013.01)

(58) Field of Classification Search
None
See application file for complete search history.

(56) References Cited

U.S. PATENT DOCUMENTS 9,650,627 B1 *   5/2017   Rosenthal ............ C12N 15/102

FOREIGN PATENT DOCUMENTS

DE   102015012522 B3   6/2016
WO   2016/097212 A1    6/2016

OTHER PUBLICATIONS

Heidenreich M, Zhang F. Applications of CRISPR-Cas systems in neuroscience. Nat Rev Neurosci 17, 36-44 (2016).
Kim YG, Cha J, Chandrasegaran S. Hybrid restriction enzymes: zinc finger fusions to Fok I cleavage domain. Proc Nat Acad Sci U S A 93, 1156-1160 (1996).
Porteus MH, Carroll D. Gene targeting using zinc finger nucleases. Nat Biotechnol 23, 967-973 (2005).
Zhang F, Cong L, Lodato S, Kosuri S, Church GM, Arlotta P. Efficient construction of sequence-specific TAL effectors for modulating mammalian transcription. Nat Biotechnol 29, 149-153 (2011).
Mali P, et al. RNA-guided human genome engineering via Cas9. Science 339, 823-826 (2013).
Araki M, Ishii T. Providing Appropriate Risk Information on Genome Editing for Patients Trends Biotechnol 34, 86-90 (2016).
Elbashir SM, Harborth J, Lendeckel W, Yalcin A, Weber K, Tuschl T. Duplexes of 21-nucleotide RNAs mediate RNA nterference in cultured mammalian cells. Nature 411, 494-498 (2001).
Ambros V. The functions of animal microRNAs. Nature 431, 350-355 (2004).
Carthew RW, Sontheimer EJ. Origins and Mechanisms of miRNAs and siRNAs. Cell 136, 642-655 (2009).
Lam JK, Chow MY, Zhang Y, Leung SW. siRNA Versus miRNA as Therapeutics for Gene Silencing. Mol Ther Nucleic Acids 4, e252 (2015).
Cho, S. W.; Kim, S.; Kim, J. M.; Kim, J. S., Targeted genome engineering in human cells with the Cas9 RNA-guided andonuclease. Nat Biotechnol 2013, 31 (3), 230-2.
Mali, P.; Yang, L.; Esvelt, K. M.; Aach, J.; Guell, M.; DiCarlo, J. E.; Norville, J. E.; Church, G. MRNA-guided human genome engineering via Cas9. Science 2013, 339(6121), 823-6.
Bass BL. RNA editing by adenosine deaminases that act on RNA. Annu Rev Biochem 71, 817-846 (2002).
Nishikura K. Functions and regulation of RNA editing by ADAR deaminases. Annu Rev Biochem 79, 321-349 (2010).
Wulff BE, Nishikura K. Substitutional A-to-1 RNA editing. WIREs RNA 1, 90-101 (2010).
Peng, Z.; Cheng, Y.; Tan, B. C.; Kang, L.; Tian, Z.; Zhu, Y.; Zhang, W.; Liang, Y.; Hu, X.; Tan, X.; Guo, J.; Dong, Z. Bao, L.; Wang, J., Comprehensive analysis of RNA-Seq data reveals extensive RNA editing in a human transcriptome. Nat Biotechnol 2012, 30 (3), 253-60.
Ganot P, Bortolin ML, Kiss T. Site-specific pseudouridine formation in preribosomal RNA is guided by small nucleolar RNAs Cell 89, 799-809 (1997).
Cavaille J, Bachellerie JP. SnoRNA-guided ribose methylation of rRNA: structural features of the guide RNA duplex nfluencing the extent of the reaction. Nucleic Acids Res 26, 1576-1587 (1998).
Weinstein LB, Steitz JA. Guided tours: from precursor snoRNA to functional snoRNP. Curr Opin Cell Biol 11, 378-384 (1999).

(Continued)

*Primary Examiner* — James D Schultz
(74) *Attorney, Agent, or Firm* — Hunton Andrews Kurth LLP

(57) ABSTRACT

A method for inducing a site-directed RNA mutation is provided. The method includes repairing an RNA mutation by converting target adenosine, which is located at a target editing site of a target RNA, into inosine. The method for inducing a site-directed RNA mutation involves reacting the target RNA having a target adenosine with a target editing guide, which has been constructed so as to form a complementary strand with target RNA, to form a double-stranded complex, and converting the target adenosine to inosine by causing ADAR to act on the double-stranded complex, inducing A-to-I editing capability. The converted inosine is further translated into guanosine.

3 Claims, 51 Drawing Sheets

Specification includes a Sequence Listing.

(56) References Cited

OTHER PUBLICATIONS

Cavaille J, Nicoloso M, Bachellerie JP. Targeted ribose methylation of RNA in vivo directed by tailored antisense RNA guides. Nature 383, 732-735 (1996).
Zhao X, Yu YT. Targeted pre-mRNA modification for gene silencing and regulation. Nat Methods 5, 95-100 (2008).
Karijolich J, Yu YT. Converting nonsense codons into sense codons by targeted pseudouridylation. Nature 474, 395-398 (2011).
Stafforst T, Schneider MF. An RNA-deaminase conjugate selectively repairs point mutations. Angew Chern Int Ed Engl 51, 11166-11169 (2012).
Schneider MF, Wettengel J, Hoffmann PC, Stafforst T. Optimal guideRNAs for re-directing deaminase activity of hADAR1 and hADAR2 in trans Nucleic Acids Res 42, e87 (2014).
Vogel P, Schneider MF, Wettengel J, Stafforst T. Improving site-directed RNA editing in vitro and in cell culture by chemical modification of the guideRNA. Angew Chern Int Ed Engl 53, 6267-6271 (2014).
Montiel-Gonzalez MF, Vallecillo-Viejo I, Yudowski GA, Rosenthal JJ. Correction of mutations within the cystic fibrosis transmembrane conductance regulator by site-directed RNA editing. Proc Natl Acad Sci U S A 110, 18285-18290 (2013).
Vollmar W, et al. RNA editing (R/G site) and flip-flop splicing of the AMPA receptor subunit GluR2 in nervous tissue of epilepsy patients Neurobiol Dis 15, 371-379 (2004).
Lomeli, H.; Mosbacher, J.; Melcher, T.; Hoger, T.; Geiger, J. R.; Kuner, T.; Monyer, H.; Higuchi, M.; Bach, A.; Seeburg, P. H., Control of kinetic properties of AMPA receptor channels by nuclear RNA editing. Science 1994, 266(5191), 1709-13.
Pokharel, S.; Beal, P. A., High-throughput screening for functional adenosine to inosine RNA editing systems. ACS Chem Biol 2006, 1 (12), 761-5.
Nurpeisov V, Hurwitz SJ, Sharma PL. Fluorescent dye terminator sequencing methods for quantitative determination of replication fitness of human immunodeficiency virus type 1 containing the codon 74 and 184 mutations in reverse transcriptase. J Clin Microbiol 41, 3306-3311 (2003).
Pokharel S, Beal PA. High-throughput screening for functional adenosine to inosine RNA editing systems. ACS Chem Biol 1, 761-765 (2006).
Gommans WM, McCane J, Nacarelli GS, Maas S. A mammalian reporter system for fast and quantitative detection of Intracellular A-to-I RNA editing levels. Anal Biochem 399, 230-236 (2010).
Fukuda M, Kurihara K, Yamaguchi S, Oyama Y, Deshimaru M. Improved design of hammerhead ribozyme for selective digestion of target RNA through recognition of site-specific adenosine-to-inosine RNA editing. RNA 20, 392-405 (2014).
Hanswillemenke A, Kuzdere T, Vogel P, Jekely G, Stafforst T. Site-Directed RNA Editing in Vivo Can Be Triggered by the Light-Driven Assembly of an Artificial Riboprotein. J Am Chem Soc 137, 15875-15881 (2015).
Stefl R, et al. The solution structure of the ADAR2 dsRBMRNA complex reveals a sequence-specific readout of the minor groove. Cell 143, 225-237 (2010).
Dabiri GA, Lai F, Drakas RA, Nishikura K. Editing of the GLuR-B ion channel RNA in vitro by recombinant doublestranded RNA adenosine deaminase. Embo J 15, 34-45 (1996).
Yeo J, Goodman RA, Schirle NT, David SS, Beal PA. RNA editing changes the lesion specificity for the DNA repair anzyme NEIL1. Proc Natl Acad Sci U S A 107, 20715-20719 (2010).
Keegan LP, Leroy A, Sproul D, O'Connell MA. Adenosine deaminases acting on RNA (ADARs): RNA-editing enzymes. Genome Biol 5, 209 (2004).
M. F. Schneider et al., "Optimal guideRNAs for re-directing deaminase activity of hADARI and hADAR2 in trans", Nucleic Acids Research, vol. 42, No. 10, Apr. 17, 2014, 9 pages.
M. F. Schneider et al., Supporting Infromation, "Optimal guideRNAs for re-directing deaminase activity of hADAR1 and hADAR2 in trans", Nucleic Acids Research, vol. 42, No. 10, Apr. 17, 2014, 16 pages.
Masatora Fukuda et al.: "Construction of a guide-RNA for site-directed RNA mutagenesis utilising intracellular A-to-I RNA editing", Scientific Reports, vol. 7, No. 1, Feb. 2, 2017, article No. 41478, 14 pages.
Fukuda et al., Supplementary Table 1. Nucleotide sequences of DNA oligonucleotides and primers, Scientific Reports, Feb. 2, 2017. 4 pages.
Masatora Fukuda et al., Supplementary Information, "Construction of a guide-RNA for site-directed RNA mutagenesis utilising intracellular A-to-I RNA editing", Scientific Reports, vol. 7, No. 1, Feb. 2, 2017, article No. 11478, 50 pages.
European Patent Office, Extended European Search Report issued in Application No. 1624536.3 dated Jan. 7, 2019, 8 pages.

* cited by examiner (SEQ ID NO: 99)

(SEQ ID NO: 99)

Fig. 21
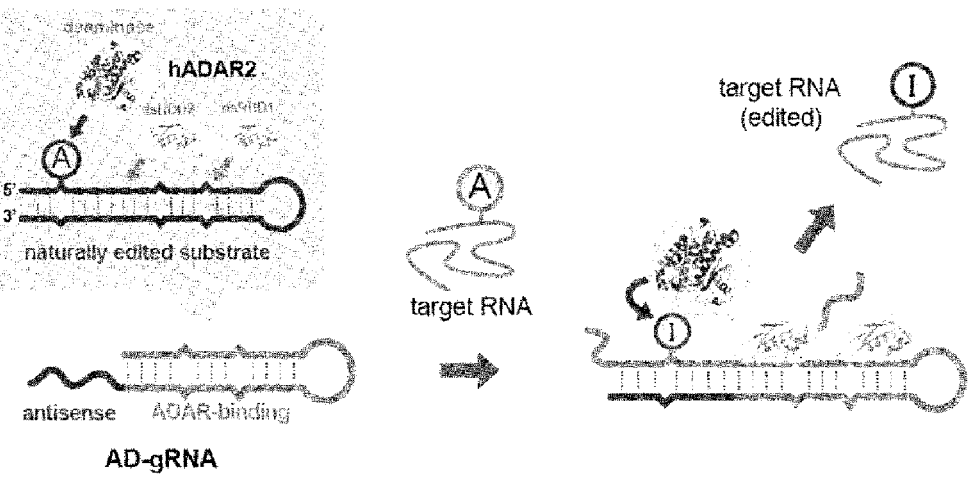
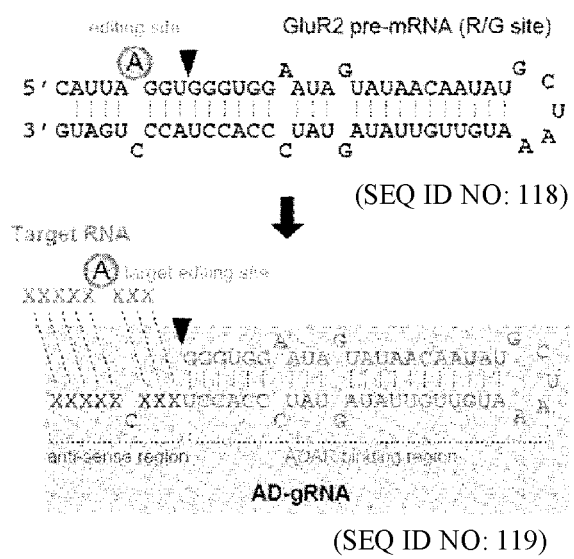
(SEQ ID NO: 118)
(SEQ ID NO: 119)
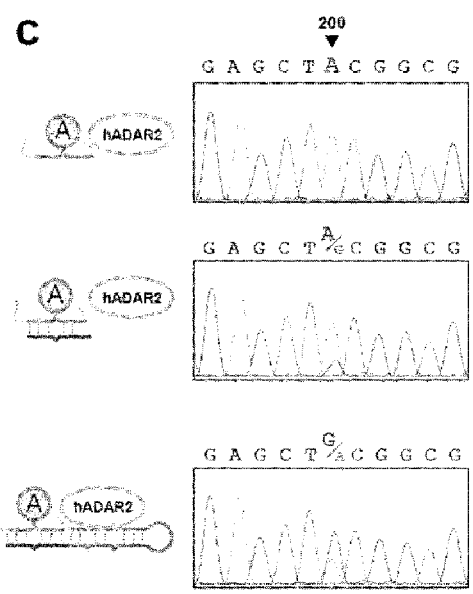

Fig. 22A
a
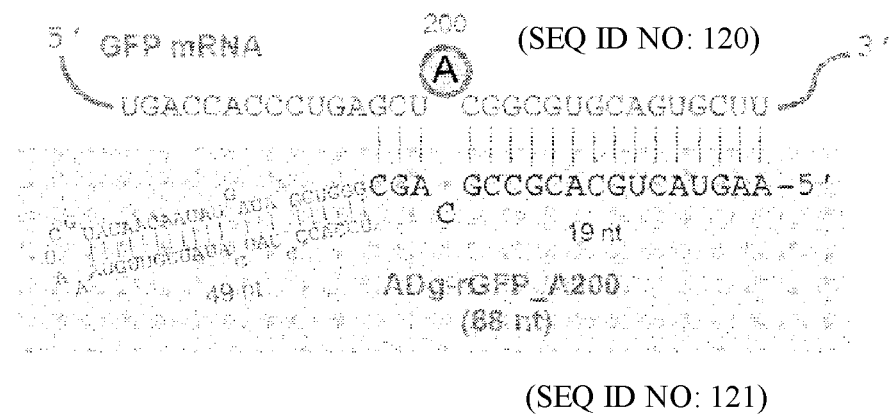
(SEQ ID NO: 120)
(SEQ ID NO: 121)
b
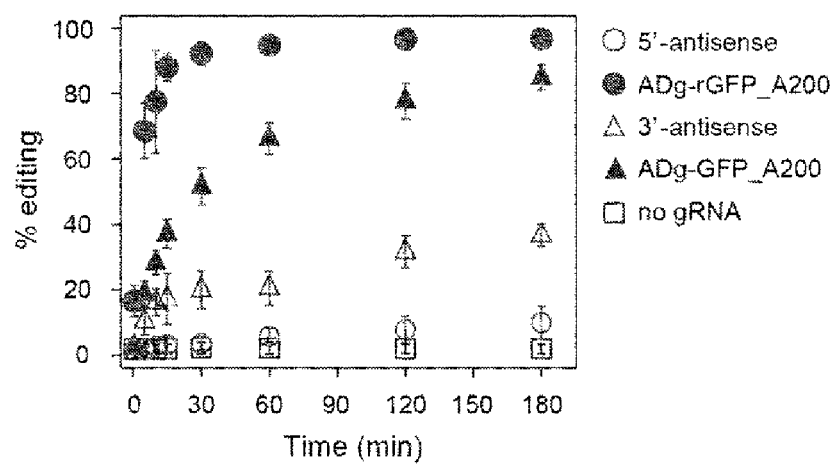

8% Native PAGE
(EtBr staining)

Fig. 24
a
hairpin substrate
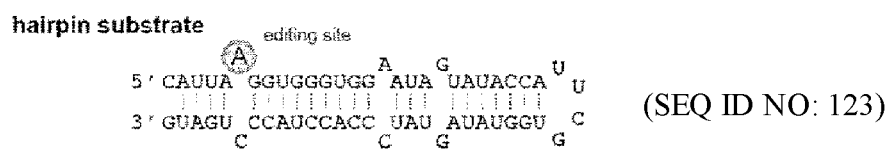
(SEQ ID NO: 123)
b
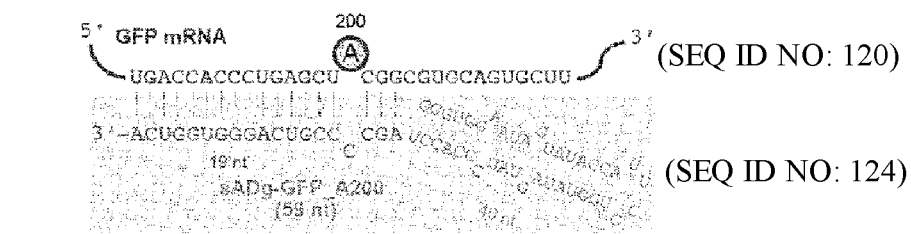
(SEQ ID NO: 120)
(SEQ ID NO: 124)
(SEQ ID NO: 120)
(SEQ ID NO: 125)
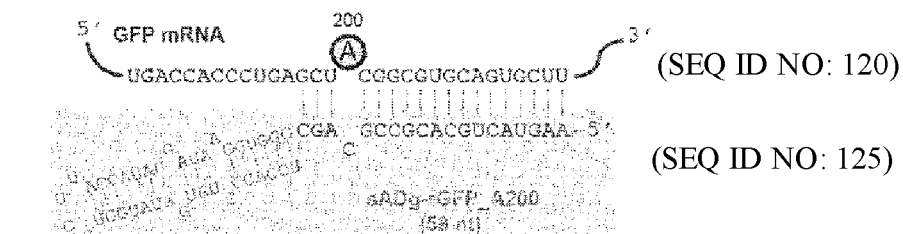
c
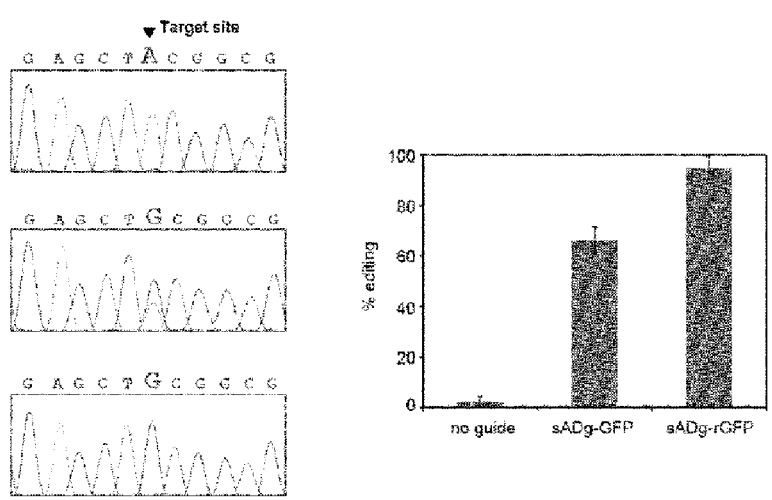

Fig. 25
a
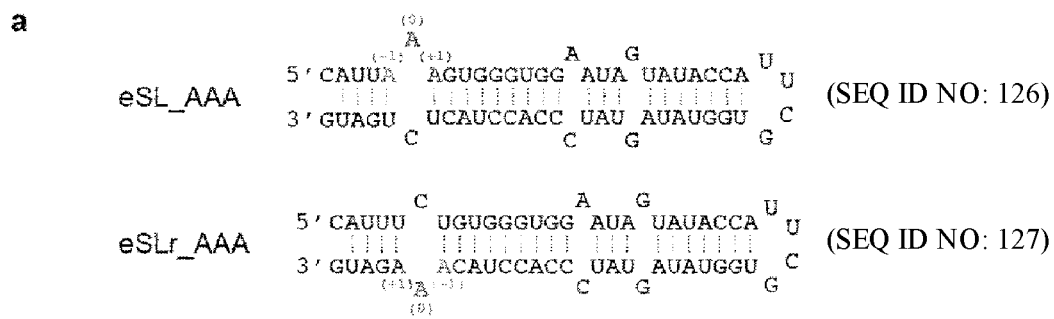
eSL_AAA (SEQ ID NO: 126)
eSLr_AAA (SEQ ID NO: 127)
b
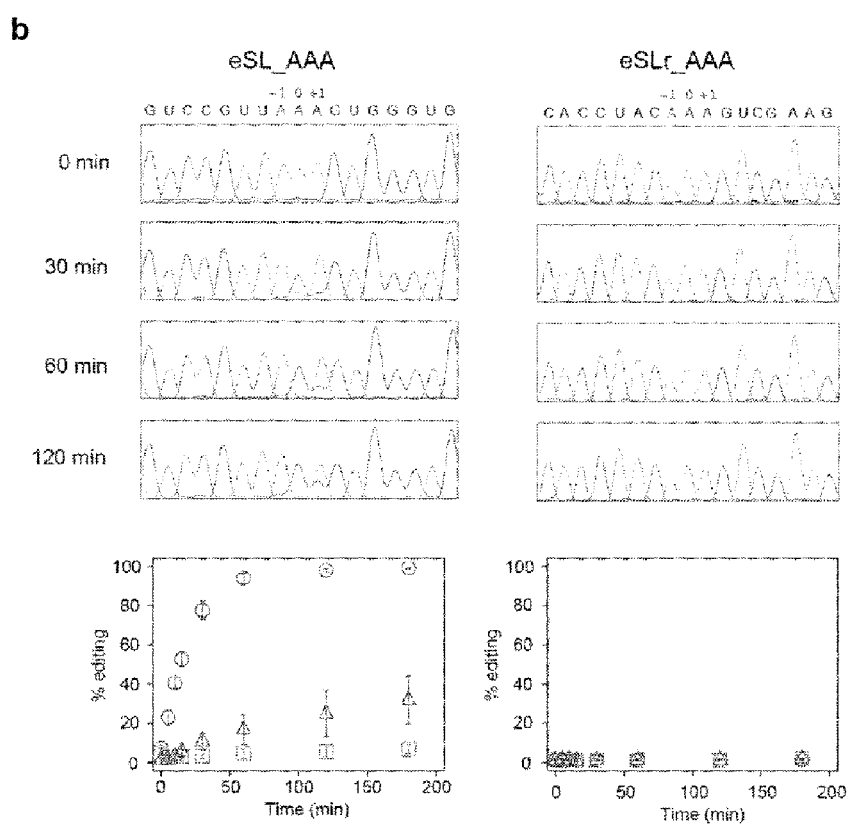

Fig. 26
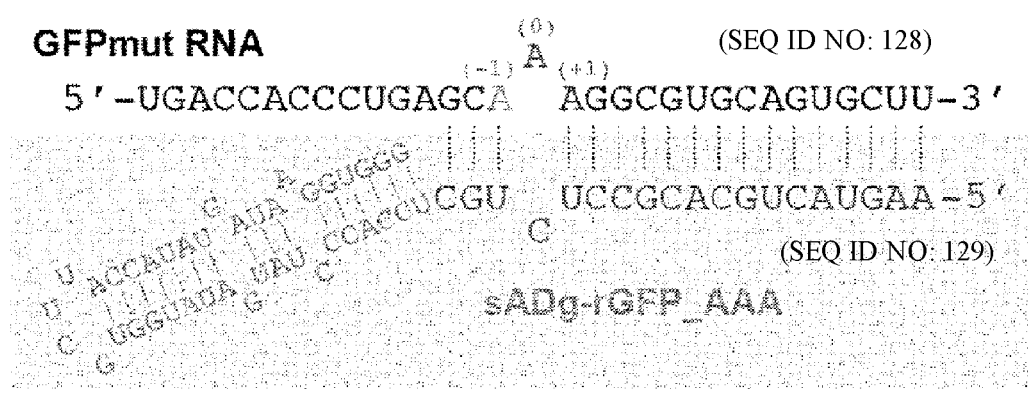
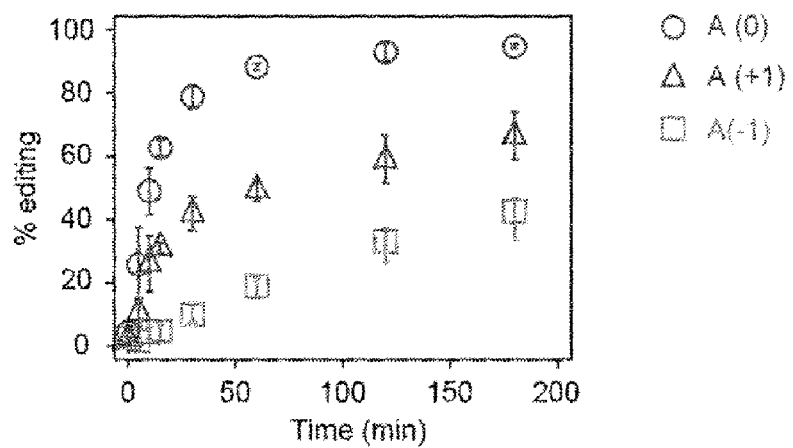

Fig. 27
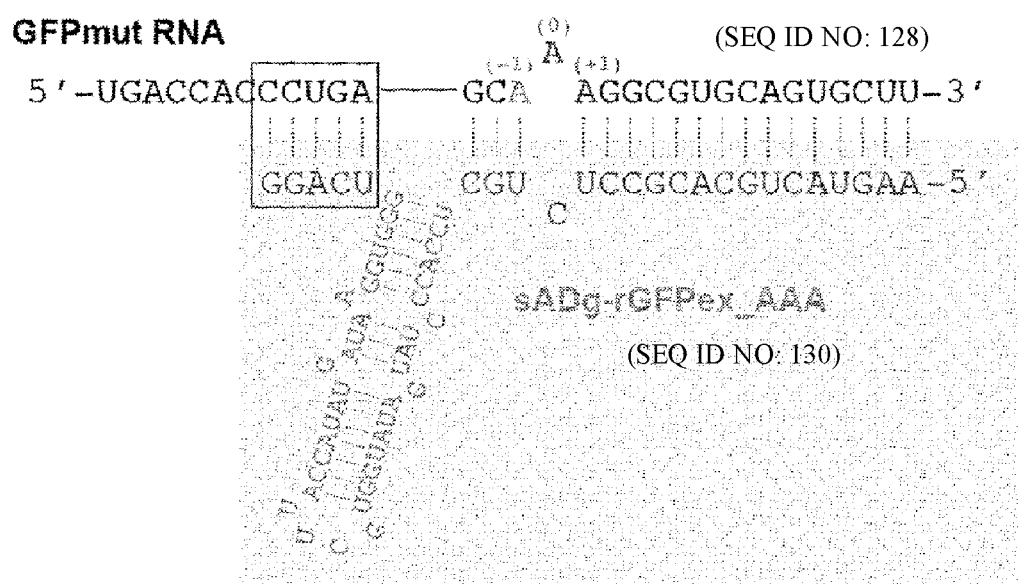
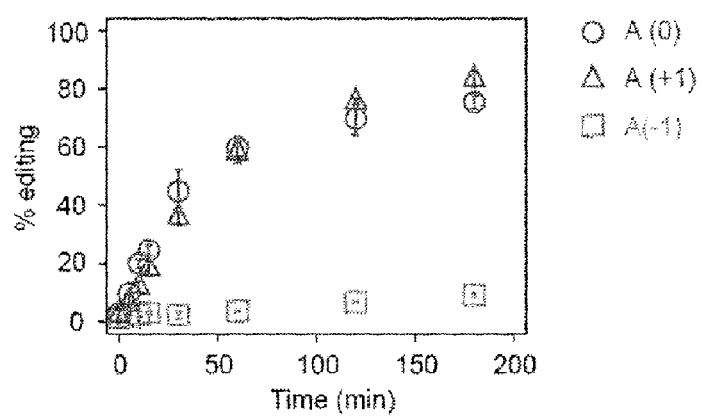

Fig. 35
a
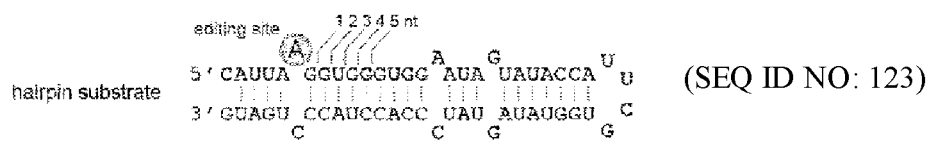
(SEQ ID NO: 123)
b
c
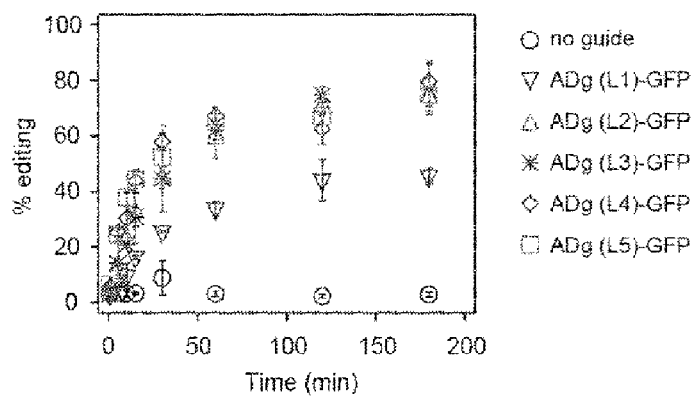

Fig. 61
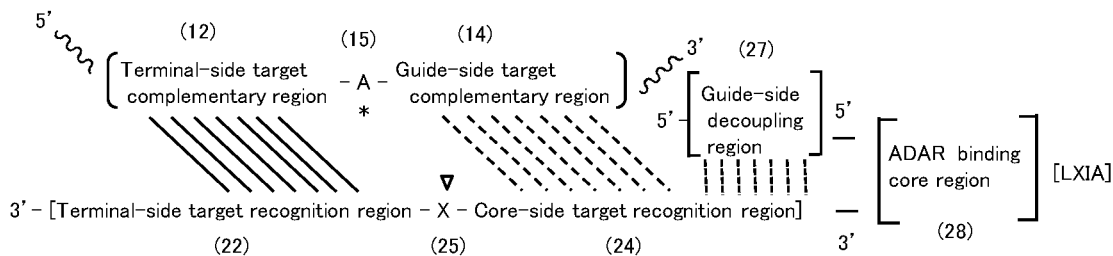
Fig. 62
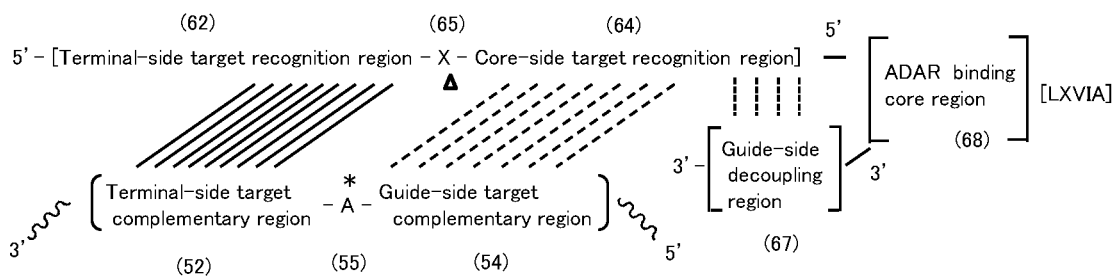
Fig. 63
5'-Edited target RNA
5' ∿∿ [Terminal-side target complementary region – *I – Guide-side target complementary region] ∿∿ 3'     [LXIIA]
           (12)                              (16)                     (14)
Fig. 64
3'-Edited target RNA
3' ∿∿ [Terminal-side target complementary region – *I – Guide-side target complementary region] ∿∿ 5'     [LXVIIA]
           (52)                              (56)                     (54)
Fig. 65
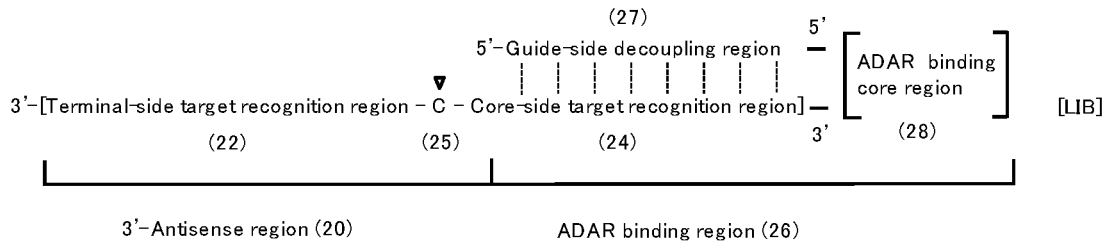
Fig. 66
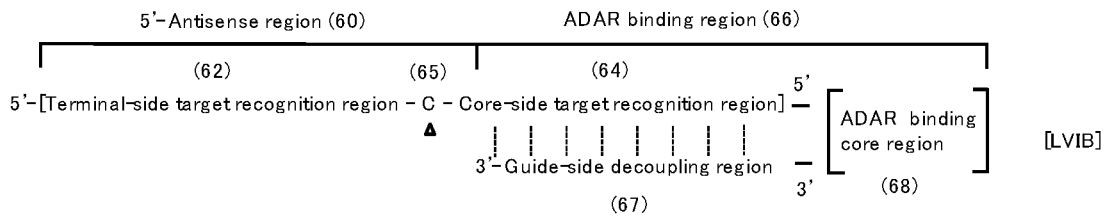

Fig. 67

5' - Target RNA - 3' - Editing guide RNA Complex

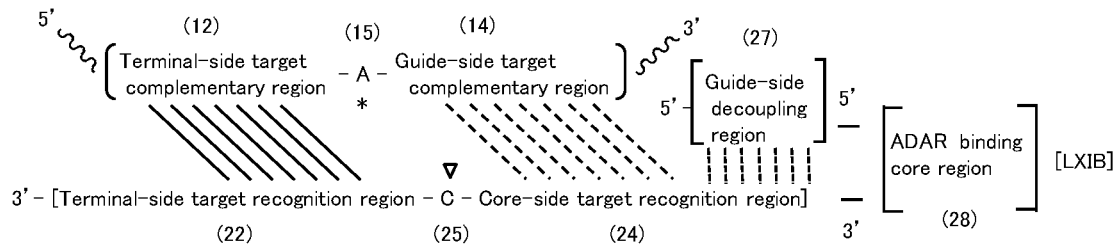

Fig. 68

3' - Target RNA - 5' - Editing guide RNA Complex

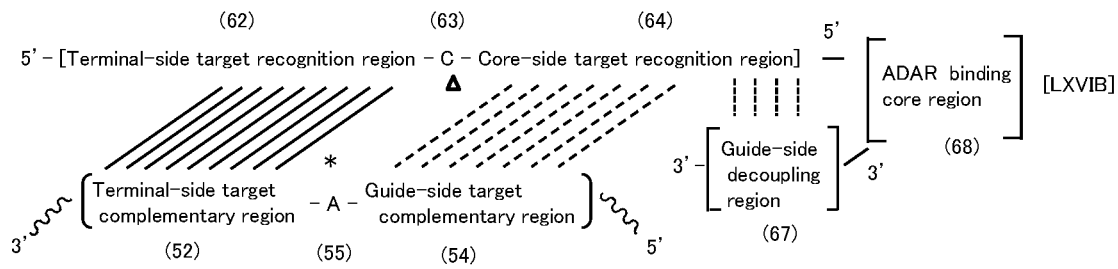

Fig. 69

5'-Edited target RNA

5' ∿∿ [Terminal-side target complementary region - I - Guide-side target complementary region] ∿∿ 3'  [LXIIB]
     (12)                                    (13)                          (14)

Fig. 70

3'-Edited target RNA

3' ∿∿ [Terminal-side target complementary region - I - Guide-side target complementary region] ∿∿ 5'  [LXVIIA]
     (52)                                    (56)                          (54)

Fig. 71

5'-Translated target RNA

5'- [Terminal-side target complementary region - G - Guide-side target complementary region] -3'    [LIVA]
     (12)                                    (18)                          (14)

Fig. 72

3'-Translated target RNA

5'- [Terminal-side target complementary region - G - Guide-side target complementary region] -3'    [LIXA]
     (52)                                    (58)                          (54)

Fig. 73

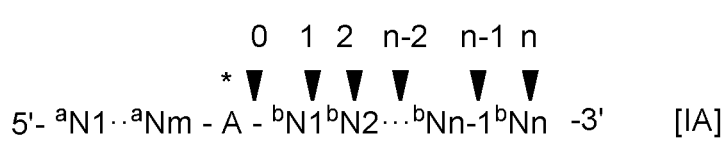

Fig. 74
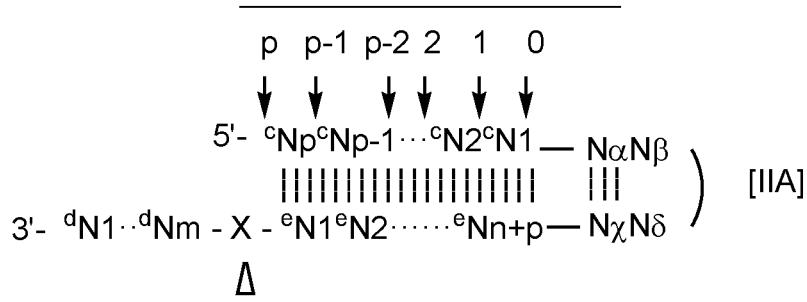
Fig. 75
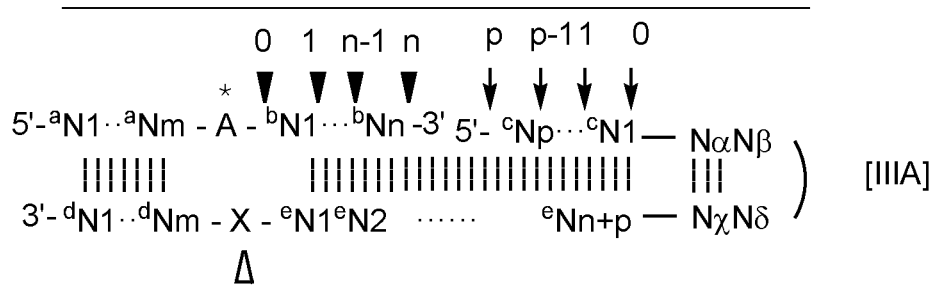
Fig. 76
5'-Edited target RNA
5'- $^aN1\cdots{}^aNm - I - {}^bN1{}^bN2\cdots{}^bNn\text{-}1{}^bNn$ -3'    [IVA]
Fig. 77
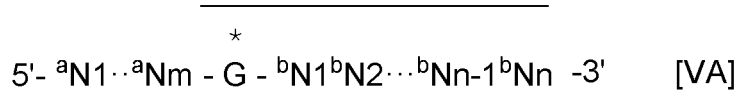
5'- $^aN1\cdots{}^aNm - G - {}^bN1{}^bN2\cdots{}^bNn\text{-}1{}^bNn$ -3'    [VA]
Fig. 78
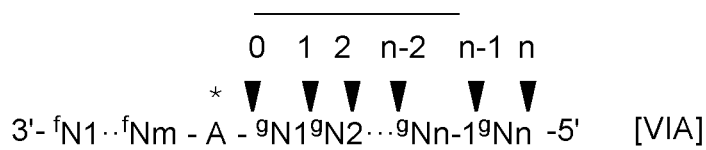
Fig. 79
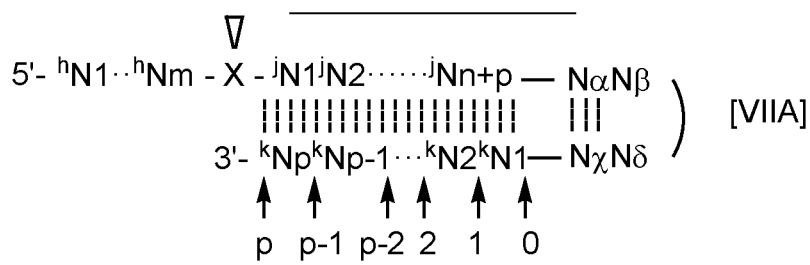

Fig. 80
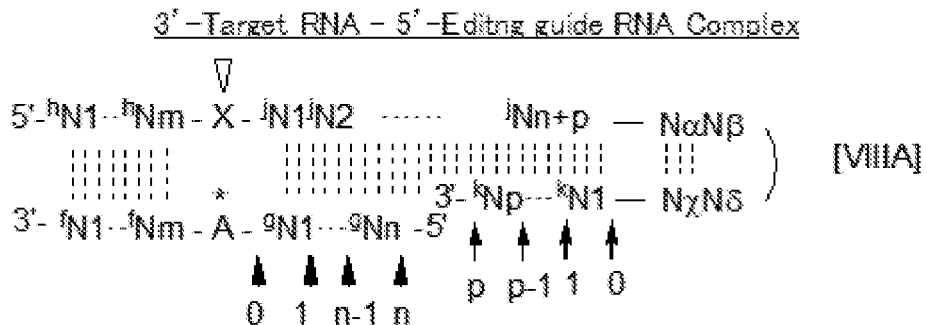
Fig. 81
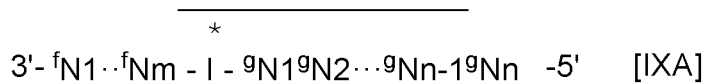
Fig. 82
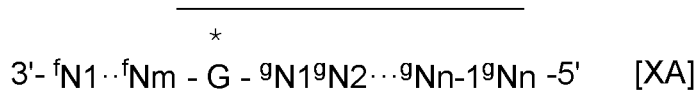
Fig. 83
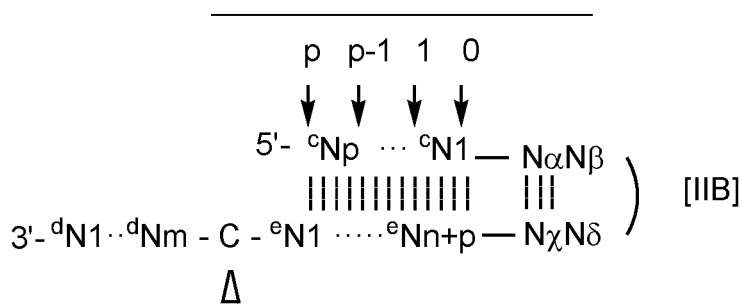
Fig. 84
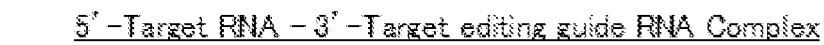
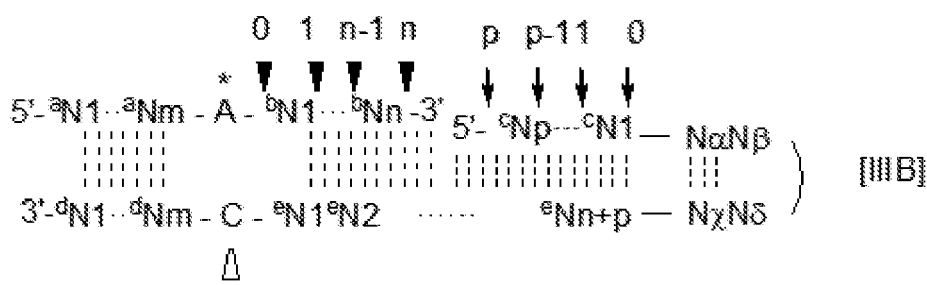

3'-Target RNA - 5'-Editing guide RNA Complex

5'-Target RNA - 3'-Target editing guide RNA Complex

SEQ ID NO: 100

SEQ ID NO: 101

SEQ ID NO: 99

SEQ ID NO: 99

SEQ ID NO: 99

SEQ ID NO: 99

SEQ ID NO: 99

SEQ ID NO: 99

SEQ ID NO: 99

SEQ ID NO: 99

SEQ ID NO: 99

SEQ ID NO: 99

SEQ ID NO: 102

Dividing site

Fig. 125
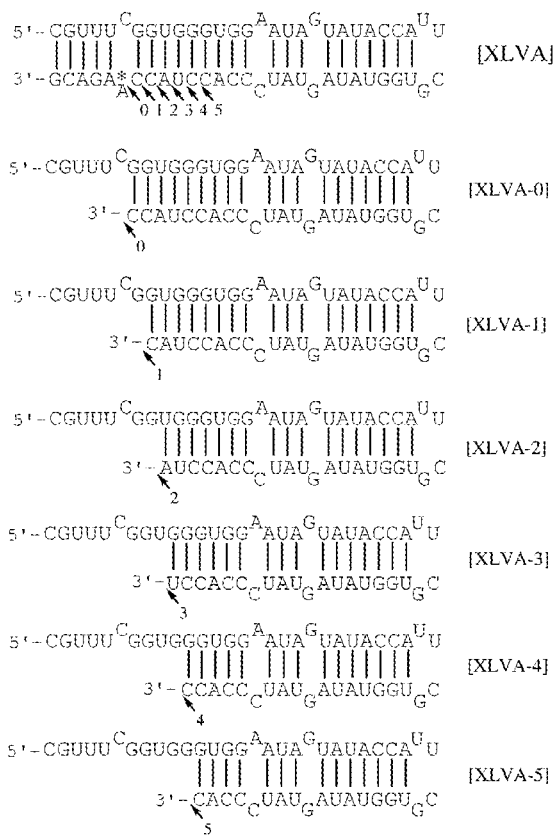
Fig. 126
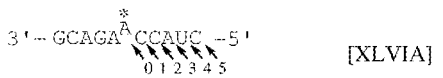
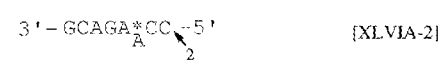
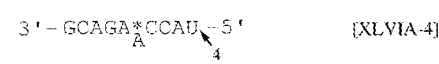
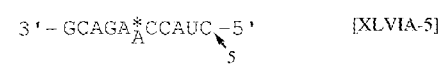

METHOD FOR INTRODUCING SITE-DIRECTED RNA MUTATION, TARGET EDITING GUIDE RNA USED IN THE METHOD AND TARGET RNA-TARGET EDITING GUIDE RNA COMPLEX

CROSS-REFERENCE TO RELATED APPLICATION

This is a national phase application based on the PCT International Patent Application No. PCT/JP2016/070915 filed Jul. 14, 2016, claiming priority to Japanese Patent Application No. 2015-140894 filed Jul. 14, 2015, the entire contents of both of which are incorporated herein by reference.

TECHNICAL FIELD

The present invention relates to a method for introducing a site-directed RNA mutation and a target editing guide RNA to be used in the method, and a target RNA-target editing guide RNA complex. More specifically, the present invention relates to a method for introducing a site-directed RNA mutation including introducing a site-directed RNA mutation by inducing ADAR editing capability at a target editing site of a target RNA having a target base adenosine (A), a target editing guide RNA to be used in the method, and a target RNA-target editing guide RNA complex.

BACKGROUND ART

Genetic engineering technologies for regulating intracellular target-gene functions and/or expression have been widely used not only in basic research on life-related biological phenomena but also in medicinal and therapeutic applications (Non-Patent Literature 1). One purpose of using these methods is to regulate the functions of intracellular proteins involved in biological processes. Recently, a number of advanced genome-editing technologies have enabled target genomic information to be manipulated as desired (Non-Patent Literatures 1, 2, 3, 4, 5). In addition to programmable regulation, the most significant feature of genome alterations is that they can provide a permanent change to the targeted intracellular gene. While this permanent effect can effectively suppress target-protein features, such methods can pose a health hazard if errors occur (Non-Patent Literature 6).

Molecules responsible for biological phenomena are proteins in vivo. Usually, proteins in the living body are translated and synthesized based on information of messenger RNA (mRNA) transcribed from DNA. The thus synthesized proteins play a vital role in various vital activities such as in vivo chemical reactions, structure formation, information transfer, exercise, antibody, and nutrient storage and transport.

In order for intracellular proteins synthesized in this manner to perform normal vital activities, their intracellular proteins must have an accurate structure and exert normal physiological functions. Protein is synthesized by the following steps: genomic information of DNA is self-replicated, its base (nucleotide) sequence is transcribed into mRNA by the action of RNA polymerase, and then translated into amino acid by ribosome. RNA polymerase synthesizes mRNA by polymerizing four nucleosides (A: adenosine, U: uridine, G: guanosine. C: cytidine), which complementarily base pair with DNA base sequence, while moving on the DNA and copying the DNA base sequence using one strand of the DNA duplex (antisense strand: 5'→3') as a template. By this transcription, base pairing complementary to the DNA base sequence of the antisense strand is incorporated, and mRNA is elongated and synthesized as the sense strand (3'→5').

In the past, all the primary structure of protein was believed to be determined by genomic DNA, and RNA was thought to accurately replicate and faithfully replace the information of its genomic DNA with protein information. However, a phenomenon contrary to this flow of genetic information (central dogma) was found. Specifically, it was found that the primary structure of protein was changed by the insertion and deletion of uridine (U) in the transcription process of trypanosoma kinetoplastid DNA (1). Thereafter, such a phenomenon has been found one after another, in, for example, mitochondria and chloroplast mRNA of plants, mucosal mitochondrial mRNA, viral mRNA, and mammalian mRNA. In other words, a phenomenon known as "RNA editing", which causes an RNA mutation, was found even in the transcription of genetic information from DNA to mRNA by the action of RNA polymerase. Specifically, a specific DNA base sequence to be transcribed of the DNA base sequence is found to be replaced with a different base, a different base is found to be inserted, or the original base is found to be deleted, causing an RNA mutation. When such a RNA mutation is caused by transcription from DNA to RNA, protein synthesized based on the mutated RNA naturally has a different structure and functions from the proper protein to be generated. This can cause function failure and diseases.

Adenosine in mammalian brain RNA is known to be often deaminated and converted to inosine. Inosine is similar to guanosine in chemical structure, and can form a base pair with cytosine. Thus, inosine modification changes the codon, editing the amino acid sequence. The inosine modification is known to be common in the cells of the brain and the nervous system, and the deficiency of modification is observed in, for example, various neuropsychiatric disorders and cancers.

Thus, a change in the expression level and a failure in the function of intracellular proteins are clearly the causes at the molecular level of diseases. In other words, technologies capable of correcting the modulation of intracellular proteins are extremely important as the basis of medical and drug discovery technologies.

In contrast to DNA, mRNA is a transient intracellular molecule. mRNAs possess genetic information that determines the functions and expression levels of the encoded proteins. Hence, RNA-target genetic manipulation is capable of controlling target-protein functions, similar to genome editing, without the risk of damaging the original genomic information. In order to target intracellular RNA and control protein expression, short-chain RNAs, such as small-interfering RNAs (siRNAs) (Non-Patent Literature 7) and micro RNAs (miRNAs) (Non-Patent Literature 8), have been commonly used. Because these short-chain RNAs utilize an intracellular RNA-silencing mechanism (Non-Patent Literature 9), efficient target-RNA degradation can be achieved by simply expressing or introducing the short-chain RNA, without overexpressing any exogenous protein. Because of their simple structure and ease of use, siRNAs and miRNAs have been generalized as molecular tools for target-gene knockdown and applied also for nucleic acid drug discovery (Non-Patent Literature 10). In contrast to RNA interference technology, RNA mutagenesis technology that can modify RNA nucleotide sequences is not only a versatile gene mutation introduction tool in life science research, but has a large potential as a fundamental technology of drug discovery; however, no general method has yet been established.

In recent years, genome editing technology has made remarkable progress. It has become possible to freely alter DNA information with high efficiency and specificity (Non-Patent Literature 11). On the other hand, the mutation is permanently left in the cells genetically modified by genomic editing. Thus, there are still many problems that remain to be solved including ethical problems in medicine and drug discovery. One way to solve these problems and to control intracellular protein function is to introduce a mutation into RNA.

As one of in vivo RNA editing mechanisms, A-I editing (A-to-I RNA editing) mechanism where adenosine in RNA transcribed from DNA is converted to inosine by double-strand specific adenosine deaminase (ADAR) is a post-transcriptional modification mechanism widely present in almost all higher organisms (Non-Patent Literatures 12, 13, 14). One of the important roles of this A-I editing is the recoding of the genetic information at the transcription level, at which the converted inosine is read as guanosine by the translation mechanism. Thus, A-I editing is a powerful control of the function of various proteins by converting specific codons of a target protein.

As a result of recent transcriptome analysis, more than 20,000 editing sites have been identified on human intracellular RNA (Non-Patent Literature 15), and A-I editing is believed to be involved in various biological phenomena. Because inosine in RNA is translated as guanosine during protein synthesis, a protein having information (function) different from genome information is synthesized by RNA editing. That is, ADAR intracellularly introduces a mutation into RNA.

Intracellular ribosomal RNA (rRNA) modifications such as psuedouridylation (Non-Patent Literature 16) and 2'-hydroxymethylation (Non-Patent Literature 17) are processed by riboproteins composed of specific enzymes and small nucleolar RNAs (snoRNA) which function as guide RNAs (gRNAs) (Non-Patent Literature 18). In these riboproteins, gRNAs play an important role in guiding the modification enzyme towards the target by simple Watson-Crick base pairing with its antisense sequence. Thus, the modification activity can be altered simply by converting the artificial antisense sequence of the gRNAs (Non-Patent Literatures 19, 20, 21). That is, gRNAs can effectively control target-RNA modification.

Human ADAR2 (hADAR2), which is an isoform of the ADAR family protein, is expressed in various cell types in vivo. hADAR2 consists of two double-stranded RNA-binding domains (dsRBDs) and a deaminase domain, and preferentially targets adenosine localized in double-stranded RNA (dsRNA) but not in single-stranded RNA (FIG. 21a). ADAR proteins are not riboproteins, and directly bind target RNAs via their own dsRBS. Thus, it has so far been considered to be impossible to direct natural ADAR enzyme to a specific reaction by the gRNA technique. A highly functional artificial editing enzyme (editase) has been developed, and artificial gRNA is tethered to modified deaminase domains from ADARs by SNAP tag (SNAP-tag) technology (Non-Patent Literatures 22, 23, 24) or the RNA-peptide binding motif (Non-Patent Literature 25). These editases have been successful in regulating target protein functions by intracellular site-directed A-I editing. However, exogenous proteins are necessary for these RNA mutagenesis techniques, and technical difficulties still remain, considering versatility and generality. In addition, the residual editing activity of the modified deaminase domain has the possibility of adversely affecting the original editing state of maintaining homeostasis. Thus, if applied to humans, there is a danger of increasing the health risk. In other words, development of a methodology that does not use modified ADAR protein, that is, without using exogenous protein, and achieves target RNA editing induction with only gRNA is the key to establishing RNA mutagenesis methods generally applicable.

Heretofore, methods have been developed for introducing a target site-directed RNA mutation using an artificial complex of ADAAR mutant protein and guide RNA (Non-Patent Literature 26). These methodologies are based on the principle that complementary RNA region called guide region is used for recognition of target RNA, and active domain of ADAR is used for mutation introduction. It is an epoch-making method applicable to any target RNA. However, these conventional methods require a modified ADAR protein, which is disadvantageous in that complicated operations are required for mutagenesis.

Thus, the present inventors have noticed that if it is possible to introduce an RNA mutation in a target-site-directed manner only with guide RNA by using intracellular endogenous ADAR and by introducing intracellular ADAR freely using the principle of RNA editing, a new method can be developed that enables introduction of a site-directed RNA mutation to any intracellular target RNA As a result of intensive research to develop such a novel method, the present inventors have found that based on glutamate receptor mRNA precursor (GluR-B pre-mRNA) (Non-Patent Literature 27) specifically edited by ADAR 2 in vivo and an artificial editing substrate (miniSL RNA) (Non-Patent Literature 28) constructed by leaving only the area necessary for editing, dividing at a specific position while leaving only the ADAR binding region of this editing substrate can separate editing guide RNA and target RNA. In other words, the present inventors have found that the target editing guide RNA constructed in this design has a complementary region for recognizing the target RNA in addition to the ADAR binding region, and thus is applicable to any target RNA.

That is, the present inventors have found that such newly found target editing guide RNA can be designed as a functional RNA capable of introducing an RNA mutation in a target-site directed manner by utilizing ADAR which is endogenously expressed intracellularly. The target editing guide RNA constructed according to this design is composed of "complementary region", which forms a complementary strand with the target RNA, and "ADAR binding region", which has the capability of binding with naturally occurring ADAR and defines the spatial arrangement and orientation to allow effective guide editing of the target base adenosine. Thus, the inventors have found that by designing the sequence of the complementary region by matching this target editing guide RNA to the target RNA sequence, it is possible to construct a target editing guide RNA for introducing target site-directed A-I mutations into arbitrary intracellular RNA, and has completed the present invention.

Furthermore, the present inventors have developed an ADAR-guide RNA (AD-gRNA) that directly induces A-I editing by guiding hADAR2 (FIG. 21a). Using this approach, specific hADAR2 editing activity at a specific site is induced by programmable antisense sequences. Furthermore, site-directed RNA mutagenesis can also be achieved by a method of transfecting AD-gRNA expressing plasmid DNA in addition to a method of directly introducing chemically synthesized AD-gRNA into cells expressing hADAR2.

This AD-gRNA strategy is simple in design, easy to use, and is believed to be a fundamental technology for general approach of RNA mutagenesis.

RELATED ART LITERATURE

Non-Patent Literature

Non-Patent Literature 1: Heidenreich M, Zhang F. Applications of CRISPR-Cas systems in neuroscience. Nat Rev Neurosci 17, 36-44 (2016)

Non-Patent Literature 2: Kim Y G, Cha J, Chandrasegaran S. Hybrid restriction enzymes: zinc finger fusions to Fok I cleavage domain. Proc Natl Acad Sci USA 93, 1156-1160 (1996).

Non-Patent Literature 3: Porteus M H, Carroll D. Gene targeting using zinc finger nucleases. Nat Biotechnol 23, 967-973 (2005).

Non-Patent Literature 4: Zhang F, Cong L, Lodato S, Kosuri S, Church G M, Arlotta P. Efficient construction of sequence-specific TAL effectors for modulating mammalian transcription. Nat Biotechmol 29, 149-153 (2011).

Non-Patent Literature 5: Mali P, et al. RNA-guided human genome engineering via Cas9. Science 339, 823-826 (2013).

Non-Patent Literature 6: Araki M, Ishii T. Providing Appropriate Risk Information on Genome Editing for Patients. Trends Biotechnol 34, 86-90 (2016).

Non-Patent Literature 7: Elbashir S M, Harborth J, Lendeckel W, Yalcin A, Weber K, Tuschl T. Duplexes of 21-nucleotide RNAs mediate RNA interference in cultured mammalian cells. Nature 411, 494-498 (2001).

Non-Patent Literature 8: Ambros V. The functions of animal microRNAs. Nature 431, 350-355 (2004).

Non-Patent Literature 9: Carthew R W, Sontheimer E J. Origins and Mechanisms of miRNAs and siRNAs. Cell 136, 642-655 (2009).

Non-Patent Literature 10: Lam J K, Chow M Y, Zhang Y, Leung S W. siRNA Versus miRNA as Therapeutics for Gene Silencing. Mol Ther Nucleic Acids 4, e252 (2015).

Non-Patent Literature 11: (A) Cho, S. W.; Kim, S.; Kim, J. M.; Kim, J. S, Targeted genome engineering in human cells with the Cas9 RNA-guided endonuclease. Nat Biotechnol 2013, 31 (3), 230-2; (b) Mali, P.; Yang, L.; Esvelt, K. M.; Aach, J.; Guell, M.; DiCarlo, J. E.; Norville, J. E.; Church, G. MRNA-guided human genome engineering via Cas9. Science 2013, 339 (6121), 823-6.

Non-Patent Literature 12: Bass B L. RNA editing by adenosine deaminases that act on RNA. Annu Rev Biochem 71, 817-846 (2002).

Non-Patent Literature 13: Nishikura K. Functions and regulation of RNA editing by ADAR deaminases. Annu Rev Biochem 79, 321-349 (2010).

Non-Patent Literature 14: Wulff B E, Nishikura K. Substitutional A-to-I RNA editing. WIREs RNA 1, 90-101 (2010).

Non-Patent Literature 15: Peng, Z.; Cheng, Y.; Tan, B. C.; Kang, L.; Tian, Z.; Zhu, Y.; Zhang, W.; Liang, Y.; Hu, X.; Tan, X.; Guo, J.; Dong, Z.; Bao, L.; Wang, J, Comprehensive analysis of RNA-Seq data reveals extensive RNA editing in a human transcriptome. Nat Biotechnol 2012, 30 (3), 253-60.

Non-Patent Literature 16: Ganot P, Bortolin M L, Kiss T. Site-specific pseudouridine formation in preribosomal RNA is guided by small nucleolar RNA s. Cell 89, 799-809 (1997).

Non-Patent Literature 17: Cavaille J, Bachellerie J P. SnoRNA-guided ribose methylation of rRNA: structural features of the guide RNA duplex influencing the extent of the reaction. Nucleic Acids Res 26, 1576-1587 (1998).

Non-Patent Literature 18: Weinstein L B, Steitz J A. Guided tours: from precursor snoRNA to functional snoRNP. Curr Opin Cell Biol 11, 378-384 (1999).

Non-Patent Literature 19: Cavaille J, Nicoloso M, Bachellerie J P. Targeted ribose methylation of RNA in vivo directed by tailored antisense RNA guides. Nature 383, 732-735 (1996).

Non-Patent Literature 20: Zhao X, Yu Y T. Targeted pre-mRNA modification for gene silencing and regulation. Nat Methods 5, 95-100 (2008).

Non-Patent Literature 21: Karijolich J, Yu Y T. Converting nonsense codons into sense codons by targeted pseudouridylation. Nature 474, 395-398 (2011).

Non-Patent Literature 22: Stafforst T, Schneider M F. An RNA-deaminase conjugate selectively repairs point mutations. Angew Chem Int Ed Engl 51, 11166-11169 (2012).

Non-Patent Literature 23: Schneider M F, Wettengel J, Hoffmann P C, Stafforst T. Optimal guideRNAs for re-directing deaminase activity of hADAR1 and hADAR2 in trans. Nucleic Acids Res 42, e87 (2014).

Non-Patent Literature 24: Vogel P, Schneider M F, Wettengel J, Stafforst T. Improving site-directed RNA editing in vitro and in cell culture by chemical modification of the guideRNA. Angew Chem Int Ed Engl 53, 6267-6271 (2014).

Non-Patent Literature 25: Montiel-Gonzalez M F, Vallecillo-Viejo I, Yudowski G A, Rosenthal J J. Correction of mutations within the cystic fibrosis transmembrane conductance regulator by site-directed RNA editing. Proc Natd Acad Sci USA 110, 18285-18290 (2013).

Non-Patent Literature 26: Vollmar W, et al. RNA editing (R/G site) and flip-flop splicing of the AMPA receptor subunit GluR2 in nervous tissue of epilepsy patients. Neurobiol Dis 15, 371-379 (2004).

Non-Patent Literature 27: Lomeli, H.; Mosbacher, J.; Melcher, T.; Hoger, T.; Geiger, J. R.; Kuner, T.; Monyer, H.; Higuchi, M.; Bach, A.; Seeburg, P. H, Control of kinetic properties of AMPA receptor channels by nuclear RNA editing. Science 1994, 266 (5191), 1709-13.

Non-Patent Literature 28: Pokharel, S.; Beal, P. A, Highthroughput screening for functional adenosine to inosine RNA editing systems. ACS Chem Biol 2006, 1 (12), 761-5.

Non-Patent Literature 29: Nurpeisov V, Hurwitz S J, Sharma P L. Fluorescent dye terminator sequencing methods for quantitative determination of replication fitness of human immunodeficiency virus type 1 containing the codon 74 and 184 mutations in reverse transcriptase. J Clin Microbiol 41, 3306-3311 (2003).

Non-Patent Literature 30: Pokharel S, Beal P A. Highthroughput screening for functional adenosine to inosine RNA editing systems. ACS Chem Biol 1, 761-765 (2006).

Non-Patent Literature 31: Gommans W M, McCane J, Nacarelli G S, Maas S. A mammalian reporter system for fast and quantitative detection of intracellular A-to-I RNA editing levels. Anal Biochem 399, 230-236 (2010).

Non-Patent Literature 32: Fukuda M, Kurihara K, Yamaguchi S, Oyama Y, Deshimaru M. Improved design of hammerhead ribozyme for selective digestion of target RNA through recognition of site-directed adenosine-to-inosine RNA editing. RNA 20, 392-405 (2014).

Non-Patent Literature 33: Hanswillemenke A, Kuzdere T, Vogel P, Jekely G, Stafforst T. Site-Directed RNA Editing in Vivo Can Be Triggered by the Light-Driven Assembly of an Artificial Riboprotein. J Am Chem Soc 137, 15875-15881 (2015).

Non-Patent Literature 34: Stefl R, et al. The solution structure of the ADAR2 dsRBMRNA complex reveals a sequence-specific readout of the minor groove. Cell 143, 225-237 (2010).

Non-Patent Literature 35: Dabiri G A, Lai F, Drakas R A, Nishikura K. Editing of the GLuR-B ion channel RNA in vitro by recombinant double-stranded RNA adenosine deaminase. EMBO J 15, 34-45 (1996).

Non-Patent Literature 36: Yeo J, Goodman R A, Schirle N T, David S S, Beal P A RNA editing changes the lesion specificity for the DNA repair enzyme NEILL. Proc Natl Acad Sci USA 107, 20715-20719 (2010).

Non-Patent Literature 37: Keegan L P, Leroy A, Sproul D, O'Connell M A. Adenosine deaminases acting on RNA (ADARs): RNA-editing enzymes. Genome Biol 5, 209 (2004).

SUMMARY OF THE INVENTION

Problem to be Solved by the Invention

An aspect of an object of the present invention is to provide a method for introducing a site-directed RNA mutation including converting the target base adenosine (A) to inosine (I) in the target RNA generated upon transcription from genomic DNA to mRNA by inducing RNA editing capability by the action of double-strand specific adenosine deaminase (ADAR: adenosine deaminases acting on RNA).

Another object of the present invention is to provide a method for introducing a site-directed RNA mutation including translating A-I edited inosine (I) into guanosine (G).

Another object of the present invention is to provide a target editing guide RNA for use in a method for introducing a site-directed RNA mutation for RNA editing RNA mutations in a target RNA by the action of ADAR enzyme.

In a still further aspect of the present invention, in a method for introducing a site-directed RNA mutation for RNA editing a target base adenosine in a target RNA, it is another object to provide a target RNA-target guide RNA complex where ADAR is fixed for RNA editing and functions as a base for inducing RNA editing capability.

Means for Solving the Problem

In order to achieve the above objects, an aspect of the present invention provides a method for introducing a site-directed RNA mutation including causing ADAR to act on a target base adenosine (A) in a target RNA targeted for RNA editing to induce RNA editing capability to convert the target base adenosine (A) into inosine (I) by A-I editing.

Specifically, the present invention provides a method for introducing a site-directed RNA mutation including reacting a target RNA having an RNA mutation to be targeted for RNA editing with a target editing guide RNA to obtain a target RNA-target editing RNA complex having a double-stranded structure, allowing an ADAR enzyme to act to induce RNA editing capability, and converting target base adenosine (A) targeted for RNA editing to inosine (I) by A-I editing.

The present invention also provides a method for introducing a site-directed RNA mutation including further converting inosine (I) converted by A-I editing to guanosine (G).

Another aspect of the present invention provides a target editing guide RNA complementary to a target RNA having a target base adenosine targeted for RNA editing in order to construct the above-described target RNA-target editing guide RNA complex which induces RNA editing by ADAR enzyme and performs conversion to inosine.

Another aspect of the present invention provides a target RNA-target editing guide RNA complex which is complementary to the target RNA having the target base adenosine and the target editing guide RNA to construct a double-stranded structure, and induces RNA editing by the ADAR enzyme to convert the adenosine into inosine.

Effects of the Present Invention

The method for introducing a site-directed RNA mutation according to the present invention is extremely versatile and useful because it can be applied independently and nonspecifically to any target RNA having the target base adenosine present at the target editing site.

In addition, the method of the present invention is an extremely useful and highly valuable method which allows RNA editing to be induced by using the in vivo ADAR mechanism. Thus, according to the method of the present invention, by administering to a patient, an RNA mutation which is a pathogenesis of diseases, can be controlled by converting the target base adenosine into inosine by A-I editing and transcribing the inosine into mRNA, translating the inosine into guanosine, and further controlling the expression level of the causative protein of disease by the A-I editing. Thus, it can be expected that the method of the present invention plays an important role as a useful tool for research and development of drug discovery.

BRIEF DESCRIPTION OF THE DRAWINGS

FIG. 21 shows construction of a guide RNA of site-directed A-I editing;

FIG. 22A shows a sequence of ADg-GFP_A200;

FIG. 24 illustrates the construction of AD-gRNA using a framework based on modified GluR2 RNA; (a) shows the sequence of the substrate hADAR2 structure and a predicted secondary structure, (b) shows the structure of the sequence of sADg-GFP-A200 (top) and sADg-rGFP-A200 (bottom); (c) shows in vitro editing-inducing activity of sADg-GFP_A200 and sADg-rGFP_A200;

FIG. 25 shows analysis results of editing specificity using cis-type substrate RNA; (a) shows the actual sequences of eSL_AAA RNA and eSLr_AAA RNA; (b) shows sequence chromatograms of eSL_AAA RNA and eSLr_AAA RNA;

FIG. 26 shows the results of analysis of adjacent specificity of AD-gRNA-induced RNA;

FIG. 27 shows the effect of additional base pairing region on specificity and efficiency of AD-gRNA-induced RNA;

FIG. 35 shows the editing efficiency of AD-gRNAs generated by splitting at various points of the editing substrate RNA; (a) is a diagram showing a dividing line on a hairpin substrate for generating ADg-RNAs; (b) shows the sequence of target RNA (GFP mRNA) and 5'-antisense ADg-RNAs: ADg (L3) is the same as that of sADg-rGFP_A200 used in FIG. 24; (c) shows the editing induction activity of each gRNA;

FIG. 61 is a 5'-target RNA-3'-target editing RNA complex [LXIA].

FIG. 62 is a 3'-target RNA-5'-target editing RNA complex [LXVIA].

FIG. 63 is a 5'-edited target RNA [LXIIA].

FIG. 64 is a 3'-edited target RNA [LXVIIA].

FIG. 65 is a 3'-target editing guide RNA represented by formula [LIB].

FIG. 66 is a 5'-target editing guide RNA represented by formula [LVIB].

FIG. 67 is a 5'-target RNA-3'-target editing guide RNA complex represented by formula [LXIB].

FIG. 68 is a 3'-target RNA-5'-target editing guide RNA complex represented by formula [LXVIB].

FIG. 69 is a 5'-edited target RNA represented by formula [LXIIB].

FIG. 70 is a 3'-edited target RNA represented by formula [LXVIIA].

FIG. 71 is a 5'-translated target RNA [LIVA].

FIG. 72 is a 3'-translated target RNA [LIXA].

FIG. 73 is a 5'-target RNA [IA].

FIG. 74 is a 3'-target editing guide RNA [IIA].

FIG. 75 is a 5'-target RNA-3'-target editing guide RNA complex [IIIA].

FIG. 76 is a 5'-edited target RNA [IVA].

FIG. 77 is a 5'-translated target RNA [VA].

FIG. 78 is a 3'-target RNA [VIA].

FIG. 79 is a 5'-target editing guide RNA [VIIA].

FIG. 80 is a 5'-target RNA-3'-target editing guide RNA complex [VIIIA].

FIG. 81 is a 5'-edited target RNA [IXA].

FIG. 82 is a 5'-translated target RNA [XA].

FIG. 83 is a 3'-target editing guide RNA [IiB].

FIG. 84 is a 5'-target RNA-the 3'-target editing guide RNA complex [IIIB].

FIG. 120 is a second target editing scheme.

FIG. 121 is a second target editing scheme.

FIG. 122 is an ADAR binding core region.

FIG. 123 is a target editing scheme.

FIG. 124 is a scheme to obtain editing substrate [XLIA] designed by exchanging the target editing site of the editing substrate [XLA].

FIG. 125 is examples of 5'-target editing guide RNAs.

FIG. 126 is examples of 3'-target editing guide RNAs.

FIG. 127 is a scheme to convert the target base adenosine of the target RNA to inosine.

FIG. 128 is a scheme to convert the target base adenosine of the target RNA to inosine.

FIG. 129 is a scheme to convert the target base adenosine of the target RNA to inosine.

MODE FOR CARRYING OUT THE INVENTION

Figure 1:
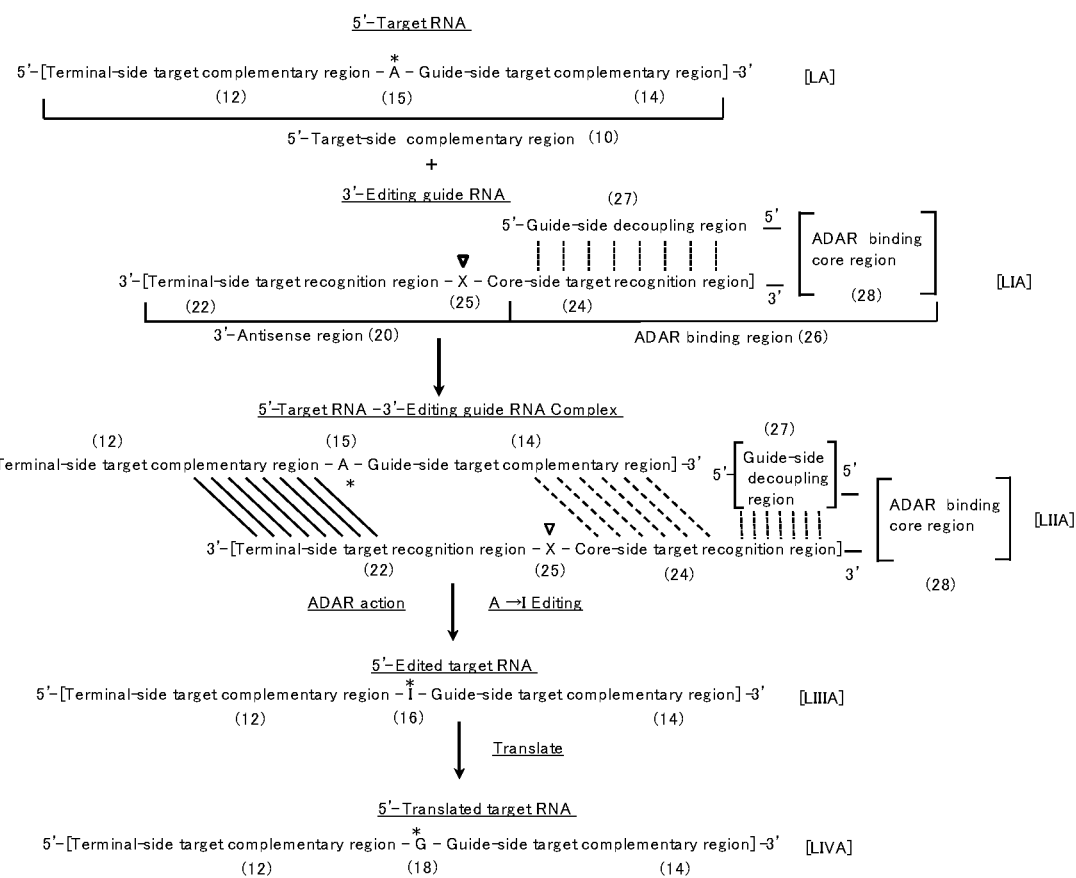
FIG. 1 is a scheme showing a method for introducing a site-directed RNA mutation according to a first aspect of the present invention.

The method for introducing a site-directed RNA mutation according to the present invention includes reacting a target RNA containing a target base adenosine (A) to be subjected to RNA editing or a specific region thereof with a target editing guide RNA to prepare a double-stranded complex, binding ADAR to the formed double-stranded complex to induce its RNA editing capability, thereby converting the target base adenosine present in the target RNA into inosine. The inosine thus converted is further translated into guanosine.

Thus, in the present invention, it is preferable to first select RNA which includes the target base adenosine (A) to be subjected to RNA editing as a target RNA. Such RNAs are preferably selected from naturally occurring RNAs, such as serotonin receptors, glutamate receptors, and membrane voltage-dependent potassium channels. However, any RNA having a target base adenosine can be selected.

When a target RNA to be subjected to RNA editing is selected, a specific region containing the target base adenosine to be subjected to RNA editing is selected from among them. In selecting this specific region, it is preferable to construct the specific region composed of a base sequence of a predetermined length on both sides of the target editing site. In the present invention, in addition to the fragment consisting of only this specific region, it is obviously also possible to use a full-length RNA or partial length RNA containing such a specific region. Thus, as used herein, the term "target RNA" is used to mean not only a fragment consisting of only a specific region but also a full-length RNA or a partial length RNA including a specific region or a partial length.

If a specific region of the target RNA is thus selected, then the target editing guide RNA is designed and constructed so that the specific region substantially pairs with the target RNA to form a complementary strand. Once a specific region of such a target editing guide RNA is designed and constructed, it is preferable to design and construct such that the specific region is bound to the ADAR binding core region.

Thus, the method for introducing a site-directed RNA mutation according to the present invention allows the target RNA that is designed and constructed as described above and the target editing guide to form complementary strands of corresponding specific regions to form a complex to construct a double-stranded structure, and induces the A-I editing capability by the action of ADAR to convert the target base adenosine of the target RNA to inosine.

Hereinafter, the modes of the method for introducing a site-directed RNA mutation of the present invention will be specifically described with reference to the attached drawings. It is to be noted that the method of the present invention described below explains the best modes for carrying out the present invention and does not intend to limit the present invention in any meaning.

The present invention can be roughly classified into two aspects depending on the sequence format of the target RNA to be targeted for RNA editing. The first aspect is the sequence format denoted by 5'-target RNA, and the second aspect is the sequence format denoted by 3'-target RNA. "5'-target RNA" means a target target RNA in which the 5' end exists on the left side (to the attached drawing) of the target base adenosine (A) of the target RNA to be targeted for RNA editing. "3'-target RNA" means a target RNA in which the 3' end exists on the left side (to the attached drawing) of the target base adenosine (A) to be edited. In this specification. "5'-target RNA" and "3'-target RNA" are sometimes simply referred to as target RNA without strictly distinguishing them from each other.

Figure 2:
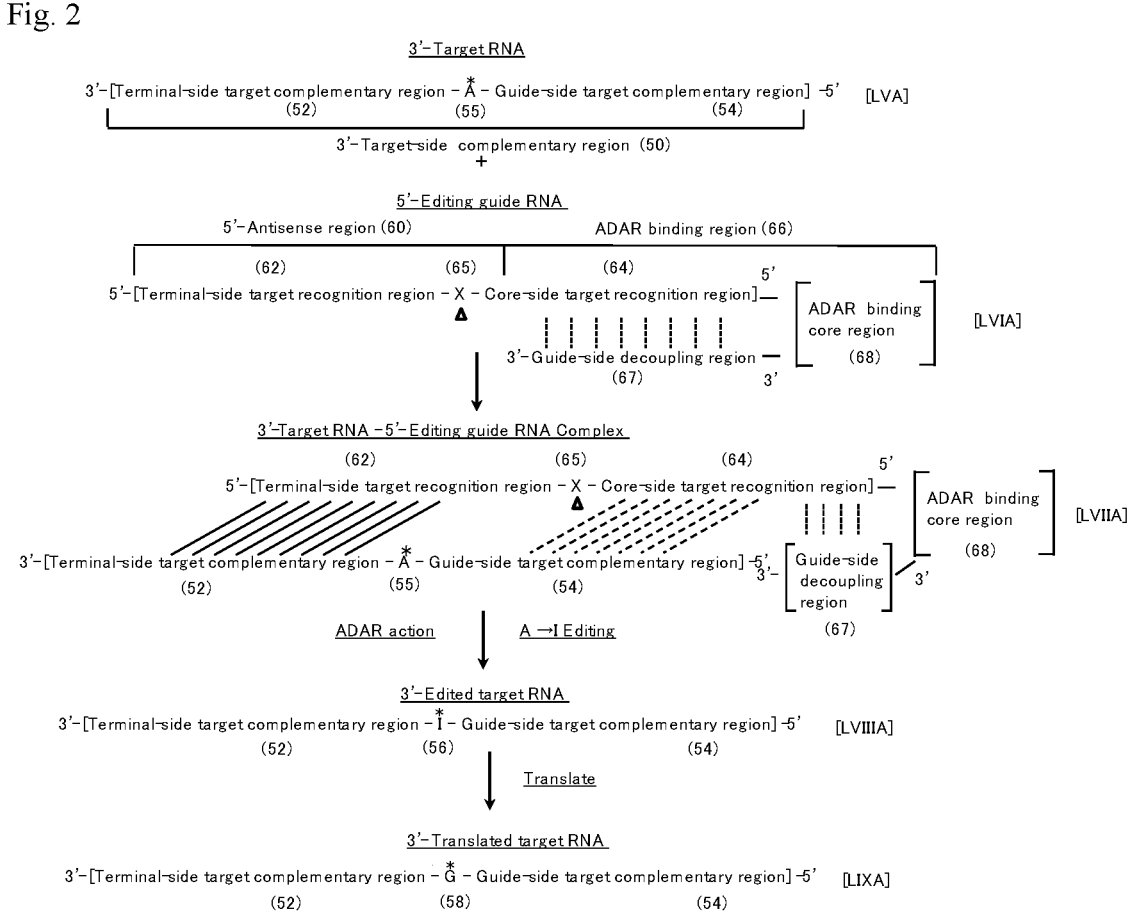
FIG. 2 is a scheme showing a method for introducing a site-directed RNA mutation according to a second aspect of the present invention.

Thus, the method for introducing a site-directed RNA mutation according to the first aspect and the second aspect of the present invention will be described with reference to FIGS. 1 and 2, respectively.

Figure 39:
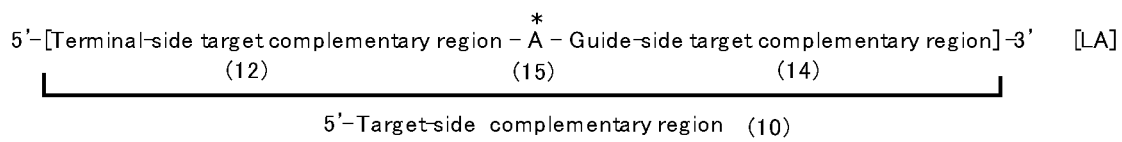
FIG. 39 is a 5'-target RNA represented by formula [LA].
Figure 40:
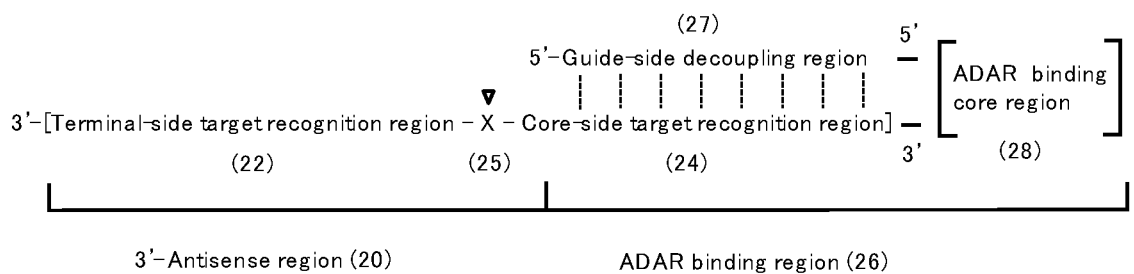
FIG. 40 is a 3'-Editing guide RNA represented by formula [LIA].
Figure 41:
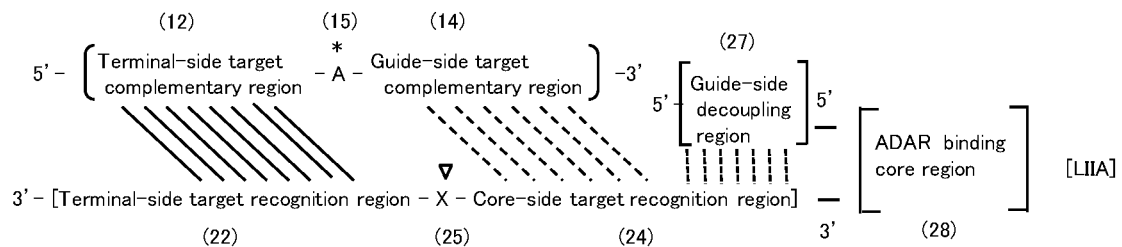
FIG. 41 is a 5'-target RNA-3'-target editing guide RNA complex represented by formula [LIIA].
Figure 42:
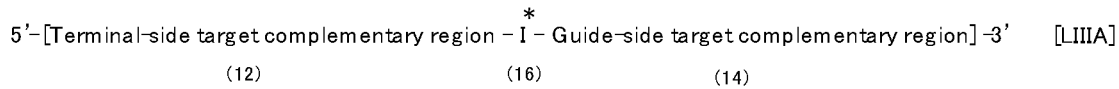
FIG. 42 is a 5'-editing target RNA represented by formula [LIIIA].

A method for introducing a site-directed RNA mutation according to the first aspect of the present invention includes reacting 5'-target RNA represented by formula [LA] in FIG. 39 with 3'-target editing guide RNA represented by formula [LIA] in FIG. 40 to obtain 5'-target RNA-3'-target editing guide RNA complex represented by formula [LIIA] in FIG. 41, causing ADAR to act to induce A-I editing to perform conversion to 5'-editing target RNA represented by formula [LIIIA] in FIG. 42, and deaminating the target base adenosine (A) of the complex (solid triangle) to perform conversion to inosine (I). The thus converted inosine is translated into guanosine. Hereinafter, for ease of explanation, this method is also referred to as a first target editing scheme.

Figure 43:
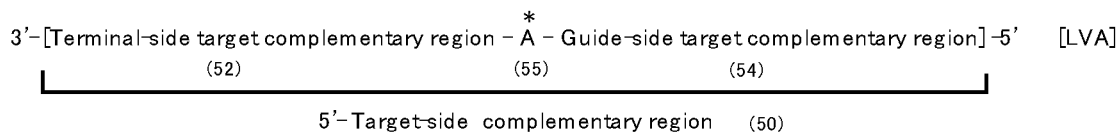
FIG. 43 is a 3'-target RNA represented by formula [LVA].
Figure 44:
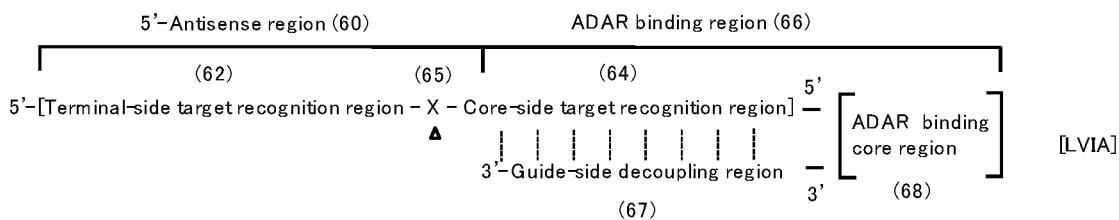
FIG. 44 is a 5'-target editing guide RNA represented by formula [LVIA].
Figure 45:
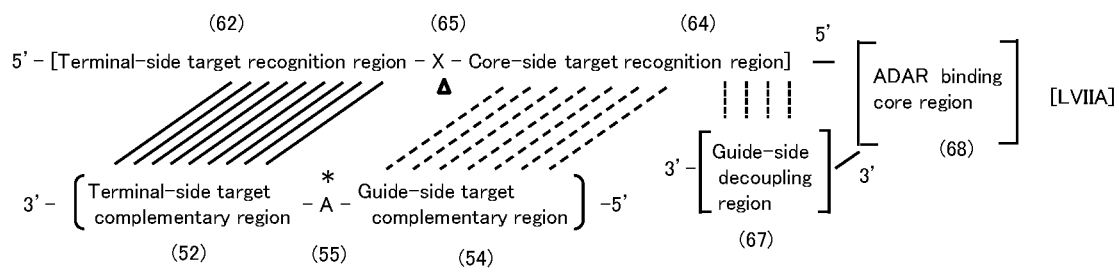
FIG. 45 is a 3'-target RNA-5'-target editing guide RNA complex represented by formula [LVIIA].
Figure 46:
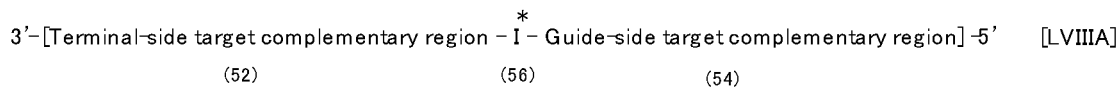
FIG. 46 is a 3'-editing target RNA represented by formula [LVIIIA].

The method for introducing a site-directed RNA mutation according to the second aspect of the present invention is substantially the same as the method for introducing a site-directed RNA mutation according to the first embodiment, and includes reacting 3'-target RNA represented by formula [LVA] in FIG. 43 with 5'-target editing guide RNA represented by formula [LVIA] in FIG. 44 to obtain 3'-target RNA-5'-target editing guide RNA complex represented by formula [LVIIA] in FIG. 45, causing ADAR to react to induce A-I editing to perform conversion to 3'-editing target RNA represented by formula [LVIIIA] in FIG. 46, and deaminating the target base adenosine (A) of the complex (solid triangle) to perform conversion to inosine (I) (marked with a solid triangle). The thus converted inosine is trans- lated into guanosine. Hereinafter, for ease of explanation, this method is also referred to as a second target editing scheme.

The 5'-target RNA [LA] of the first aspect used in the present invention consists of a 5'-target side complementary region (10). The 5'-target side complementary region (10) consists of a terminal side target complementary region (12), a guide side target complementary region (14), and a target base adenosine (A) represented by A* (15). Likewise, the 3'-target RNA [LVA] of the second aspect consists of a 3'-target complementary region (50). The 3'-target complementary region (50) consists of a terminal side target complementary region (52), a guide side target complementary region (5), and a target base adenosine (A) represented by A * (55).

In the present invention, the terminal-side target complementary region (12, 52) of the target RNA is a base sequence composed of the same or different bases selected from adenine, cytosine, guanine, and uracil. Although it is not particularly limited, it is generally constructed to have a base sequence of about 40 bases, preferably about 30 bases, and more preferably about 20 bases.

The guide-side target complementary region (14, 54) of the target RNA is a base sequence composed of the same or different bases selected from adenine, cytosine, guanine, and uracil. Although the number of bases is not particularly limited, it is constructed to have a sequence of about 1 to 15, preferably 1 to 12, more preferably 1 to 10, and particularly preferably 1 to 5 bases. When complexing the base sequence of the guide-side target complementary region of any target RNA with the editing guide RNA to be described later, it is preferable to construct it to base pair with the base sequence of the X-adjacent part of the core-side target recognition region of the editing guide RNA.

In the target RNA, A* (15, 55) means the target base adenosine targeted for editing existing at the target editing site (* mark) respectively.

In the present invention, the target editing guide RNA consists of an antisense region (20, 60) and an ADAR binding region (26, 66). The antisense region (20, 60) is constructed to respectively form a complementary strand with the 5'-target RNA of the first aspect or the 3'-target RNA of the second aspect.

Furthermore, the 3'-antisense region (20) of the 3'-target editing guide RNA includes a terminal side target recognition region (22), an X-adjacent part region of a core-side target recognition region (24) and a target editing-inducing base X (25) (marked with triangle) for target-editing-inducing the target base adenosine of 5'-target RNA.

Likewise, the 5'-antisense region (60) of the 5'-target editing guide RNA contains the terminal side target recognition region (62), the X-adjacent part region of the core-side target recognition region (64), and a target editing inducing base X (65) (marked with triangle) for target-editing-inducing the target base adenosine (A) of 3' target RNA [LVA].

The terminal side target recognition region (22, 62) of the target editing guide RNA of the present invention is a base sequence consisting of the same kind and different kinds of bases selected from adenine, cytosine, guanine, and uracil. Although not particularly limited, it is generally preferable to construct base regions each consisting of about 40, preferably about 30, and more preferably about 20 base sequences. However, the number of constituent bases is the same as the number of bases of the terminal-side target complementary region (12, 52) of the corresponding target RNA, respectively, so that the corresponding bases are paired to form a base pair.

The X-adjacent part region of the core side target recognition region of the antisense region is a base sequence consisting of the same and different bases selected from adenine, cytosine, guanine, and uracil, constitutes a base sequence consisting of a base sequence of generally 1 to 15, preferably 1 to 12, more preferably 10 or less, particularly preferably 1 to 5 bases, and forms a base pair with the base sequence of guide side target complementary region of the target RNA, respectively. When forming a complex with the target RNA, the base sequence of the X-adjacent portion of the core side target recognition region is constructed so as to base pair with the base sequence of the guide side decoupling region to form a base pair.

The ADAR binding region adjacent to the antisense region is composed of an ADAR adjacent region of the core side target recognition region, an ADAR binding core region, and a guide side decoupling region, each consisting of the same or different bases selected from adenine, cytosine, guanine, and uracil. It is a base region where the number of the bases in the ADAR adjacent region of the core side target recognition region and the guide side decoupling region is generally from 0 to 10, preferably about 5, and each constituent base is constructed so as to base pair with each other to form a base pair.

In the present invention, in order that ADAR can exert A-I editing-inducing capability, the base sequence of the ADAR binding region can be fixed in a certain degree to a specific base sequence or a similar base sequence without greatly modifying the base sequence of the ADAR binding region. On the other hand, in the base sequence of the antisense region of the editing guide RNA, since the target RNA containing the target base A of interest is vastly different in base sequence and has a very diverse base sequence, it is necessary to construct so that the type and length of the base sequence can be freely changed. It is also possible to adjust the A-I editing capability of ADAR by increasing or decreasing the number of bases in the base sequence of the antisense region of the editing guide RNA, particularly the number of bases in the base sequence of the X-adjacent region of the core side target recognition region.

In addition, the ADAR binding core region (28, 68) has an incomplete double-stranded RNA structure with a stem-loop structure composed of the same or different bases selected from adenine, cytosine, guanine, and uracil. This stem-loop structure has two incompletely complementary base sequence structures with a loop structure interposed therebetween, and the base sequence of each single strand is the same or different base sequence. Although the number of the bases is not particularly limited as long as it does not impair the editing inducing capability, it is typically about to 40, and preferably about 20 to 30. Also, in the loop structure, the corresponding constituent bases do not form complementary strands to each other but are composed of 4 to 8, preferably 4 to 5 same or different bases. Furthermore, the base sequence of one single strand of this incompletely complementary double-strand has an ADAR adjacent part of the core side target recognition region at its end, and the base sequence of the other single strand has its end connected to the guide side decoupling regions, respectively.

Furthermore, the ADAR binding core region is a region inducing the action of ADAR by binding with ADAR, and has the function of A-I editing the target base adenosine of the target RNA to convert it into inosine. In other words, RNA editing by ADAR can exert the function of inducing RNA editing capability of ADAR by ADAR being fixed to the ADAR fixing core region of the target editing guide RNA. As the ADAR having A-I editing capability, for example, hADAR1 and hADAR2 can be cited as ADAR, for example.

In the present invention, the target RNA and the target editing guide RNA complementarily complex to form a target RNA-target editing guide RNA complex. Specifically, the target side complementary region of the target RNA and the X-adjacent partial base sequence of the core side target recognition region, which is a part of the antisense region of the target editing guide RNA, are base-paired to form a complementary strand target RNA-target editing guide RNA complex. More specifically, the terminal-side target complementary region of the target RNA and the terminal-side target recognition region of the target editing guide RNA, and the guide-side target complementary region of the target RNA and the core-side target recognition region of the target editing guide RNA are paired to form a complementary strand, respectively, thereby forming a target RNA-target editing guide RNA complex.

More specifically, in the first target editing scheme of the present invention, the corresponding bases of the constituent bases of the terminal side target complementary region (12) of the 5'-target RNA [LA] and the constituent bases of the 3'-terminal-side target recognition region (22) of the 3'-target editing guide RNA [LIA] are base-paired to form base pairs to construct the 5'-target RNA-3'-target editing guide RNA complex [LIIA].

Similarly, in the second target editing scheme of the present invention, the corresponding bases of the constituent bases of the terminal side target complementary region (52) of the 3'-target RNA [LVA] and the constituent bases of the 5'-terminal side target recognition region (62) of the 5'-target editing guide RNA ILIA are base-paired to form base pairs to construct the 3'-target RNA-5'-target editing guide RNA complex [LVIIA].

On the other hand, in the complex [LIIA], the constituent bases of the guide-side target complementary region (14) of the 5'-target RNA [LA] are constructed to base pair with the constituent bases of the X-adjacent part region of the core-side target recognition region (24) of the editing guide RNA, and the constituent bases of the ADAR adjacent part region are constructed to base pair with the constituent bases of the guide side decoupling region (27) to form base pairs.

Similarly, in the complex [LVIIA], the guide-side target complementary region (54) of the 3'-target RNA [LVA] is constructed to base pair with the constituent bases of the X-adjacent part region of the core-side target recognition region (64) of the editing guide RNA [LVIA], and the ADAR adjacent region is constructed to base pair with the constituent bases of the guide side decoupling region (67) to form base pairs.

As described above, the number of bases in the core side target recognition region of the target editing guide RNA is constructed to be the same as the total number of bases in the guide side target complementary region of the target RNA and the guide side decoupling region of the target editing guide RNA. Thus, it is preferable to design the number of bases in the base sequence of the X-adjacent part region of the core-side target recognition region of the target editing guide RNA to be larger than the number of bases in the base sequence of the guide side decoupling region of the ADAR binding region. Adjusting the number of the former in this way allows the A-I editing capability by ADAR to be adjusted.

In the present invention, the target RNA and the target editing guide RNA are complexed to form a double-stranded structure, whereby ADAR acts on the ADAR fixing core region of the target editing guide RNA, induces RNA editing capability to allow the target base adenosine (A) present in the target RNA bound to the complex to be A-I edited and converted to inosine (I).

Figure 47:
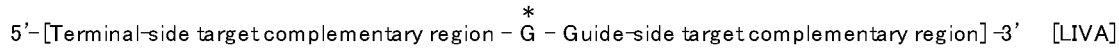
FIG. 47 is a 5'-translated target RNA [LIVA].
Figure 48:
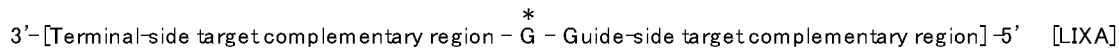
FIG. 48 is a 3'-translated target RNA [LIXA].

Furthermore, as described above, the edited target RNA in which the target base adenosine is converted to inosine is translated into guanosine (G). That is, in the present invention, the inosine (I) of each of the RNA-edited 5'-editing target RNA [LIIIA] of 5'-target RNA and 3'-editing target RNA [LVIIIA] of 3'-target RNA is translated into guanosine (G) as represented by 5'-translated target RNA [LIVA] in FIG. 47 and 3'-translated target RNA [LIXA] in FIG. 48.

In the above target editing scheme, a target editing inducing base X (25, 26) which is positioned at target editing site (marked with triangle) corresponding to a target base A (*) in the target RNA includes any base which does not complement the target base A of cytosine (C), guanosine (G), adenosine (A) and uridine. In view of A-I editing capability, cytosine can be preferably used as the target editing inducing base.

Therefore, the present invention provides a method for introducing a site-directed RNA mutagenesis in which a target editing inducing base (X) corresponding to a target editing site (marked with triangle) is constructed as a base cytosine (C) as a preferable embodiment.

Figure 49:
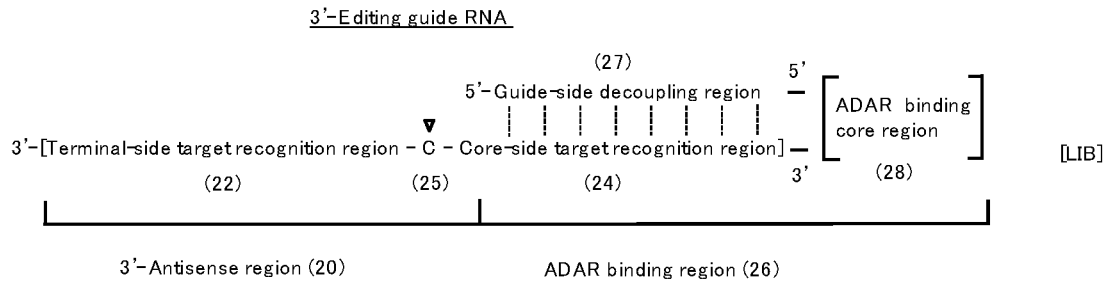
FIG. 49 is a 3'-target editing guide RNA [LIB].
Figure 50:
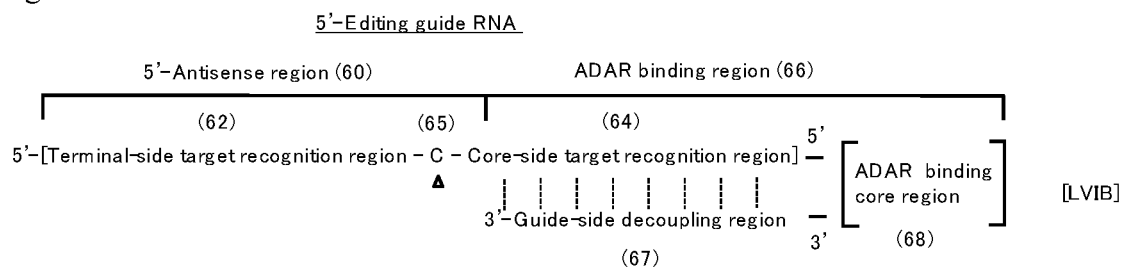
FIG. 50 is a 5'-target editing guide RNA [LVIB].
Figure 51:
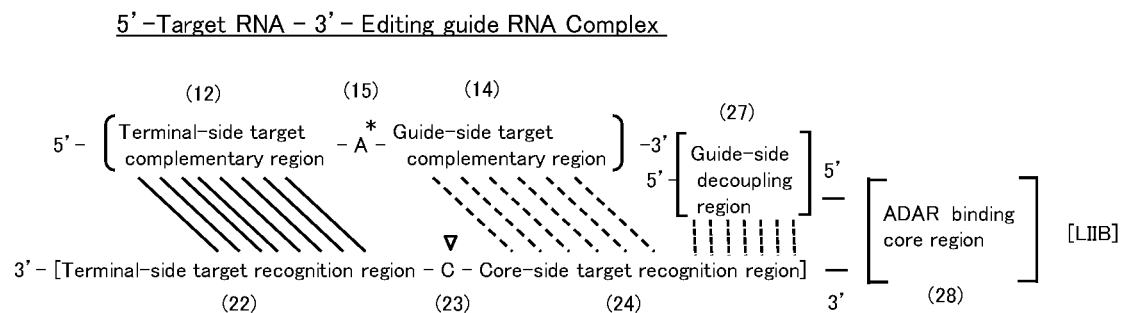
FIG. 51 is a 5'-target RNA-3'-target editing guide RNA complex [LIIB].
Figure 52:
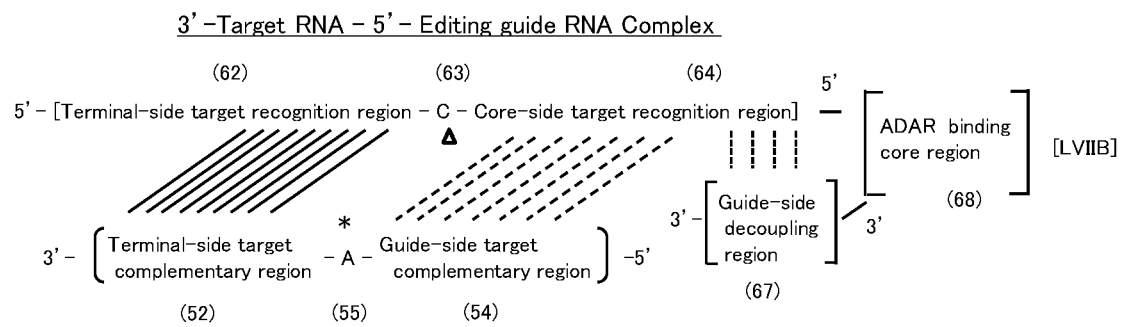
FIG. 52 is a 3'-target RNA-5'-target editing guide RNA complex [LVIIB].
Figure 53:
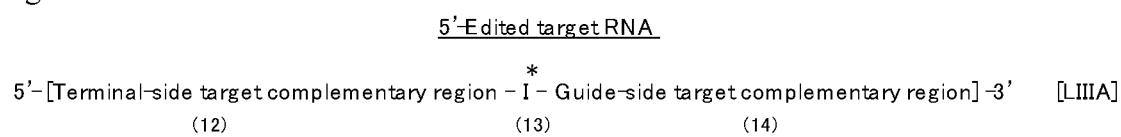
FIG. 53 is a 5'-edited target RNA [LIIIA].
Figure 54:
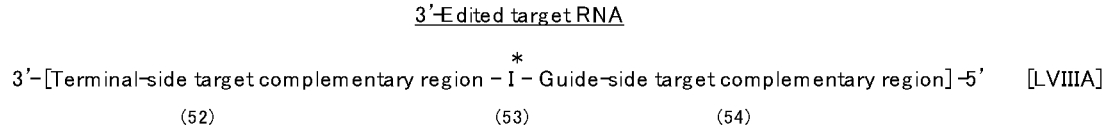
FIG. 54 is a 3'-edited target RNA [LVIIIA].

That is, a preferred embodiment of the present invention is characterized by reacting a 3'-target editing guide RNA [LIB] in FIG. 49 in which cytosine is used as the target editing inducing base X in the first target editing scheme or a 5'-target editing guide RNA [LVIB] in FIG. 50 in which cytosine is used as the target editing inducing base X in the second target editing scheme with a corresponding target RNA respectively, to compose and obtain a 5'-target RNA-3'-target editing guide RNA complex [LIIB] in FIG. 51, or a 3'-target RNA-5'-target editing guide RNA complex [LVIIB] in FIG. 52, causing ADAR to react with the complex to induce A-I editing and convert the complex to a 5'-edited target RNA [LIIIA] in FIG. 53, or a 3'-edited target RNA [LVIIIA] in FIG. 54, respectively, and converting the target base adenosine in the target RNA to inosine more efficiently and easily.

Figure 55:
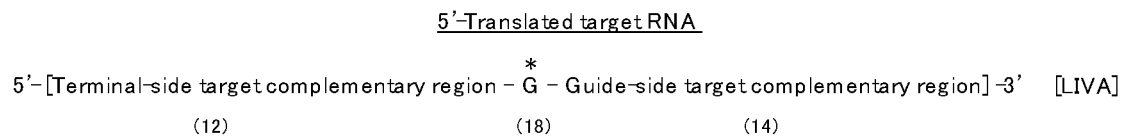
FIG. 55 is a 5'-translated target RNA [LIVA].
Figure 56:
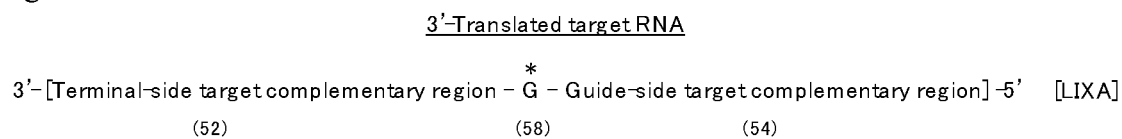
FIG. 56 is a 3'-translated target RNA [LIXA].

Inosine (I) of each edited target RNA which has been A-I edited as described above is translated into guanosine (G) as shown in the 5'-translated target RNA [LIVA] in FIG. 55, or the 3'-translated target RNA [LIXA] in FIG. 56.

Figure 3:
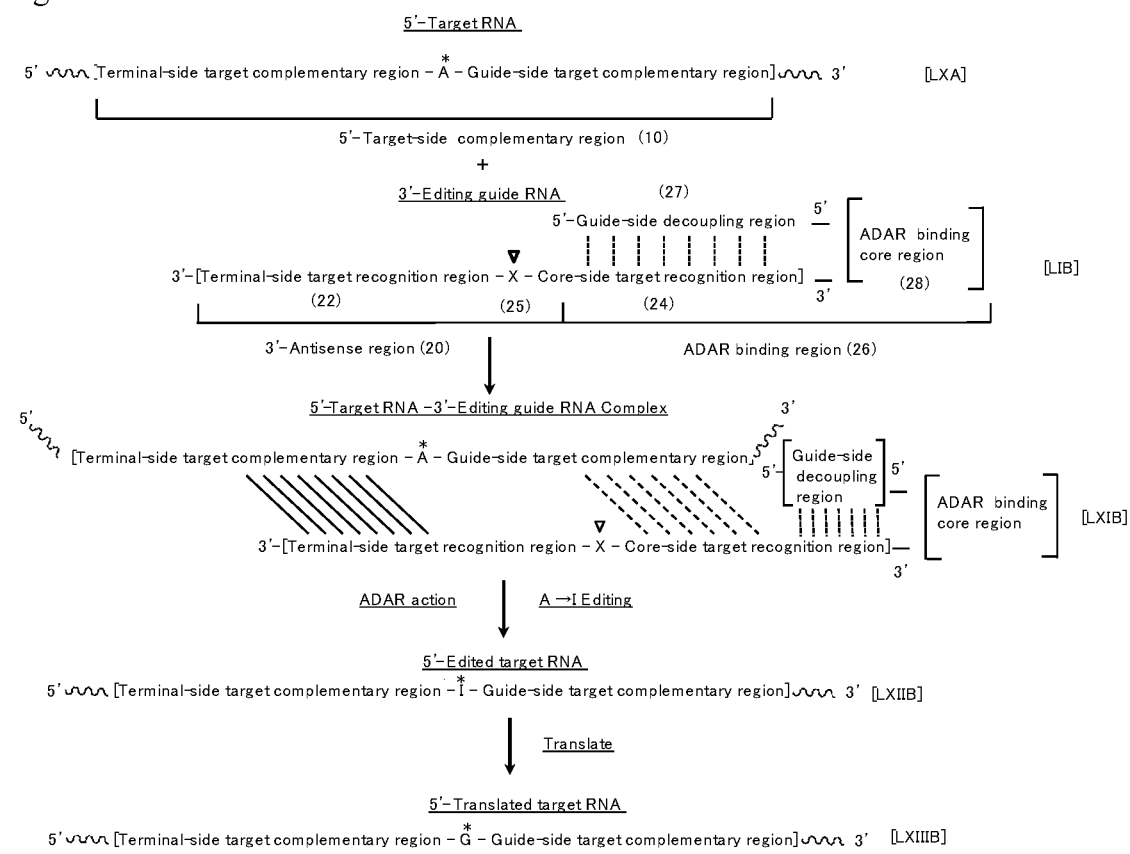
FIG. 3 is a scheme showing a method for introducing a site-directed RNA mutation according to another embodiment of the first aspect of the present invention.
Figure 4:
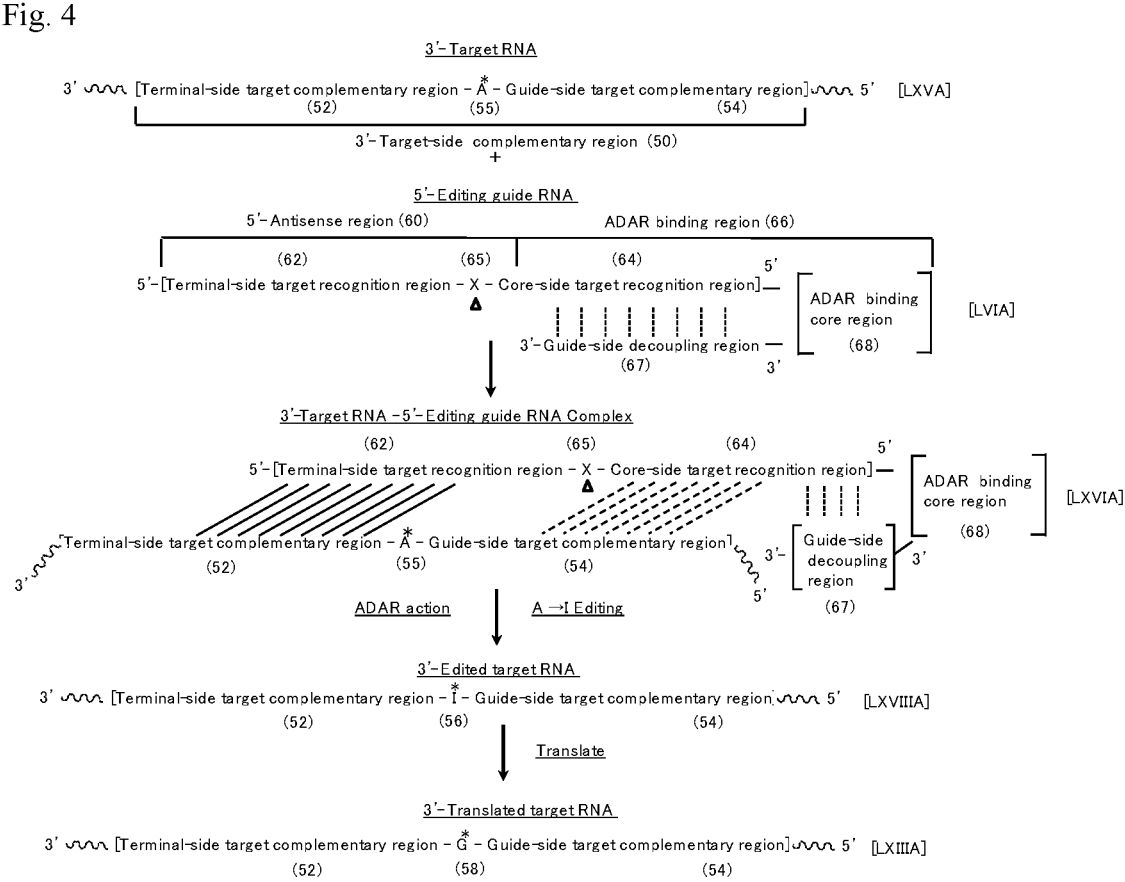
FIG. 4 is a scheme showing a method for introducing a site-directed RNA mutation according to another embodiment of the second aspect of the present invention.
Figure 57:
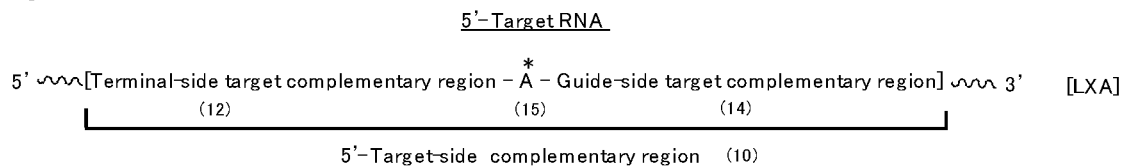
FIG. 57 is a 5'-target RNA [LXA].
Figure 58:
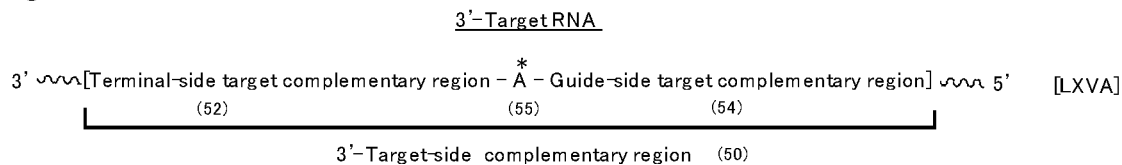
FIG. 58 is a 3'-target RNA [LXVA].
Figure 59:
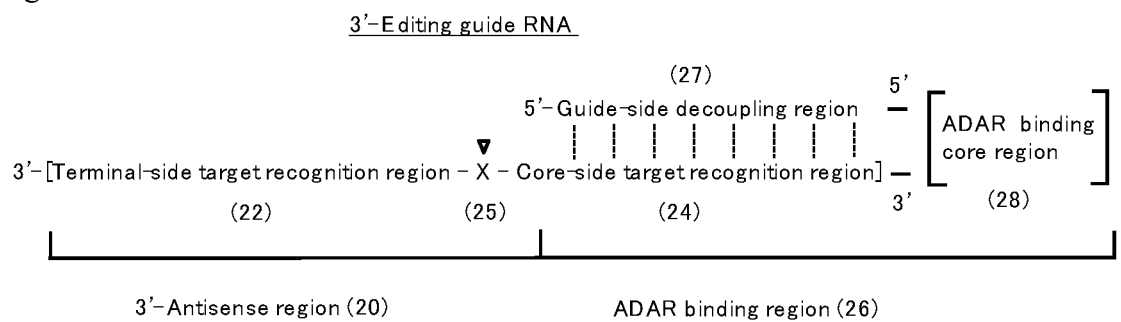
FIG. 59 is a 3'-target editing guide RNA [LIA].
Figure 60:
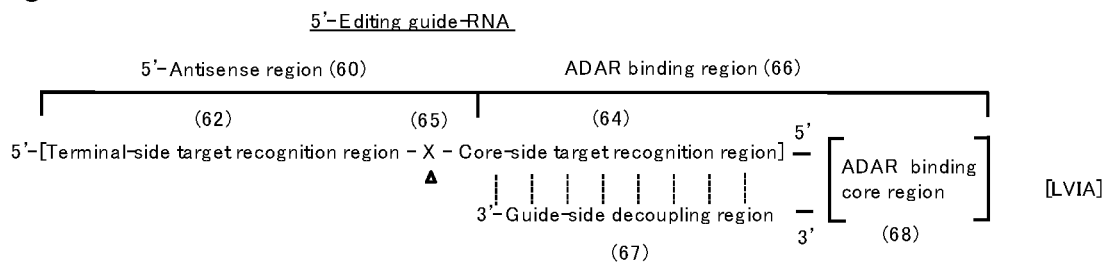
FIG. 60 is a 3'-target editing guide RNA [LVIA].

Furthermore, when a full length RNA or a partial length RNA longer than the base sequence of the target-side complementary region is used as the target RNA, the method for introducing a site-directed RNA mutation is constructed, as shown in FIG. 3 or FIG. 4, from reacting a 5'-target RNA [LXA] in FIG. 57, or a 3'-target RNA [LXVA] in FIG. 58 with a 3'-target editing guide RNA [LIA] in FIG. 59, or a 3'-target editing guide RNA [LVIA] in FIG. 60, respectively, obtaining a 5'-target RNA-3'-target editing RNA complex [LXIA] in FIG. 61, or a 3'-target RNA-5'-target editing RNA complex [LXVIA] in FIG. 62, and obtaining a 5'-edited target RNA [LXIIA] in FIG. 63, or a 3'-edited target RNA [LXVIIA] in FIG. 64 in which the target base adenosine is A-I edited to inosine, which is an RNA mutation of the target RNA by the action of ADAR, respectively.

Likewise, in a preferred embodiment of the present invention, in a method for introducing a site-directed RNA mutation in which cytosine (C) is used as a target editing-inducing base X (25, 65) (marked with triangle) corresponding to a target base adenosine (A) of the target RNA, a 3'-target editing guide RNA represented by formula [LIB] in FIG. 65 is used in place of the 3'-target editing guide RNA [LIA] in the first target editing scheme, or a 5'-target editing guide RNA represented by formula [LVIB] in FIG. 66 is used in place of the 5'-target editing guide RNA [LVIA] in the second target editing scheme, and is reacted with a corresponding target RNA to obtain a 5'-target RNA-3'-target editing guide RNA complex represented by formula [LXIB] in FIG. 67, or a 3'-target RNA-5'-target editing guide RNA complex represented by formula [LXVIB] in FIG. 68, and the ADAR is reacted with each of the complex inducing A-I editing, converting the target base adenosine to inosine, and obtaining a 5'-edited target RNA represented by formula [LXIIB] in FIG. 69, or a 3'-edited target RNA represented by formula [LXVIIA] in FIG. 70, and the target base adenosine targeted for RNA editing can be converted to inosine.

The edited target RNA converted to inosine as described above is converted into a 5'-translated target RNA [LIVA] in FIG. 71, or a 3'-translated target RNA [LIXA] in FIG. 72 and inosine is translated into guanosine.

As described above, the method for introducing a site-directed RNA mutation according to the present invention can easily convert the target base adenosine contained in the full-length target RNA or the partial length target RNA by A-I editing to the inosine by the action of ADAR Is possible.

Thus, the site-directed RNA mutation introduction method according to the present invention has been comprehensively described. Hereinafter, the site-directed RNA mutation introduction method according to the present invention will be described more specifically with reference to the drawings.

First, the site-directed RNA mutation introduction method of the present invention by the first target editing scheme will be described with reference to FIG. 5. The site-directed RNA mutation introduction method of the present invention shown in FIG. 5 more concretely represents the generic form shown in FIG. 1.

Figure 5:
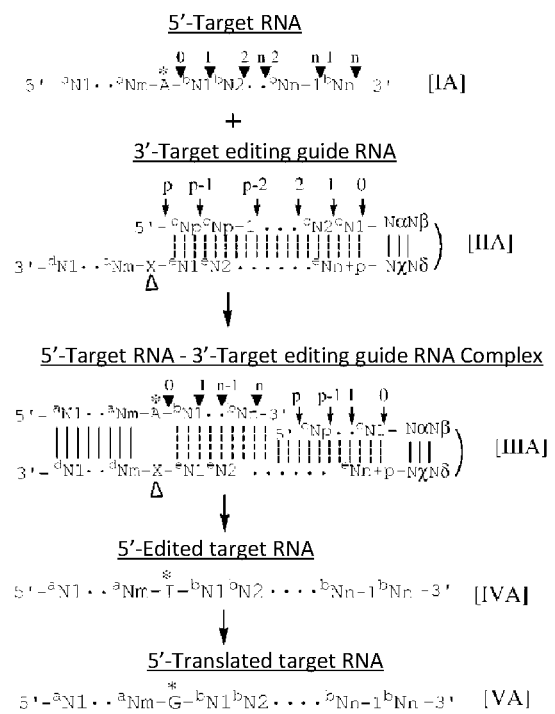
FIG. 5 is a scheme showing a method for introducing a site-directed RNA mutation according to a concrete embodiment of the first aspect of the present invention.

The method for introducing a site-directed RNA mutation of the present invention is constructed from RNA mutation editing in which, as indicated in FIG. 5, 5'-target RNA [IA] in FIG. 73 (in the formula, a symbol of $^{a}N1 \ldots {}^{a}Nm$ indicates a base sequence corresponding to the terminal-side target complementary region (12) of the 5'-target RNA, is a continuous base sequence constructed from combination of the same or different bases consisting of any base N selected from adenine, cytosine, guanine and uracil, and is constructed in such a manner that a number of bases which is not particularly limited, is generally 40, preferably 30 and more preferably about 20.

A symbol of $^{b}N1^{b}N2 \ldots {}^{b}Nn-1^{b}N$ indicates a base sequence corresponding to the guide-side target complementary region (14) of the 5'-target RNA [LA], and is constructed as a continuous base sequence which is constructed from combination of the same or different bases consisting of any base $^{b}N$ selected from adenine, cytosine, guanine and uracil, in such a manner that a number of bases is 1 to 15, preferably about 12, more preferably about 10, further preferably about 5.) is reacted with the 3'-target editing guide RNA [IIA] in FIG. 74 (in the formula, a symbol of $^{c}N1^{c}N2 \ldots {}^{c}Np-1^{c}Np$ corresponds to a guide-side decoupling region (27) of the 3'-target editing guide RNA, a symbol of $^{c}N$ is a base sequence constructed from the same or different bases selected from adenine, cytosine, guanine and uracil, and a symbol of p indicates a number of bases of generally 0 to 15, preferably 12 or less, more preferably 10 or less and further preferably about 5, and a symbol of $^dN \ldots {}^dNm$ indicates a base sequence constructing a terminal-side target recognition region (22) of the 3'-target editing guide RNA, is constructed as a continuous base sequence which is constructed from combination of the same or different bases consisting of any base $^dN$ selected from adenine, cytosine, guanine and uracil, in such a manner that a number of bases which is not particularly limited, is generally 40, preferably 30 and more preferably about 20, as well as the number is equal to a number of constituent base of the base sequence in the terminal-side target complementary region (12) of the 5-target RNA, and constructs base pairs with the base sequence of the terminal-side target complementary region.

a symbol of $^eN1^eN2 \ldots {}^eNn+p$ indicates a base sequence of X adjacent partial region of the core-side target recognition region represented by a symbol $^eN1^eN2 \ldots {}^eNn$ and a base sequence of ADAR adjacent partial region represented by $^eN1^eN2 \ldots {}^eNp$ as well as the X adjacent partial regions consisted of any bases of a symbol $^eN$ selected from adenine, cytosine, guanine and uracil, and indicates a continuous base sequence consisted of the same or different bases in a number of base which is not particularly limited as long as the object and function of the present invention are not impaired of generally 1 to 15, preferably 1 to 12, more preferably 1 to 10, and particularly preferably 5 oe less. The ADAR adjacent partial region indicates a continuous base sequence which is consisted of any bases selected from adenine, cytosine, guanine and uracil and a number of bases is generally 0 to 15, preferably 12 or less, and more preferably 10 or less.), to compose and obtain a 5'-target RNA-3'-target editing guide RNA complex [IIIA] in FIG. 75, and then the resulting 5'-target RNA-3'-target editing guide RNA complex [VIIIA] is A-I edited by the action of ADAR and converted to the 5'-edited target RNA [IVA] in FIG. 76, and the target base adenosine (A*) is converted to inosine (I). The resulting 5-edited target RNA [IVA] is converted the 5'-translated target RNA [VA] in FIG. 77 by subsequent translating its inosine (I) into guanosine (G).

However, in the 5'-target RNA [IA], the number marked with a solid triangle represents the number of bases of the base $^bN$ from the target base A. For example, the number 0 means that there is no base of the guide side target complementary region adjacent to the target base A, the number 1 means that one base of the guide side target complementary region adjacent to the target base A, and furthermore, the number n means a base sequence consisting of n bases of the guide side target complementary region adjacent to the target base A. It also has the same meaning in the following description.

Similarly, in the Y-target editing guide RNA [IIA], the number marked with 4 represents the number of bases of the base cN from one end of the ADAR binding core region. For example, the number 0 means that there is no base sequence of the guide side division region adjacent to the target base A, the number 1 means that there is one base in the guide side division region, and the number p means a base sequence consisting of p bases in the guiding side disruption region. It also has the same meaning in the following description.

In addition, in the 3'-target editing guide RNA [IIA], for example, when the number is 0, there is no base in the guide side divided region adjacent to one end of the ADAR binding core region, and then there is no base corresponding to the ADAR adjacent portion of the corresponding core side target recognition region. Therefore, in this case, the core side target recognition region is composed only of the base sequence of the X adjacent region represented by the symbol $^eN1 \ldots {}^eNn$. On the other hand, when the number is 1, since the number of bases in the guide side decoupling region is one, the base sequence of the core side target recognition region is represented by the symbol $^eN1 \ldots {}^eNn+1$. When the number is p, the base sequence of the core side target recognition region is represented by the symbol $^eN1 \ldots {}^eNn+p$. It also has the same meaning in the following description. For example, when the number is 1, that is, in the case of the symbol $^eN1$, the corresponding base $^eN1$ of the editing guide RNA composes a base pair with the base $^bN1$ of the target side complementary region of the target RNA.

If the number of constituent bases of the core side target recognition region of the editing guide RNA becomes too small so that the distance from the corresponding base (X) existing in the 3-target recognition region of the target edition guide RNA to the ADAR binding core region is too short, the induction capability of A-I editing by ADAR may decrease and it is not preferable. In addition, even if the number of constituent bases becomes too large and the distance from the corresponding base (X) present in the 3-target recognition region of the target editing guide RNA to the ADAR binding core region becomes too long, the induction capability of A-I editing may decreases and it is not preferable.

In addition, in the ADAR binding region, the symbol NαNβ-NδNχ consists of an incomplete double-stranded RNA structure consisting of a stem-loop structure which corresponds to the base sequence composing the ADAR binding core region (28, 68) of the 3-target editing guide RNA [LIA] and the 5'-target editing guide RNA [LVIA] as described above. That is, the stem-loop structure is composed of two base sequences with a loop structure interposed therebetween and the two base sequences have a structure composed of incompletely complementary double strands including complementary base pairs and mismatch base pairs. The base (N) constituting each single strand is composed of the same or different bases selected from adenine, cytosine, guanine and uracil, and a number of bases of each single strand is generally 10 to 40, and preferably 20 to 30. Also, in the loop structure, the corresponding constituent bases do not form complementary strands to each other and are composed from the same or different bases of 4 to 8, preferably 4 to 5. In this stem-loop structure, one terminal of the incomplete complementary double strand which interposes the loop structure and binds each other may be joined with a base sequence of the ADAR adjacent region of the target recognition region, and the other terminal may be joined with a base sequence of the guide-side decoupling region.

The symbol Nα-Nχ is composed of one base sequence each consisting of the same or different bases selected from adenine, cytosine, guanine and uracil, and this base pair represents an incomplete double-stranded complementary region with single or plural, preferably about two mismatched base pairs. The symbol Nβ-Nδ represents a loop structure composed of similar the same or different bases having 4 to 8, preferably 4 to 5 bases. Also, the symbol Nα-Nχ has a structure in which one terminal thereof is joined with the guide-side target complementary region of the 5'-target RNA or the guide-side decoupling region of the target editing guide RNA and the other terminal is joined with the core side target recognition region of the target editing guide RNA In the 5'-target RNA-3'-target editing guide RNA complex [IIIA], the symbols $^aN1 \ldots {}^aNm$ and the symbols $^dN1 \ldots {}^dNm$ are constituent base pairs (that is, for example, $^aN$-$^dN$), $^a$Nm-$^d$Nm) are shown in a state of being connected with a solid line, and each constituent base pair forms a complementary strand.

That is, the base sequence of the terminal-side target complementary region of the 5'-target RNA represented by the symbol $^a$N1 ... $^a$Nm and the base sequence of the terminal-side target recognition region of the 3'-target editing guide RNA represented by the symbol $^d$N1 ... $^d$Nm base pair with each other to form base pairs and the base sequence of the guide-side target complementary region of the 5'-target RNA represented by the symbols [$^b$N1 ... $^b$Nn] and the base sequence of the X-adjacent portion of the core side target recognition region of the 3-target editing guide RNA represented by the symbol [$^e$N1 ... $^e$Nn] base pair with each other to form a base pair and complex. On the other hand, the ADAR binding core region has a structure in which one terminal is joined with the base sequence of the guide side decoupling region and the other terminal is joined with the ADAR adjacent part of the core side target recognition region.

Similarly, the method for introducing a site-directed RNA mutation of the present invention by the second target editing scheme will be described more specifically with reference to FIG. 6. Each symbol in the figure has substantially the same meaning as the corresponding symbol in the first target editing scheme, so a detailed explanation will be omitted here in order to simplify the explanation.

According to the present invention, as in the case of the 3'-target editing guide RNA [IIA] in which the 5'-target RNA is complementary to the 5'-terminal portion, 3'-target RNA is complementary to the 3'-terminal portion at 3'-targeting guide RNA [IIA] as well, the target base adenosine of the 3'-target RNA undergoes A-I editing and is converted to inosine (I).

Figure 6:
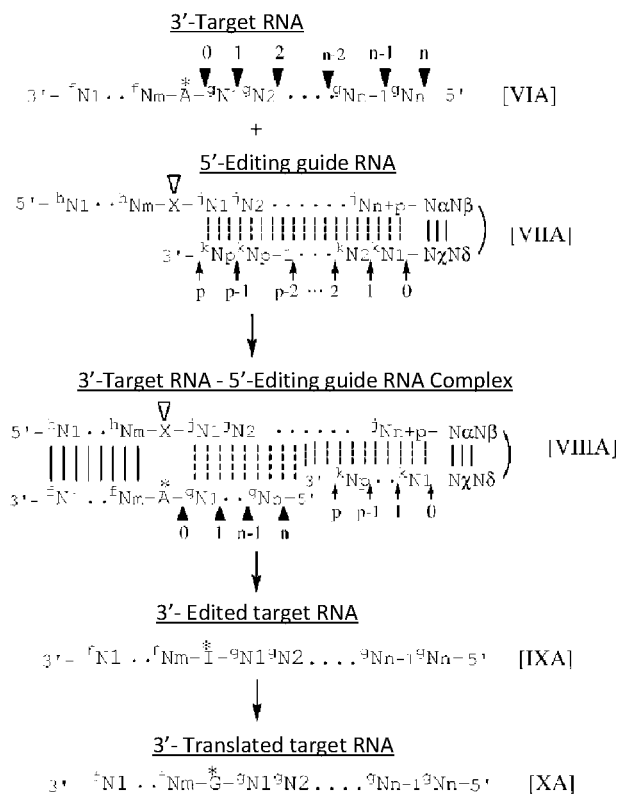
FIG. 6 is a scheme showing a method for introducing a site-directed RNA mutation according to a concrete embodiment of the second aspect of the present invention.

The method of the present invention of the method according to the second target editing scheme is composed by RNA mutation editing in which, as shown in FIG. 6, the 3'-target RNA [VIA] in FIG. 78, is reacted with the 5'-target editing guide RNA [VIIA] in FIG. 79, to compose and obtain the 5'-target RNA-3'-target editing guide RNA complex [VIIIA] in FIG. 80, and subsequently the resulting complex is induced A-I editing capability by the action of ADAR to convert to 5'-edited target RNA [IXA] in FIG. 81. In the resulting the 5'-edited target RNA, its inosine (I) is translated to guanosine to convert 5'-translated target RNA [XA] in FIG. 82.

In addition, in the first and second target editing schemes, an embodiment in which any of cytosine (C), guanosine (G), adenosine (A) or uridine (U) is disposed at the site (marked with triangle) corresponding to the target editing site (*) can be constructed. In view of inducing A-I editing capability, in general, since cytosine (C) is higher than others, as a preferred embodiment of the invention, an embodiment in which the corresponding base (X) is cytosine (C) can be constructed. This also applies to the following.

Figure 7:
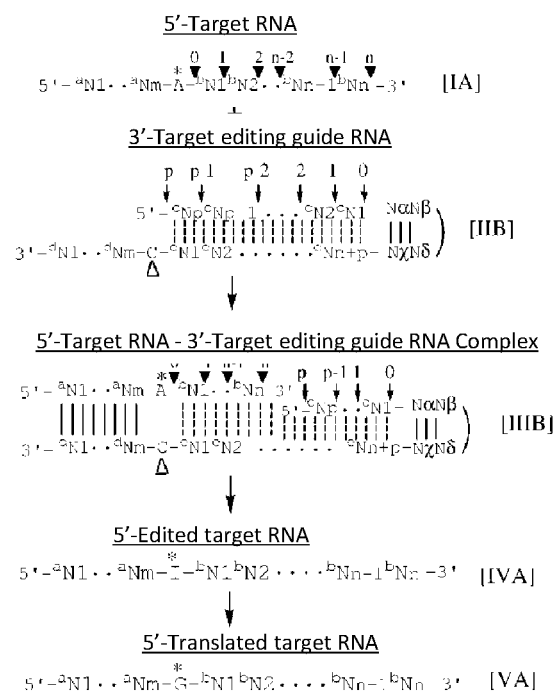
FIG. 7 is a scheme showing a method for introducing a site-directed RNA mutation according to a more concrete embodiment of the first aspect of the present invention.

Therefore, in the first target editing scheme, the present invention provides the method for introducing a site-directed RNA mutation in which, as shown in FIG. 7, the 3'-target editing guide RNA [IIA] is used in place of the 3'-target editing guide RNA [IIB] in FIG. 83, to compose with the 5-target RNA and to obtain the 5'-target RNA-the 3-target editing guide RNA complex [IIIB] in FIG. 84, and the target base adenosine of the 5'-target RNA is A-I edited to convert inosine.

Figure 8:
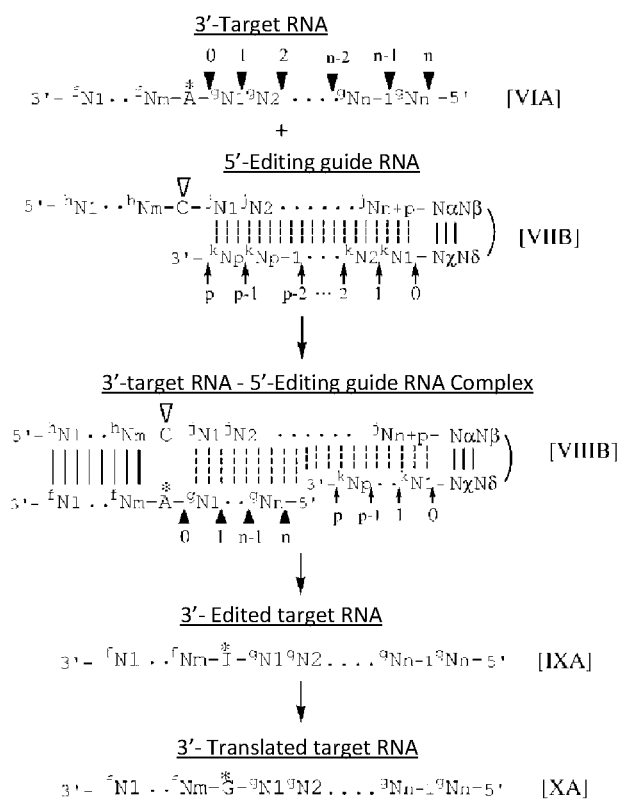
FIG. 8 is a scheme showing a method for introducing a site-directed RNA mutation according to a more concrete embodiment of the second aspect of the present invention.
Figure 85:
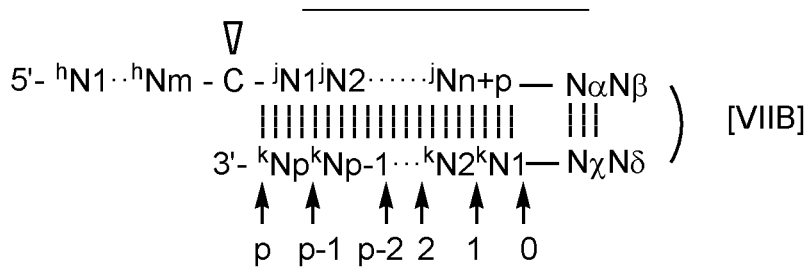
FIG. 85 is a 5'-target editing guide RNA [VIIB].
Figure 86:
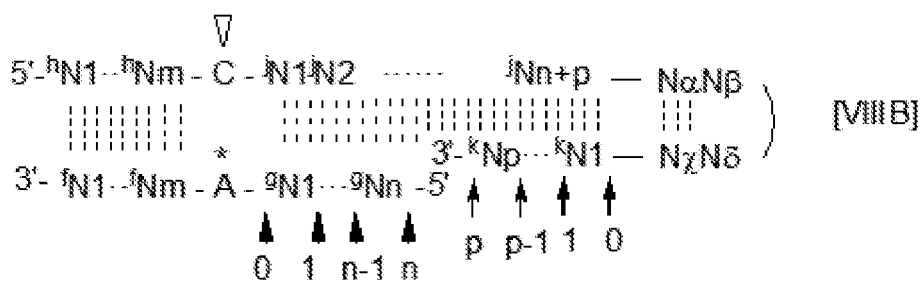
FIG. 86 is a 3'-target RNA-5'-target editing guide RNA complex [VIIIB].

Similarly, the present invention according to the second target editing scheme provides the method for introducing a site-directed RNA mutation in which, as shown in FIG. 8, the 5'-target editing guide RNA [VIIA] is used in place of the 5-target editing guide RNA [VIIB] in FIG. 85 to compose with the 3-target RNA and to obtain the 3-target RNA-5'-target editing guide RNA complex [VIIIB] in FIG. 86, and the target base adenosine of the 5-target RNA is A-I edited to convert inosine.

Furthermore, in the first and second target editing schemes, the present invention can construct a preferred embodiment using a full-length RNA molecule or a partial length RNA molecule including a target RNA fragment as the target RNA.

Figure 9:
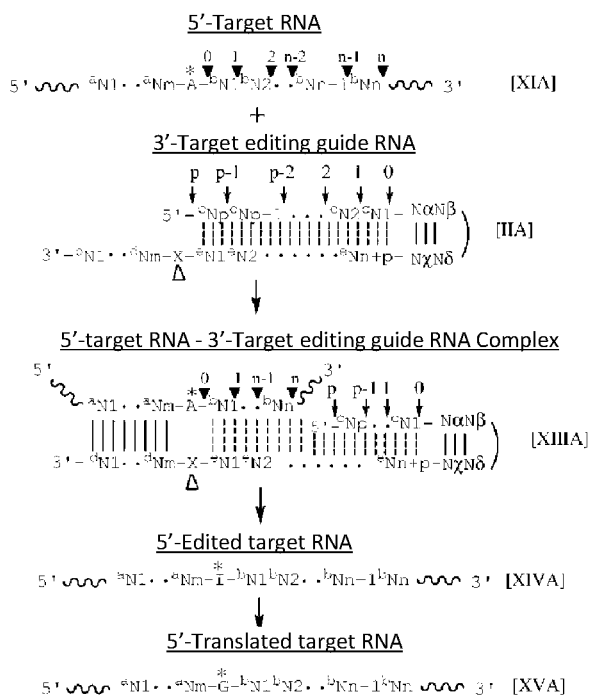
FIG. 9 is a scheme showing a method for introducing a site-directed RNA mutation according to another concrete embodiment of the first aspect of the present invention.
Figure 87:
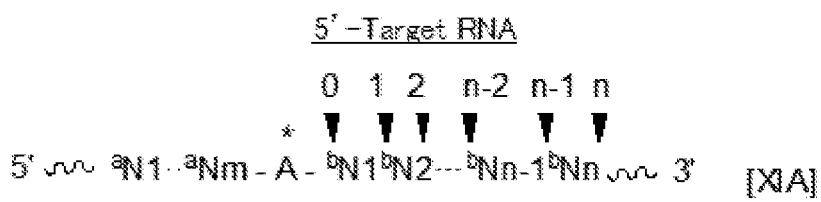
FIG. 87 is a 5'-target RNA [XIA].
Figure 88:
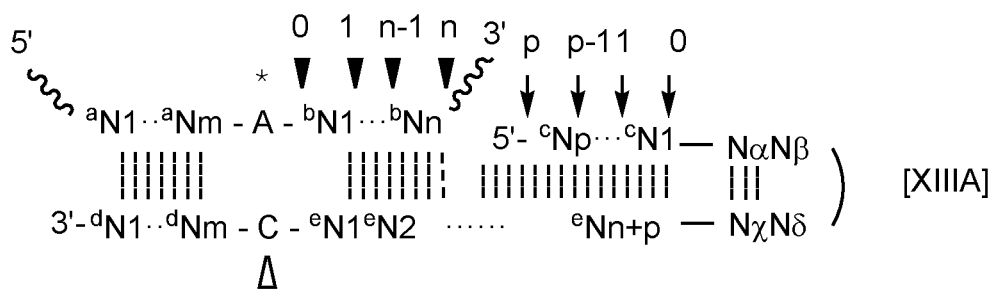
FIG. 88 is a 5'-target RNA-3'-target editing guide RNA complex [XIIIA].

That is, the present invention of the method for introducing a site-directed RNA mutation according to the first target editing scheme provides the method for introducing a site-directed RNA mutation in which, as shown in FIG. 9, in place of the 5'-target RNA [IA], 5'-target RNA [XIA] in FIG. 87, is used to compose with the 3'-target editing guide RNA and to obtain the 5'-target RNA-3'-target editing guide RNA complex [XIIIA] in FIG. 88, and the target base adenosine of the 5'-target RNA is A-I edited to convert inosine.

Figure 10:
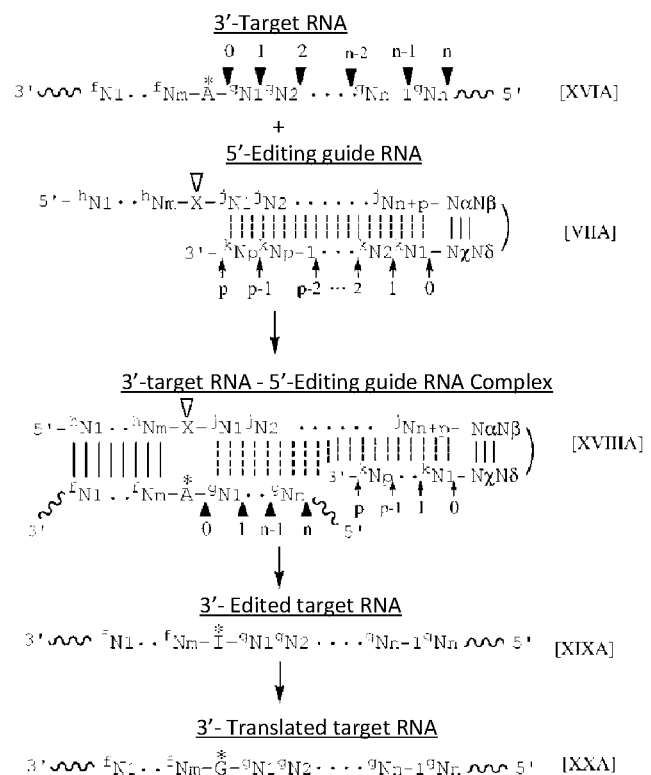
FIG. 10 is a scheme showing a method for introducing a site-directed RNA mutation according to another concrete embodiment of the second aspect of the present invention.
Figure 89:
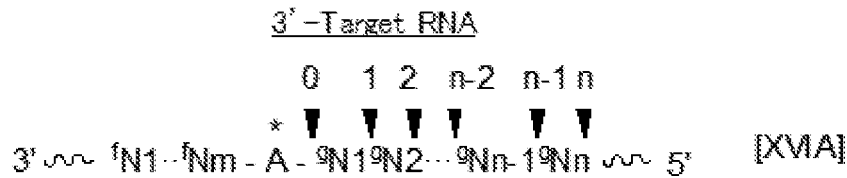
FIG. 89 is a 3'-target RNA [VIA], 3'-target RNA [XVIA].
Figure 90:
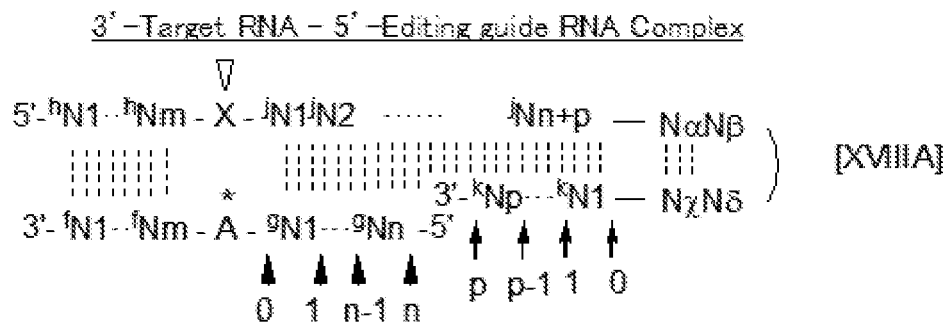
FIG. 90 is a 3'-target RNA-5'-target editing guide RNA complex [XVIIIA].

In addition, the present invention of the method for introducing a site-directed RNA mutation according to the second target editing scheme provides the method for introducing a site-directed RNA mutation in which, as shown in FIG. 10, in place of the 3-target RNA [VIA], 3-target RNA [XVIA] in FIG. 89, is used to compose with 5-target editing guide RNA and to obtain the 3'-target RNA-5'-target editing guide RNA complex [XVIIIA] in FIG. 90, and A-I editing capability is induced by the action of ADAR and the target base adenosine of the 5'-target RNA is A-I edited to convert inosine.

In both of the first and second target editing schemes, the converted inosine present at the target site is translated into guanosine.

Figure 11:
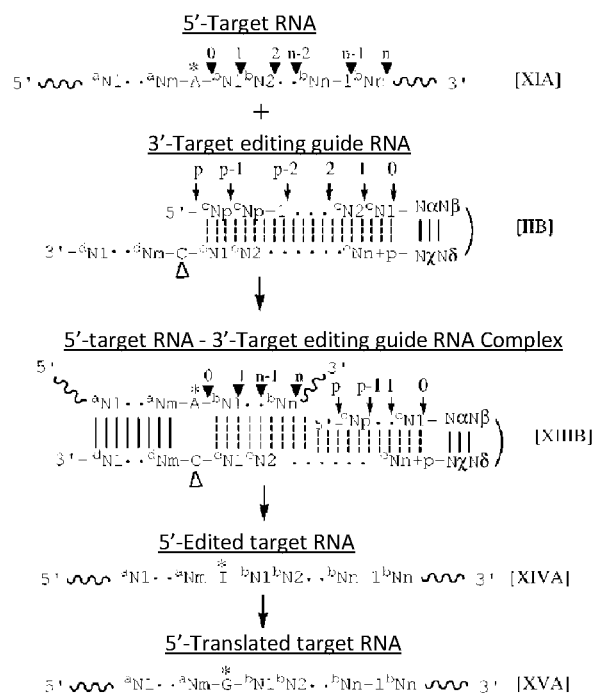
FIG. 11 is a scheme showing a method for introducing a site-directed RNA mutation according to another preferred concrete embodiment of the first aspect of the present invention.
Figure 12:
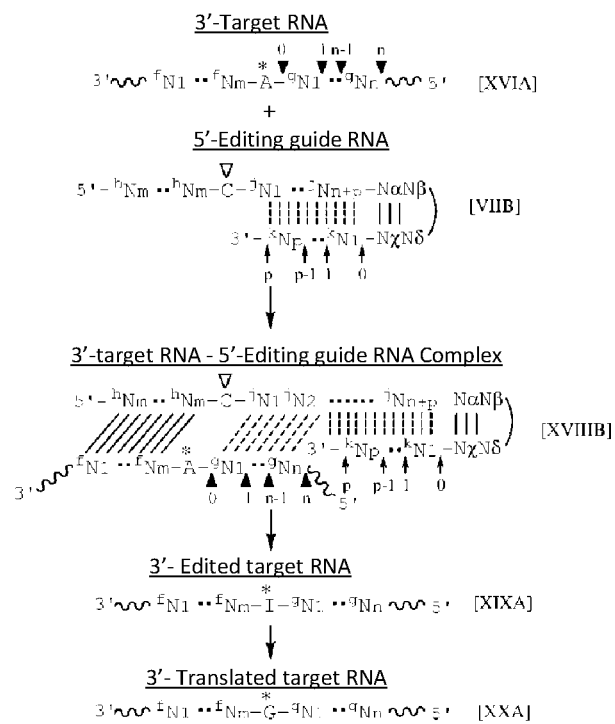
FIG. 12 is a scheme showing a method for introducing a site-directed RNA mutation according to another preferred concrete embodiment of the second aspect of the present invention.
Figure 91:
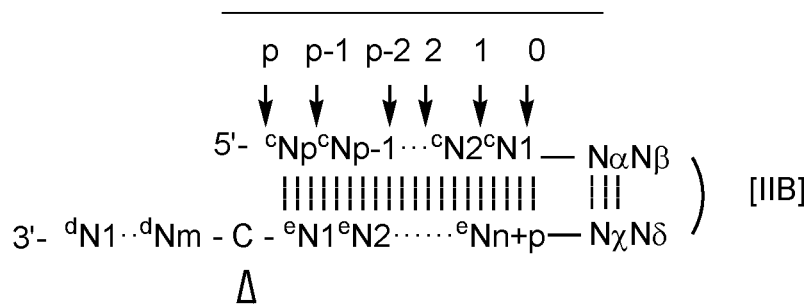
FIG. 91 is a 3'-target editing guide RNA [IIB].
Figure 92:
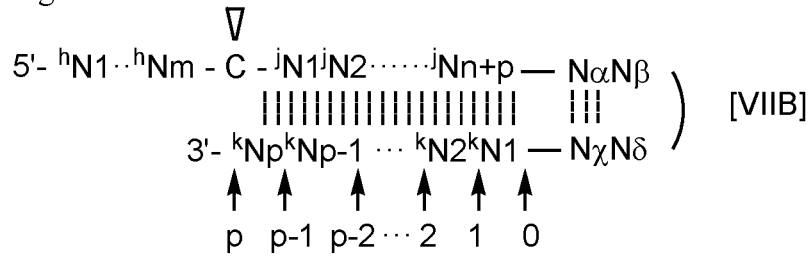
FIG. 92 is a 3'-target editing guide RNA [VIIB].
Figure 93:
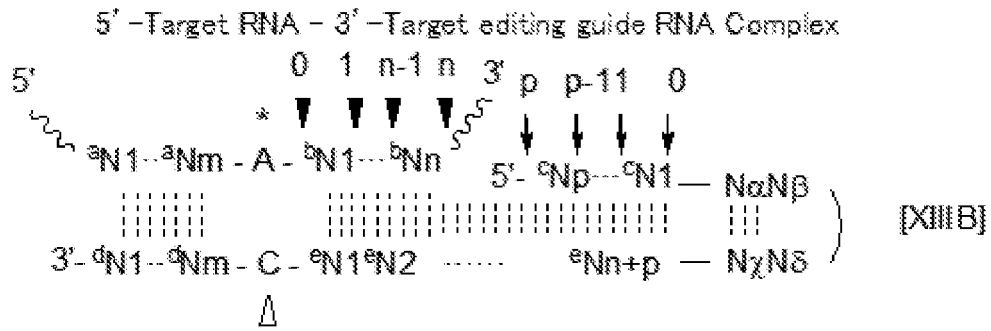
FIG. 93 is a 5'-target RNA-3'-target editing guide RNA complex [XIIIB].
Figure 94:
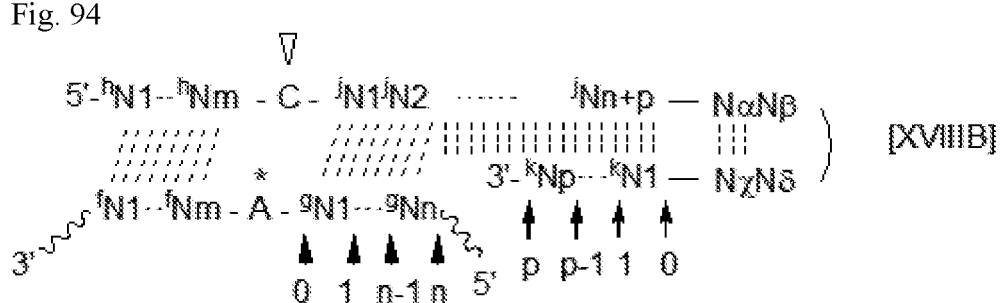
FIG. 94 is a 3'-target RNA-5'-target editing guide RNA complex [XVIIIB].

In the above target editing scheme, by constructing the RNA base (X) present in the site corresponding to the target editing site to cytosine (C), the present invention according to the first and second target editing schemes provides the method for introducing a site-directed RNA mutation in which, as shown in FIGS. 11 and 12, in place of 3-target editing guide RNA [IIA], 3'-target editing guide RNA [IIB] in FIG. 91, or in place of the 5'-target editing guide RNA [VIIA], 3-target editing guide RNA [VIIB] in FIG. 92, is used to compose with the 5-target RNA [XIA] or the 3-target RNA [XVIA] and to obtain the 5-target RNA-3'-target editing guide RNA complex [XIIIB] in FIG. 93, or the 3'-target RNA-5'-target editing guide RNA complex [XVIIIB] in FIG. 94, and A-I editing capability is induced by the ADAR action on the resulting complex and the target base adenosine of the target RNA is converted to inosine, and then inosine is translated into guanosine.

The target editing guide RNA including the ADAR binding region used in the present invention can be designed as follows. As described above, Non-Patent Document 7 describes that, based on the glutamate receptor mRNA precursor (GluR-B pre-mRNA) (Non-Patent Document 6) which is specifically edited in vivo by ADAR2, the editing substrate RNA (miniSL RNA) leaving only the region necessary for editing has been constructed. The present inventor has found that it can be constructed as the target editing guide RNA of the present invention by separating the target editing guide RNA and the target RNA by leaving only the ADAR binding region of this editing substrate and dividing at the position shown in the figure. Therefore, since the target editing guide RNA constructed in this way has a complementary region for recognizing the target RNA in addition to the ADAR binding region, it can be applied to any target RNA, so it can be used as a target editing guide of the present invention.

Figure 95:
FIG. 95 is a glutamate receptor mRNA precursor (GluR-B pre-mRNA) [XLVIIA].
Figure 96:
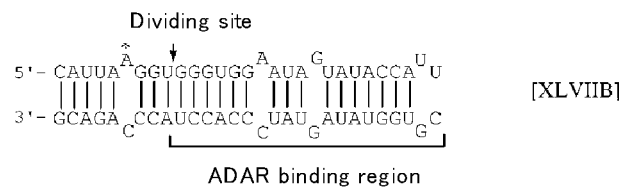
FIG. 96 is a editing substrate (miniSL RNA) [XLVIIB].

Specifically, in the present invention, the target editing guide RNA was designed for green fluorescent protein mRNA sequence as a model target RNA, and it was confirmed whether A-I mutation can be induced at the target editing site. Therefore, after designing each of RNAs using in vitro transcription reaction, in vitro editing reaction was carried out using purified recombinant ADAR2. As a result, it was found that the editing site was edited depending on the target editing guide RNA. As a result, it was found that target editing guide RNA having the intended function of the present invention can be constructed by such a design That is, for example, based on the glutamate receptor mRNA precursor (GluR-B pre-mRNA) [XLVIIA] (SEQ ID NO: 100) in FIG. 95, leaving only the ADAR binding region necessary for editing enables to construct an editing substrate (miniSL RNA) [XLVIIB] (SEQ ID NO: 101) in FIG. 96. In other words, it was revealed that this was able to separate into the target RNA and the target editing guide RNA as a result of splitting at the division site (4) leaving the ADAR binding region of the editing substrate RNA (miniSL RNA).

Figure 13:
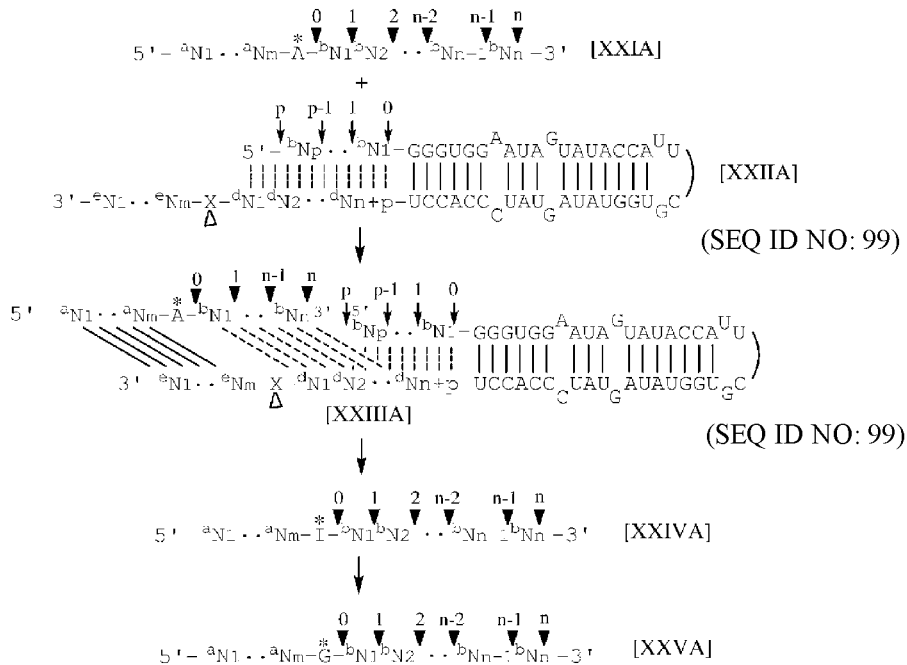
FIG. 13 is a scheme showing a method for introducing a site-directed RNA mutation according to a specific embodiment of the first aspect of the present invention.
Figure 97:
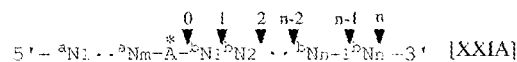
FIG. 97 is a 5'-target RNA [XXIA].
Figure 98:
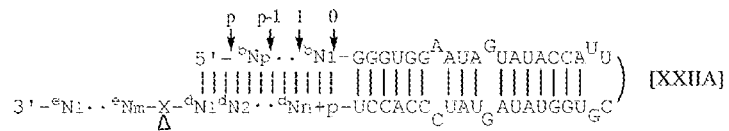
FIG. 98 is a 3'-target editing guide RNA [XXIIA].
Figure 99:
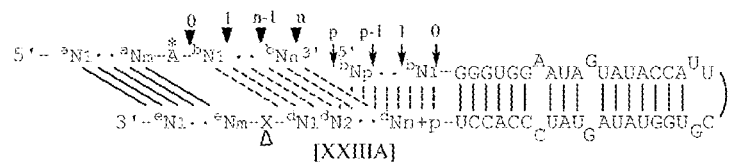
FIG. 99 is a 5'-target RNA-3'-target editing guide RNA complex [XXIIIA].
Figure 100:
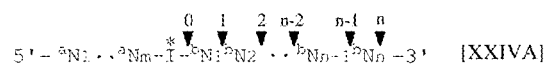
FIG. 100 is a 5'-edited target RNA [XXIVA].

Thus, a preferred embodiment of the present invention according to the first target editing scheme using the target editing guide obtained here is, as shown in FIG. 13, a method in which 5-target RNA [XXIA] in FIG. 97 is reacted with the 3-target editing guide RNA [XXIIA] (SEQ ID NO: 99) in FIG. 98, to compose and obtain the 5'-target RNA-3'-target editing guide RNA complex [XXIIIA] (SEQ ID NO: 99) in FIG. 99, and A-I editing capability is induced by ADAR action on the complex to convert to 5'-edited target RNA [XXIVA] in FIG. 100, and target base adenosine is converted to inosine. The converted inosine is translated into guanosine.

Figure 15:
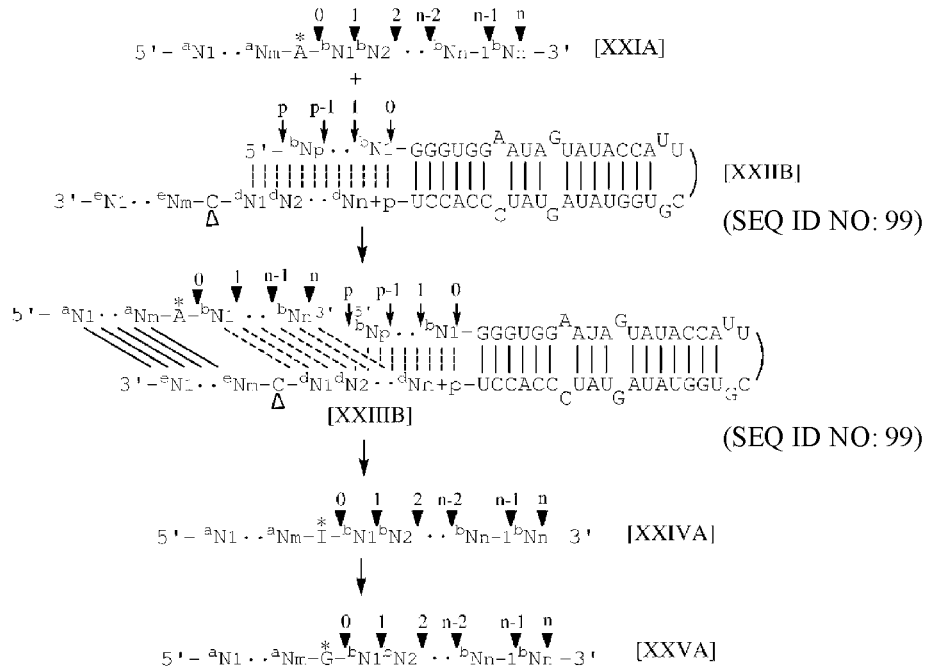
FIG. 15 is a scheme showing a method for introducing a site-directed RNA mutation according to another specific embodiment of the first aspect of the present invention.
Figure 101:
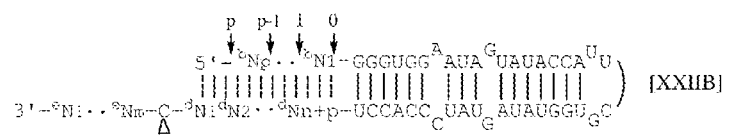
FIG. 101 is a 3'-target editing guide RNA [XXIIB].
Figure 102:
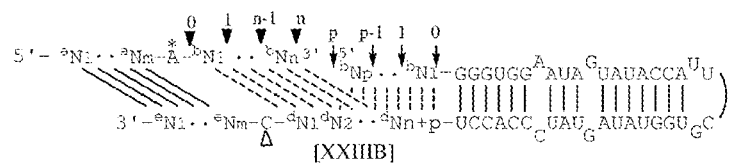
FIG. 102 is a 5'-target RNA-3'-target editing guide RNA complex [XXIIIB].
Figure 103:
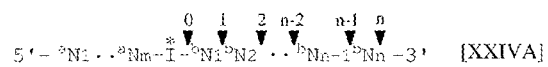
FIG. 103 is a 5'-edited target RNA [XXIVA].
Figure 104:
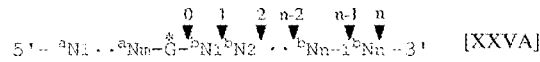
FIG. 104 is a 5'-edited target RNA [XXVA].

A more preferred embodiment of the present invention according to the first target editing scheme is, as shown in FIG. 15, as the 3'-target editing guide RNA [XXIIA], the 3'-target editing guide RNA [XXIIB] (SEQ ID NO: 99) in FIG. 101 is used and is reacted with the 5'-target RNA [XXIA] to compose and to obtain the 5'-target RNA-3'-target editing guide RNA complex [XXIIIB] (SEQ ID NO: 99) in FIG. 102, and A-I editing capability is induced by ADAR action, as shown in the 5'-edited target RNA [XXIVA] in FIG. 103, and the target base adenosine is converted to inosine. Such converted inosine is, as shown in 5'-edited target RNA [XXVA] in FIG. 104, translated into guanosine.

Figure 14:
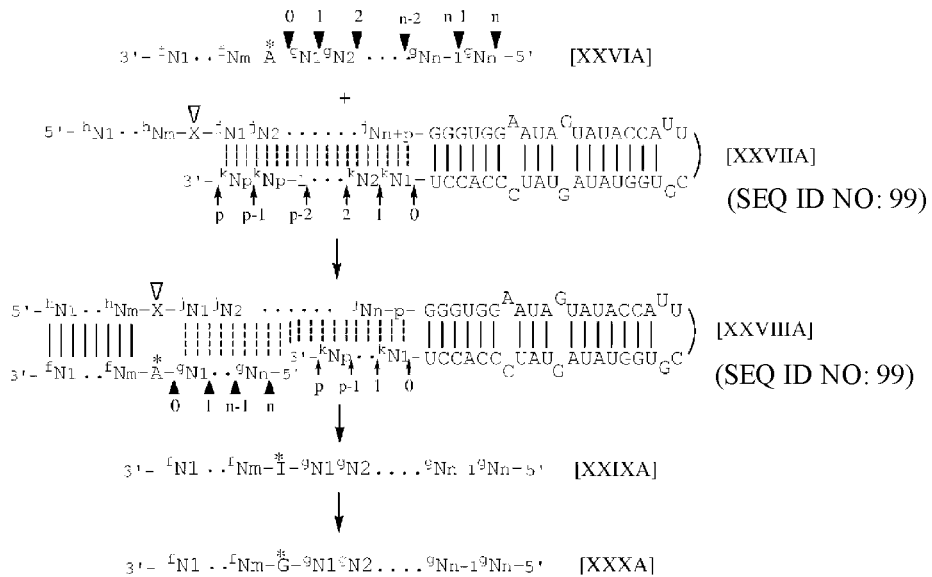
FIG. 14 is a scheme showing a method for introducing a site-directed RNA mutation according to a specific embodiment of the second aspect of the present invention.
Figure 105:
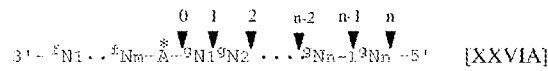
FIG. 105 is a 3'-target RNA [XXVIA].
Figure 106:
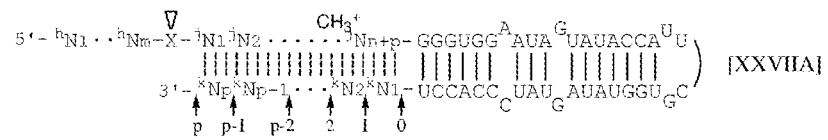
FIG. 106 is a 5'-target editing guide RNA [XXVIIA].
Figure 107:
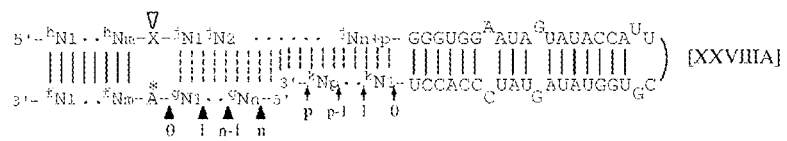
FIG. 107 is a 3'-target RNA-the 5'-target editing guide RNA complex [XXVIIIA].
Figure 108:
FIG. 108 is a 5'-edited target RNA [XXIXA].
Figure 109:
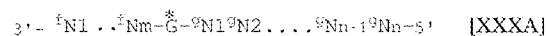
FIG. 109 is a 3'-translated target RNA [XXXA].

In addition, a more preferred embodiment of the present invention according to the second target editing scheme is, as shown in FIG. 14, the 3'-target RNA [XXVIA] in FIG. 105 is reacted with the 5'-target editing guide RNA [XXVIIA] (SEQ ID NO: 99) in FIG. 106, to compose and to obtain the 3'-target RNA-the 5'-target editing guide RNA complex [XXVIIIA] (SEQ ID NO: 99) in FIG. 107, and A-I editing capability is induced by ADAR action on the resulting complex to convert the 5'-edited target RNA [XXIXA] in FIG. 108, and the target base adenosine can be converted to inosine. Such converted inosine is, as shown in the 3'-translated target RNA [XXXA] in FIG. 109, translated into guanosine.

Figure 16:
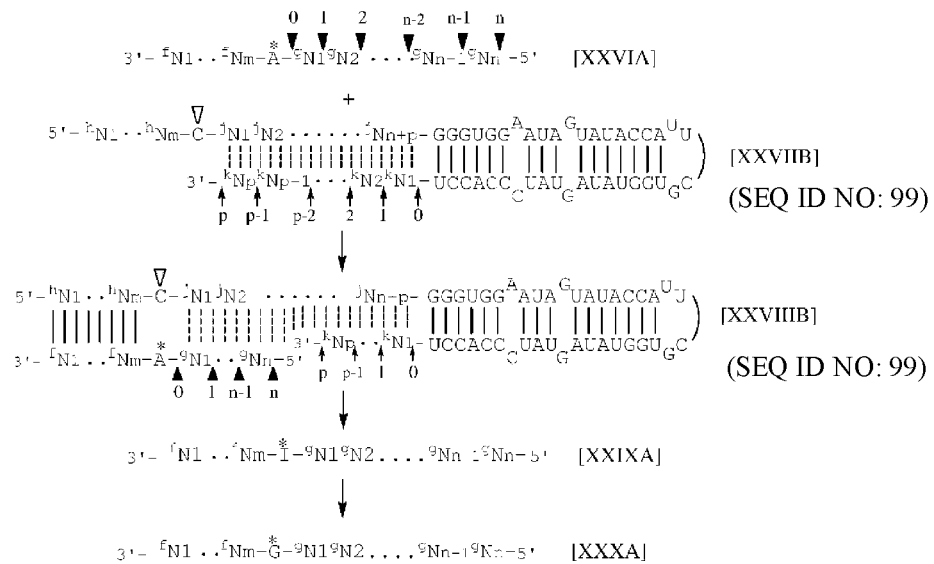
FIG. 16 is a scheme showing a method for introducing a site-directed RNA mutation according to another specific concrete embodiment of the second aspect of the present invention.
Figure 110:
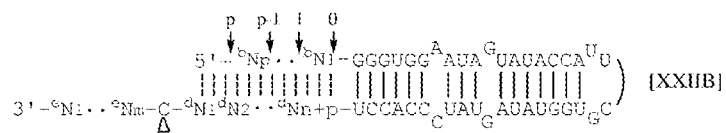
FIG. 110 is a 3'-target RNA [XXIIB].
Figure 111:
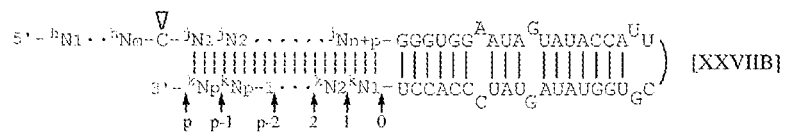
FIG. 111 is a 5'-target RNA [XXVIIB].
Figure 112:
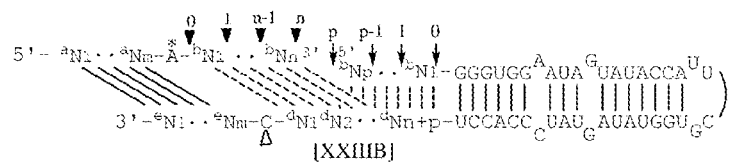
FIG. 112 is a 5'-target RNA-3'-target editing guide RNA complex [XXIIIB].
Figure 113:
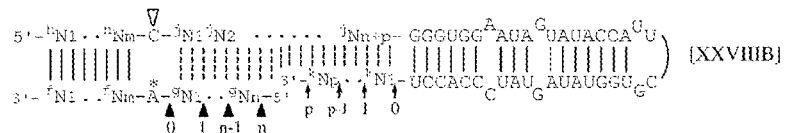
FIG. 113 is a 3'-target RNA-5'-target editing guide RNA complex [XXVIIIB].
Figure 114:
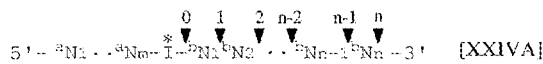
FIG. 114 is a 5'-edited target RNA [XXIVA].
Figure 115:
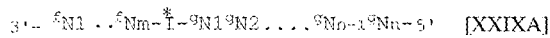
FIG. 115 is a 3'-edited target RNA [XXIXA].

Further, a more preferred embodiment of the present invention can be constructed by introducing cytosine into the corresponding site (marked with triangle) of the target editing site (*). That is, more preferred embodiment of the present invention is, as shown in FIG. 15 or 16, as the 3'-target editing guide RNA [XXIIA], the 3'-target RNA [XXIIB] (SEQ ID NO: 99) in FIG. 110, or, as the 5'-target editing guide RNA [XXVIIA], the 5'-target RNA [XXVIIB] (SEQ ID NO: 99) in FIG. 111, is used and reacted with the 5'-target RNA [XXIA] or the 3'-target RNA [XXVIA] respectively, to compose and to obtain the 5'-target RNA-3'-target editing guide RNA complex [XXIIIB] (SEQ ID NO: 99) in FIG. 112, or the 3'-target RNA-5'-target editing guide RNA complex [XXVIIIB] (SEQ ID NO: 99) in FIG. 113, and A-I editing capability is induced by ADAR action on the resulting complex to convert the 5'-edited target RNA [XXIVA] in FIG. 114, or the 3'-edited target RNA [XXIXA] in FIG. 115, and the target base adenosine can be converted to inosine. In each case, converted inosine is translated into guanosine.

Figure 17:
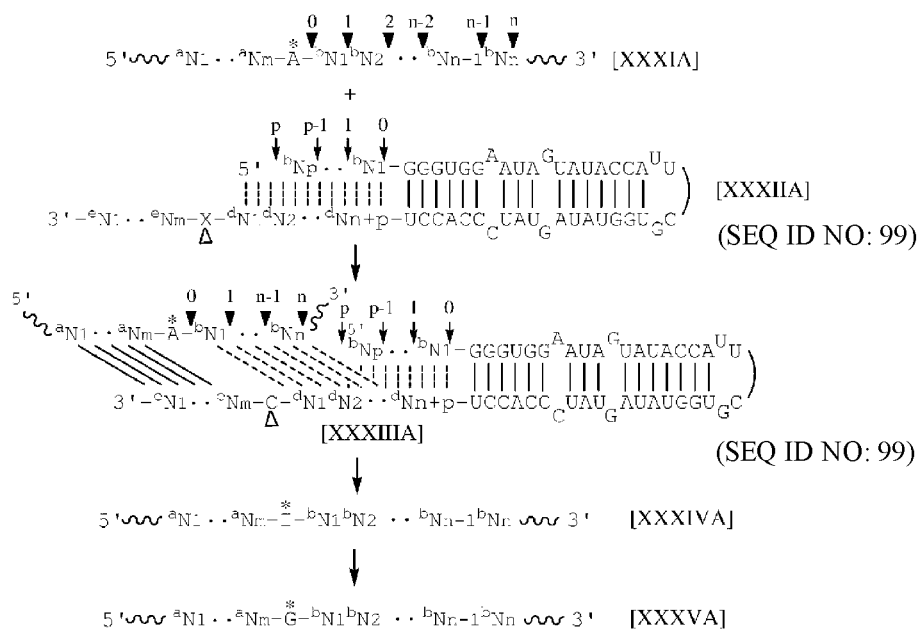
FIG. 17 is a scheme showing a method for introducing a site-directed RNA mutation according to another specific concrete embodiment of the first aspect of the present invention.
Figure 18:
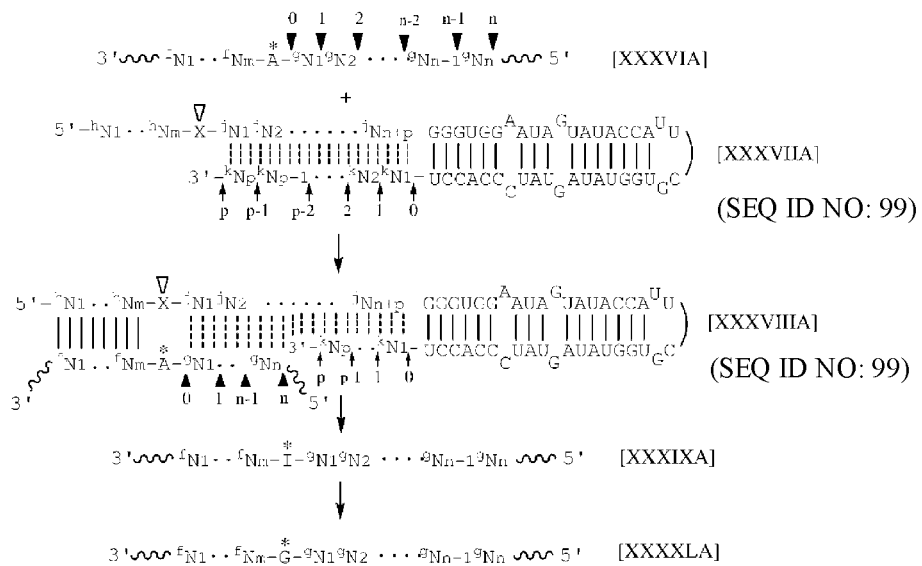
FIG. 18 is a scheme showing a method for introducing a site-directed RNA mutation according to another specific concrete embodiment of the second aspect of the present invention.
Figure 116:
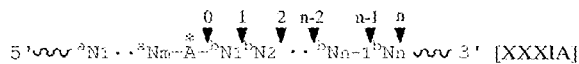
FIG. 116 is a 5'-target RNA [XXXIA].
Figure 117:
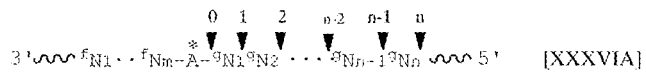
FIG. 117 is a 3'-target RNA [XXXVIA].

In the above first and second target editing schemes, in the present invention, the full-length RNA or the partial length RNA having the 5-target RNA [XXIA] or the 3'-target RNA [XXVIA] as specific regions in the RNA molecule can be used as a matter of course. Thus, in the present invention in this form, as shown in FIG. 17 or FIG. 18, the 5'-target RNA [XXXIA] in FIG. 116 as the 5'-target RNA [XXIA], or the 3'-target RNA [XXXVIA] in FIG. 117 as the 3-target RNA [XXVIA] is used and is composed with the 5'-target editing guide RNA [XXXIIA] or the 3'-target editing guide RNA [XXXVIIA] to obtain the 3'-target RNA-5'-target editing guide RNA complex [XXXIIIA] or the 5'-target RNA-3-target editing guide RNA complex, and A-I editing capability is induced by ADAR action on the resulting complex to convert the 5'-edited target RNA [XXXIVA] or the 3'-edited target RNA [XXXIXA], the target base adenosine is converted to inosine respectively, and then converted to the 5-translated target RNA [XXXVA] or the 3'-translated target RNA [XXXLA] and inosine is translated into guanosine, respectively.

Further, in the first and second target editing schemes, by changing the base (X) at the site corresponding to the target editing site to RNA base cytosine, a method according to a more preferred embodiment of the present invention is provided.

Figure 19:
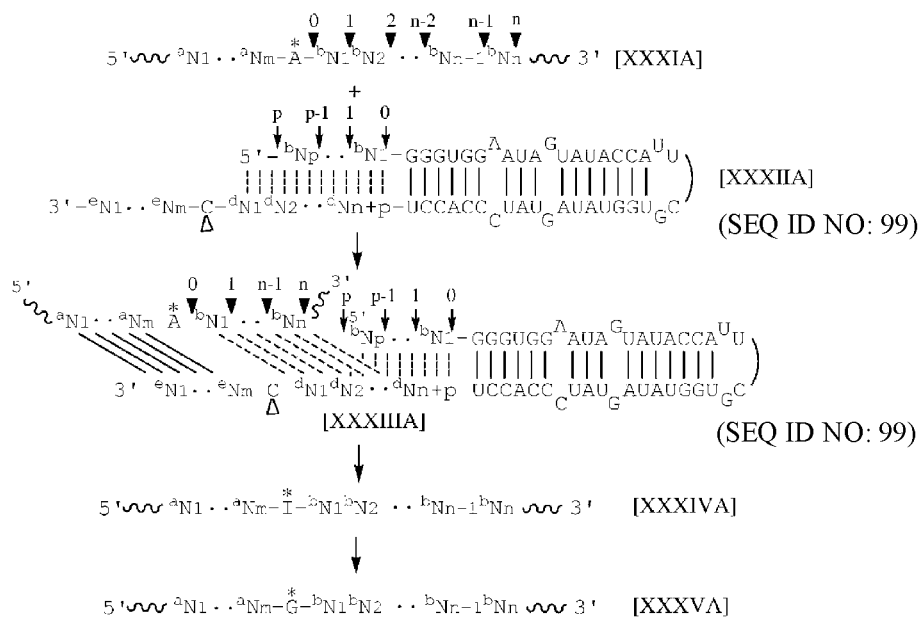
FIG. 19 is a scheme showing a method for introducing a site-directed RNA mutation according to another specific concrete embodiment of the first aspect of the present invention.
Figure 20:
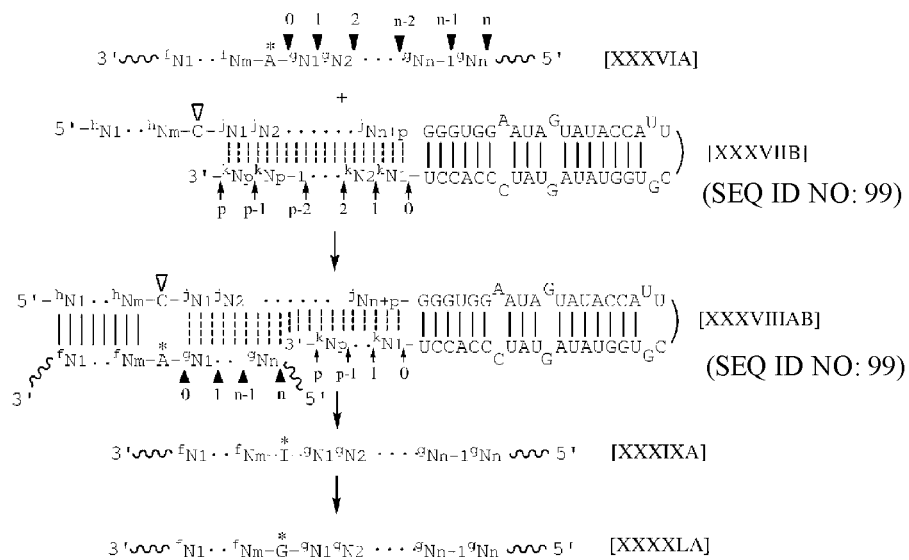
FIG. 20 is a scheme showing a method for introducing a site-directed RNA mutation according to another specific concrete embodiment of the second aspect of the present invention.

That is, in a more preferred embodiment of the present invention, as shown in FIG. 19 or FIG. 20, the 5'-target RNA [XXXIA] or the 3-target RNA [XXXVIA] is reacted with the 3-target editing guide RNA [XXXIIA] or 5'-target editing guide RNA [XXXVIIA], respectively to obtain the 5-target RNA-3'-target editing guide RNA complex or the 3-target RNA-S-target editing guide RNA complex, and A-I editing capability is induced by ADAR action on the resulting complex to convert the 5'-edited target RNA [XXXIVA] or the 3-edited target RNA [XXXIXA], the target base adenosine is converted to inosine respectively, and then converted to the 5-translated target RNA [XXXVA] or the 3-translated target RNA [XXXLA] and inosine is translated into guanosine, respectively.

Figure 118:
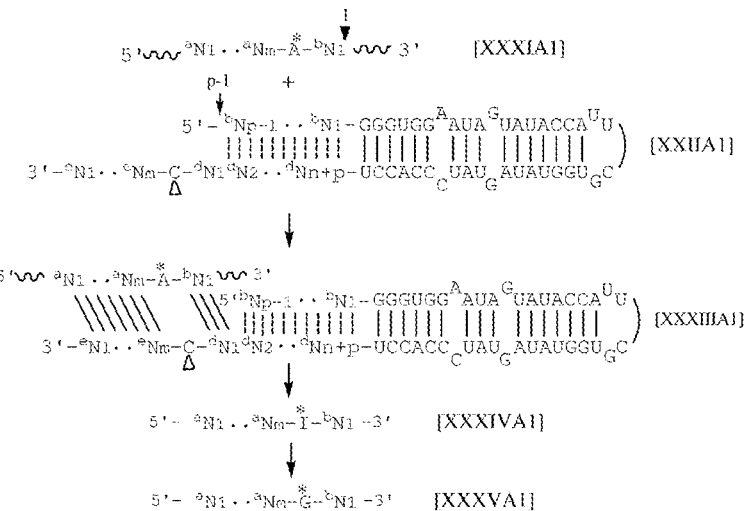
FIG. 118 is a first target editing scheme to convert the target base adenosine of the target RNA to inosine.
Figure 119:
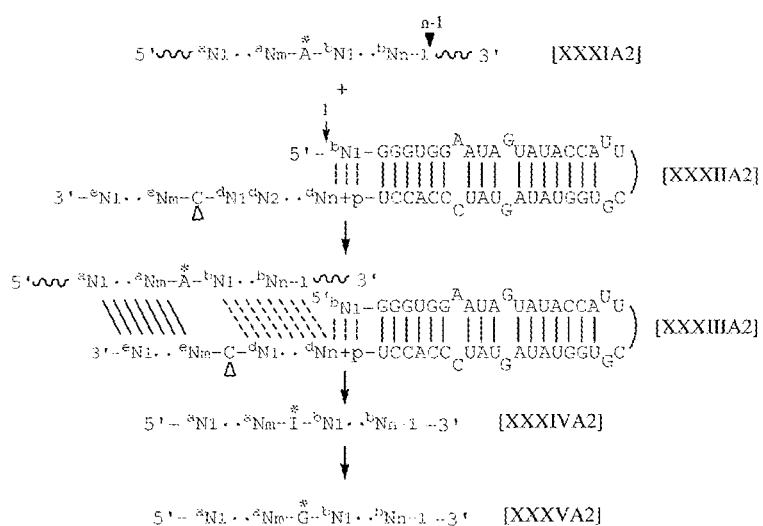
FIG. 119 is a first target editing scheme to convert the target base adenosine of the target RNA to inosine.

Furthermore, a more preferred embodiment of the present invention according to the first target editing scheme is a method in which, for example, by using RNA molecules divided at each site of the target RNA (marked with solid triangle) and the target editing guide RNA divided at each site corresponding thereto (the arrows position), it is possible to convert the target base adenosine of the target RNA to inosine shown in FIGS. 118 and 119. Other embodiments can be similarly applied.

Figure 120:
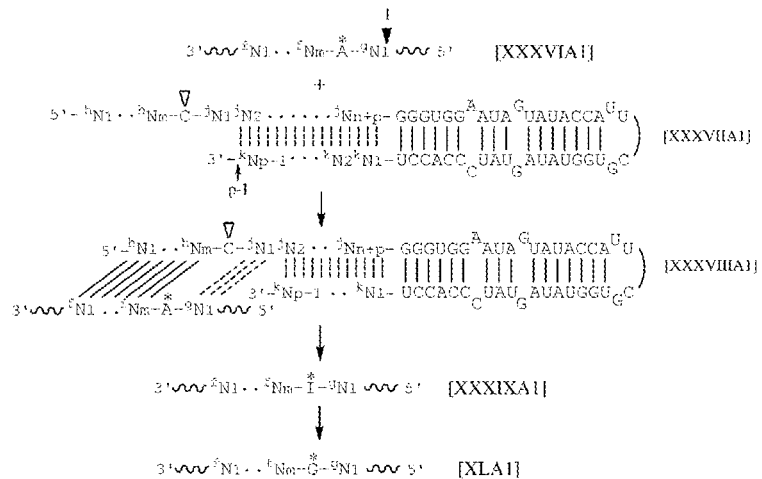
Figure 121:
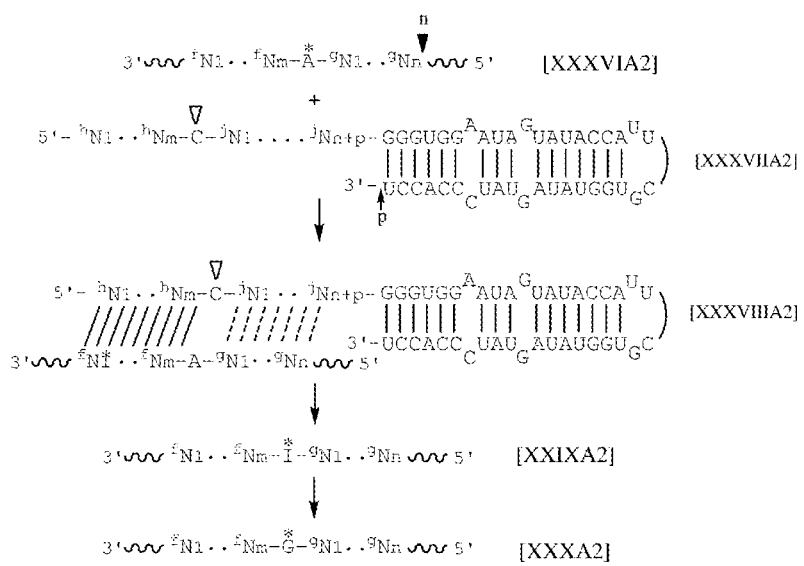

Similarly, by dividing at each site of the target RNA (marked with solid triangle), a more preferred embodiment of the present invention according to the second target editing scheme can be obtained as follows in FIGS. 120 and 121. Other embodiments can be similarly applied Here, an actual model in the present invention will be described. In the present invention, the target editing guide RNA was designed for green fluorescent protein mRNA sequence as a model target RNA, and it was confirmed whether A-I mutation can be induced at the target editing site. After each designed RNAs was synthesized by using in vitro transcription reaction, in vitro editing reaction was carried out using purified recombinant ADAR2. As a result, it became clear that the editing site is edited depending on the target editing guide RNA.

Figure 122:
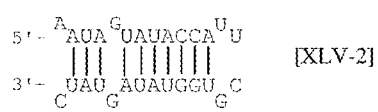

Therefore, when the above-mentioned editing substrate [XLVIIB] is divided by shifting the dividing site one by one, an ADAR binding core region composed of a double strand having the following sequence can be constructed shown in FIG. 122 (SEQ ID NO. 102).

Therefore, the target editing guide of the present invention can be constructed by binding the target recognition region and the base sequence of the guide-side decoupling region to both ends of the ADAR binding core region, respectively.

Figure 123:
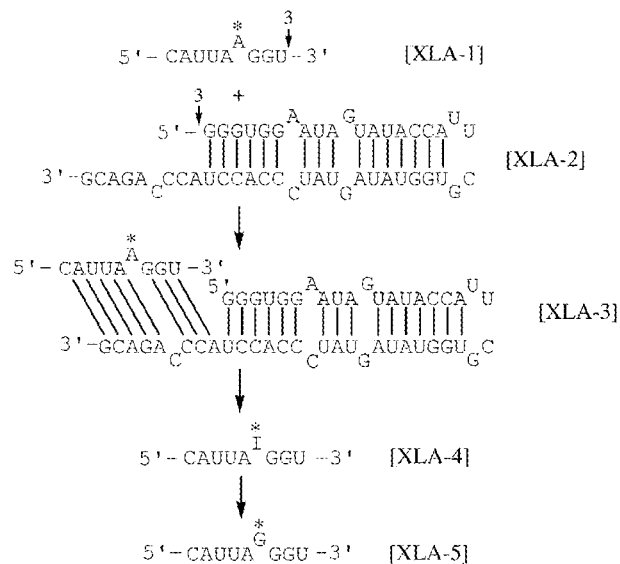

For example, an editing substrate (for example, MiniSL RNA [XLA]) including a target editing site (*) is divided into a region including the target editing site and an ADAR binding region at the dividing site (for example, each of arrows 0 to 9 Site), and it can be separated into the target RNA and the target editing guide RNA, respectively. For example, in the case of dividing at the position of the arrow 3, the target editing scheme of the present invention can be expressed as follows in FIG. 123.

Figure 124:
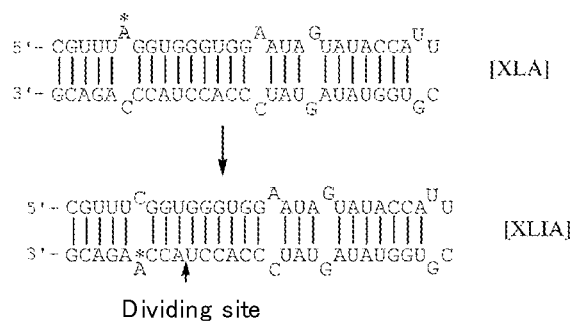

Even when the 3'-target RNA is used, the target base adenosine is converted to inosine as in the case of the 5'-target RNA. Here, an editing substrate (miniSLr RNA) [XLIA] (SEQ ID NO: 105) designed by exchanging the target editing site of the editing substrate (miniSL RNA) [XLA] (SEQ ID NO: 104) will be described as an example in FIG. 124.

For example, when the editing substrate [XLVA] is divided at the sites (0 to 5) indicated by arrows, as shown in the following formulae, the 5'-target editing guide RNAs [XLVA-0] to [XLVA-5] and the 3'-target RNAs [XLVIA-0] to [XLVIA-5] are formed, respectively in FIGS. 125 and 126. In the illustrated editing substrate, it is possible to divide at a site other than the segmented site shown in the drawing, that is, all of the complementary regions (nine bases present on the 5' side of A) leaving the ADAR binding core region, RNA and target editing guide RNA can be separated.

These target RNAs complement each of the above-described target editing guide RNAs [XLVA-0] to [XLVA-5] to form a complex, and the A-I editing capability is induced by the action of ADAR, so that the target base adenosine is converted to inosine, respectively.

Figure 127:
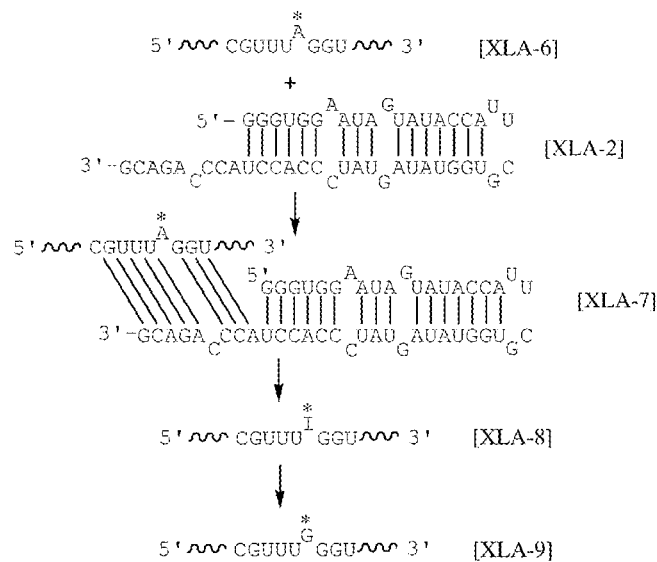

These target editing guide RNAs are naturally complexed complementarily to full-length RNA or partial length RNA containing the corresponding respective target RNA, and the target base adenosine is converted to inosine by the action of ADAR. For example, when the target editing guide RNA [XLA-2] divided by arrow 3 is used, it is complementary to the full-length RNA or partial length RNA [XLA-6] containing the corresponding target RNA [XLA-1] to form the 5'-target RNA-3'-target editing guide RNA complex [XLA-7], then induced A-I editing capability by the action of ADAR to convert to the 5'-edited target RNA [XLA-8] and target bases adenosine is converted to inosine as shown in FIG. 127. The inosine of this edited target RNA is translated into guanosine and converted into the 5'-translated target RNA [XLA-9]. The same is true for other cases.

Figure 128:
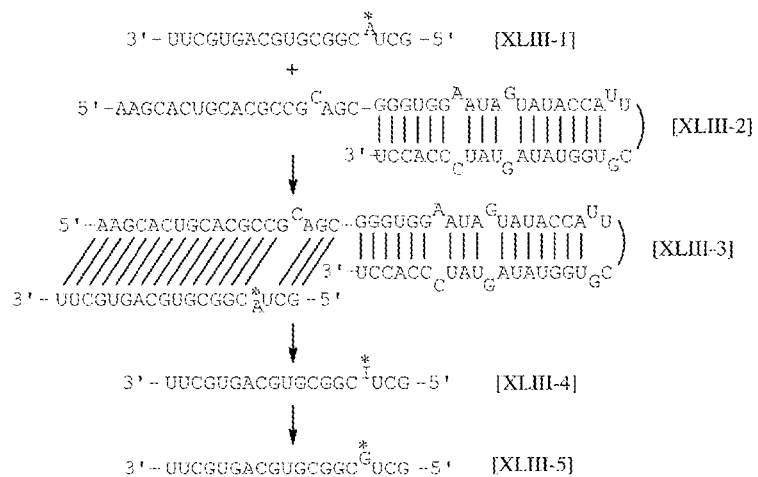

The present invention can be similarly implemented by using other target editing guides. For example, the case where GFP RNA is used will be described in FIG. 128.

Figure 129:
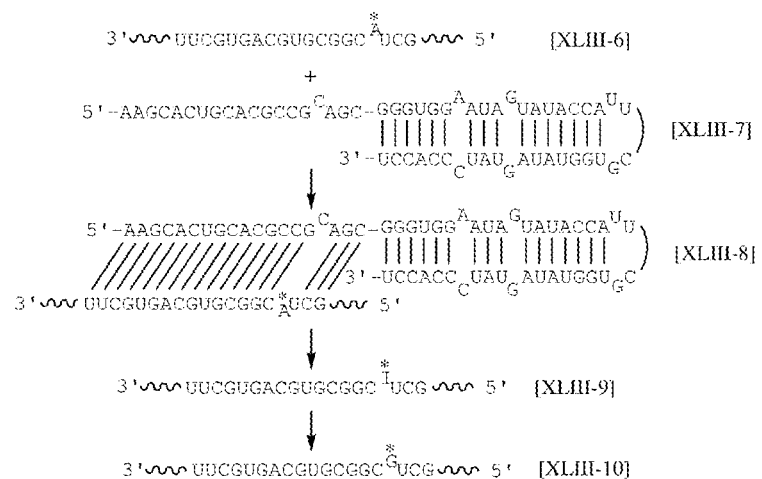

The same applies when the target RNA [XLIII-1] is used as full-length RNA or partial length RNA in FIG. 129.

Examples of RNA that can be used as a target RNA in the present invention include serotonin receptor, glutamate receptor, and membrane voltage-dependent potassium channel. However, any type of RNA can be used without limitation in the present invention as long as the target base adenosine to be RNA edited exists in the RNA.

In the present invention, when a certain predetermined RNA is selected as the target RNA from the RNAs, a specific region including a target editing site to be subjected to RNA editing can be selected from the selected target RNA. It should be noted that the specific region of the target RNA which can be subjected to RNA editing can be used irrespective of its form, whether it is 5'-target RNA or 3'-target RNA. For example, even when the target editing site is present near the 5' end and it is difficult to construct a base pair in the complementary region, the target editing site can be replaced with the corresponding side chain on the opposite side to secure a complementary region.

When a specific region of the target RNA is selected, it is possible to design a corresponding target recognition region of the target editing guide RNA which forms a complementary chain with the specific region. In this way, if the corresponding target recognition region of the target editing guide RNA can be designed, the target editing guide RNA can be easily designed by binding to the ADAR binding core region.

Once the target editing guide RNA can be designed as described above, the target editing guide RNA of the present invention can be synthesized in accordance with a common method. For example, the target editing guide RNA of the present invention can be synthesized by synthesizing a DNA molecule corresponding to the target editing guide RNA, and using the DNA molecule as a template by an in vitro transcription reaction or the like. That is, the target editing guide RNA of the present invention can be constructed by synthesizing synthetic oligo DNAs corresponding to each single strand of the double-strand constituting this target editing guide RNA, synthesizing each single strand by an annealing reaction or the like, and performing in vitro transcription reaction or the like using the synthesized DNA molecule as a template.

Further, in the present invention, the target editing guide RNA (gRNA) can be constructed to correspond to the target complementary region having the target editing site of every target RNA. Thus, the present invention can be easily and universally applied to any target RNA having a target base adenosine.

As the editing guide RNA (gRNA) used in the A-I RNA editing reaction according to the present invention, for example, a 3'-editing guide RNA represented by the general formula [LTA] or a 5'-editing guide RNA represented by the general formula [LVIA] can be mentioned. More specifically, the 3'-editing guide RNA [LIA] is composed of a 3'-target recognition region and an ADAR-binding region. Similarly, the 5'-editing guide RNA [LVIA] is composed of a 5'-target recognition region and an ADAR binding region.

More specifically, the 3'-target recognition region of 3'-editing guide RNA [LIA] is composed of 3'-[terminal side target recognition region-X-core side target recognition region], and the core side target recognition region has a structure in which the 5' end thereof is bound to the 3'-end of the ADAR binding core region. On the other hand, the 5'-target recognition region of the 5'-editing guide RNA [LVIA] is composed of 5'-[terminal side target recognition region-X-core side target recognition region] and the 3' terminus of the core side target recognition region is bonded to the 5'-end of the ADAR binding core region. The target recognition region is also referred to as an antisense region.

It should be noted here that in order to improve the editing efficiency, each core side target recognition region has its number of bases greater than the number of bases in the guide side decoupling region of the corresponding ADAR binding region. In other words, the base sequence is preferably designed to be long. That is, the number of the bases in the base sequence of the core side target recognition region is preferably 1 to 10, and preferably 1 to 5.

Figure 22B:
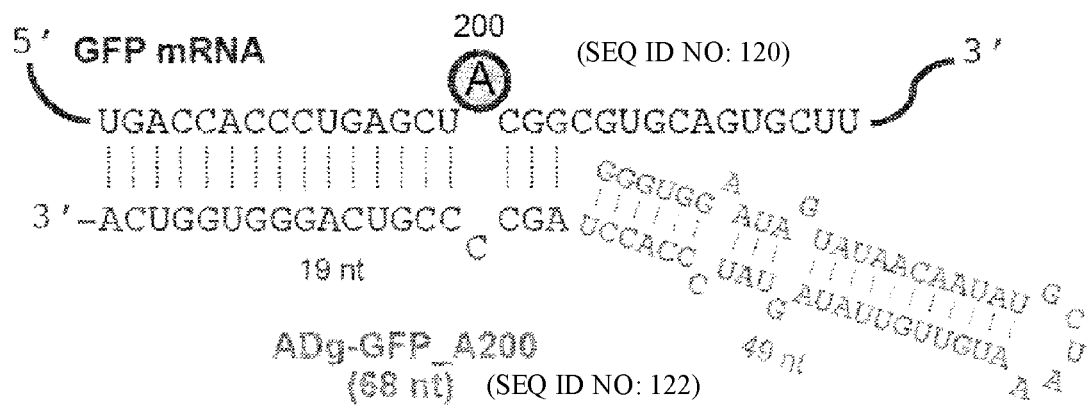
FIG. 22B shows another sequence of ADg-GFP_A200.

More specifically, referring to FIG. 22B, for example, for the 3-gRNA (ADg-GFP_A200) (68 nt) having the editing target A200, the number of bases in the antisense region is 19 nt, the number of bases in the ADAR binding region (3 ng) is 49 nt, and the number of bases in the core side target recognition region was designed to be longer by about 3. This also applies to the case of FIG. 22A. This also applies to other examples.

In other words, one main object of the present invention is to provide a simple gRNA design which induces the original A-I RNA editing activity of hADAR2 and to apply the gRNA to site-directed RNA mutagenesis. gRNA generally consists of a protein binding region that induces an enzyme protein such as Fibrillarin or Cbf5 on the target RNA and an antisense region that mediates target RNA via base pairing. In addition, the most important feature of gRNA is that the protein bound to gRNA is positioned to react effectively with the target site after the antisense gRNA region hybridizes to the target RNA. In order to construct RNA (AD-gRNA) that guides hADAR2 having such a function, attention was paid to the secondary structure of a natural editing substrate.

In the editing reaction of gRNA and hADAR2 according to the present invention, dsRBD mainly regulates substrate RNA binding, and the deaminase domain catalyzes the hydrolytic deamination reaction of adenosine (FIG. 21a). Thus, the natural structure of the substrate is considered to be adapted to the duplex structure required for dsRBD binding as well as enzyme activity. Thus, using the dsRBD binding region (including the antisense sequence forming the base pairing around the editing site) based on the natural editing substrate RNA, it was thought that AD-gRNA capable of reconstituting the structure of the natural substrate can be constructed (FIG. 21a). FIG. 21a shows the outline of the gRNA strategy for the site-directed RNA editing of the present invention, and the outline of the A-I RNA editing by hADAR2 is shown in the gray background. hADAR2 is composed of two dsRBDs and a deaminase domain. dsRBD primarily regulates the binding of the substrate RNA, and the deaminase domain promotes hydrolytic deamination. According to the present invention, specific A-I RNA editing can be carried out simply by using the ADAR protein. The AD-gRNA composed of an antisense region and an ADAR binding region was designed based on a natural substrate RNA structure. In the figure, the target editing part is marked with a circled A. The structure of natural substrate RNA is induced by hybridization of AD-gRNA with the target RNA. The target site-directed RNA editing is accomplished by hADAR2 site-directed editing reaction on the reconstituted substrate RNA. FIG. 21b shows the sequence of AD-gRNA designed on the basis of the secondary structure of GluR 2 (GRIA 2) pre-mRNA, an editing substrate of natural hADAR2 (Non-Patent Literature 26). The known editing site of GluR2 RNA (R/G site) is marked with a circled A. The stem-loop structure of GluR2 RNA can be split into two components. One component is believed to be a target guide RNA containing a targeted editing site, and the other component is believed to be a prototype AD-gRNA containing an antisense region (FIG. 21b). The site where this GluR2 RNA can be divided into two is indicated by an arrowhead and the AD-gRNA is shown in the gray background. The symbol X may be any nucleotide, and the dotted lines indicate base pairing. When X is completely base-paired, the cognate editing substrate structure is reconstructed. In this design, the antisense region acts as a determinant for targeting, and can be freely changed depending on the target site.

In order to verify, the validity of this AD-gRNA design. AD-gRNA induced RNA editing on green fluorescent protein (AcGFP) mRNA (720 nt; FIG. 21c) extracted from *Anthurium coerulescens* was shown. According to the above design, the AD-gRNA targeting A200 of GFP mRNA (ADg-GFP A200) is achieved by a 17-nt antisense region and a 49-nt ADAR binding region (FIG. 21b; its detailed design is shown in FIG. 22B). Conjugate formation of gRNA and GFP mRNA was confirmed by gel mobility shift assays and an annealing reaction using short-chain RNA fragments of ADg-RNA_A200 and AcGFP RNA (160 nt) synthesized in vitro including A200 site (see FIG. 23). After the complex formation reaction, the annealed gRNA-mRNA was allowed to react with hADAR2 for 1 hour. Subsequently, the editing induction efficiency of AD-gRNA was analyzed by reverse transcription (RT) and the fluorescent dye terminator sequencing method using AcGFP cDNA generated by PCR (Non-Patent Literature 29) (FIG. 21c). FIG. 21c shows the editing-inducing activity of AD-gRNA by a sequence chromatogram of GFP cDNA obtained by RT-PCR and in vitro editing reaction. The top panel shows recombinant hADAR2 without gRNA, the central panel shows the results in the antisense region (17 nt), and the bottom panel shows the results with ADg-GFP-A200. The target site is indicated by an arrowhead. As shown in the figure, in the editing reaction in the absence of AD-gRNA, editing of A200 was not detected in the obtained sequencing chromatogram. When editing reaction was performed by adding only the antisense region of ADg-GFP_A200, A200 was slightly edited. On the other hand, in contrast to these, when editing reaction was performed by adding ADg-GFP-A200, A200 was edited efficiently (~80%; calculated from the ratio of the peak height of G/A) (FIG. 21). These results clearly show that AD-gRNA can induce hADAR2 editing activity in a target site-directed and highly efficient manner.

Furthermore, the inventors tested the utility of other infrastructure in AD-gRNA construction using RNA (40 nt) having a hairpin structure which is already reported as a substrate of hADAR2 (Non-Patent Literatures 30, 31) (FIG. 24a). As a result, even if a sequence shorter than the ADAR binding region derived from GluR2 was used. AD guide RNA constructed according to this design efficiently compiled the target mRNA (84.9%) (FIGS. 24b and 24c). These results strongly indicate that it is possible to apply various RNA sequences as the ADAR binding region in AD-gRNA construction, and to further shorten the chain of AD-gRNA.

The diversity of the functional design of AD-gRNA was expanded. In the case of cis-type substrate such as GluR2 RNA and hairpin substrate, hADAR2 could not edit the site existing on the chain opposite to the original editing site (FIG. 25). On the other hand, in the trans-type substrate composed of gRNA and target RNA, it is predicted that due to the loss of phosphodiester bond in the target RNA, the ADAR binding region acquires rotational degree of freedom. Thus, it was considered that AD-gRNA having an antisense region on the 5' side of ADAR binding region could be constructed. To test this possibility, the modified AD-gRNA targeting the same site (A200) was designed by introducing an antisense sequence at the 5' position of the ADAR binding region (ADg-rGFP A200) (FIG. 22Aa). As expected, ADg-rGFP-A200 showed specific editing-inducing activity for A200 (FIG. 22Ab). Surprisingly, this editing activity was much higher than the original ADg-GFP-A200. FIG. 22Ab shows a temporal change in editing ratio at A200. Red circle indicates 5-antisense region, solid red circle indicates 5-antisense AD-gRNA (ADg-rGFP-A200), blue triangle indicates 3-antisense region, and solid blue triangle indicates 3-antisense AD-gRNA (ADg-GFP-A200), and solid triangle is the case without gRNA. Each editing percentage was calculated by quantifying the generated bases A and G from the direct sequencing chromatograph using the formula: (G peak height)/(A peak height+G peak height). The results are presented as averages with standard deviations from three independent experiments. This characteristic was also observed in the guide RNA generated from the hairpin matrix (FIG. 24c). In order to further evaluate the effect of rotational freedom of the ADAR binding region, extended AD-gRNA (ADg-rGFPex A200) added with sequence on its 3' side was tested to promote base pairing with the target RNA (FIG. 26). ADg-rGFPex_A200 showed different editing specificity and efficiency compared to ADg-rGFP_A200 (FIG. 26). This result shows that the rotational freedom of the ADAR binding region is important for inducing target editing.

In principle, the specificity of AD-gRNA induced-RNA editing depends greatly on the inherent selectivity of the deaminase domain of hADAR2. Thus, the editing pattern of AD-gRNA induced-RNA editing is considered to be similar to that of naturally edited substrates. Indeed, the neighboring specificity of AD-gRNA induced-RNA editing was almost identical to that observed for cis-type substrates (FIGS. 25 and 27). This indicates that AD-gRNA can induce structures similar to those occurring in natural substrates.

As a result, the present inventors have successfully developed a highly active AD-gRNA framework by introducing an antisense region to the 5' side of the ADAR binding region.

Figure 28:
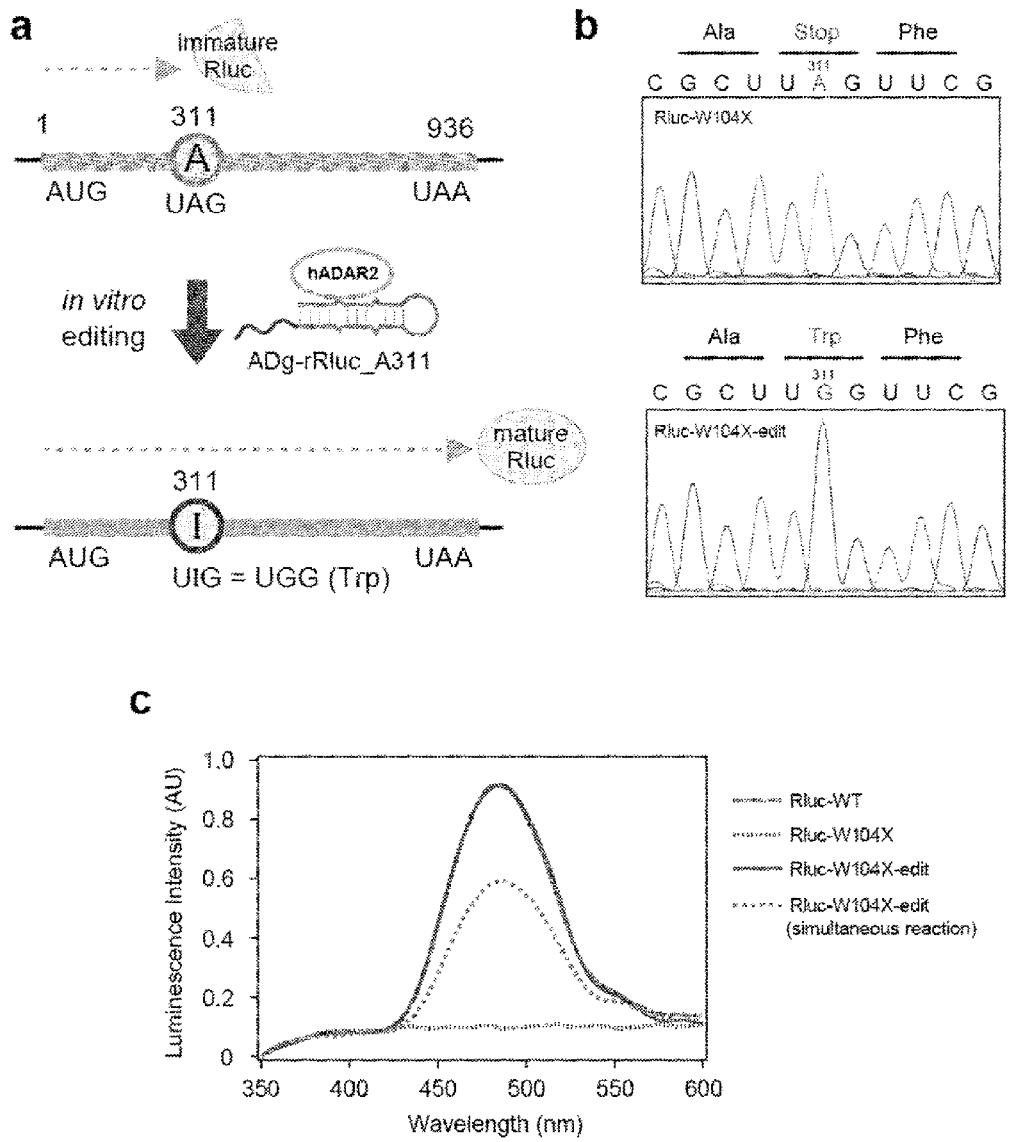
FIG. 28 illustrates the regulation of functional protein expression by AD-gRNA induced RNA editing, a sequence chromatogram of cDNA from Rluc-W104X (upper panel) and Rluc-W104X (lower panel) in vitro edited with ADg-rRluc_A311; (c) shows active luciferase expression regulated by AD-gRNA.

In vitro regulation of functional protein expression using AD-gRNA-induced A-I RNA editing will be described. A likely promising application of site-directed RNA mutagenesis seems to be regulating the expression or function of the target protein by introducing specific codons. In order to demonstrate the possibility of such application, codon repair experiments were carried out using AD-gRNA in vitro editing and in vitro translation system. In this experiment, Rluc-W104X obtained by converting nucleotide 311 of *Renilla* luciferase (Rluc) mRNA to adenosine (A311) and converting Trp104 codon (UGG) to stop codon (UAG) was used as a reporter (FIG. 28). Since inosine is read as guanosine by the translational machinery, the active mature luciferase is translated from Rluc-W104X only when A311 has been edited to 1 311 by ADg-rRluc_A311 and then regenerated the Trp codon (UIG; FIG. 28a). That is, regulation of protein expression by AD-gRNA-induced A-I RNA editing can be analyzed by monitoring luciferase activity after in vitro translation of edited reporter RNA.

Figure 29:
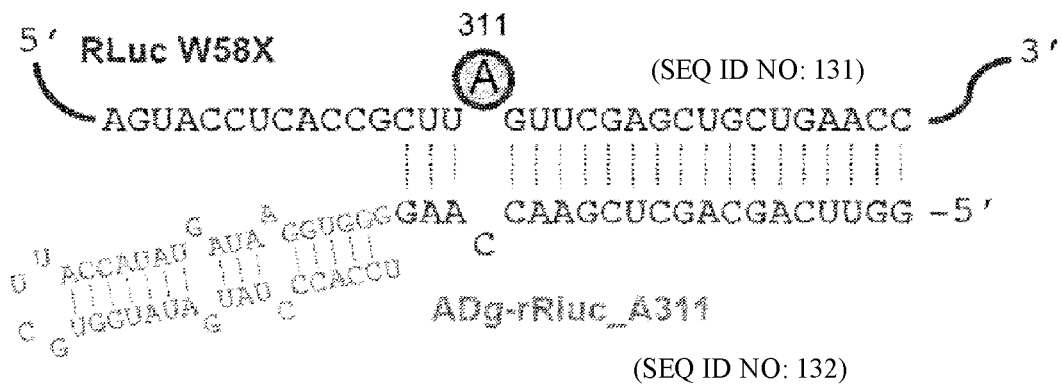
FIG. 29 shows the sequence of ADg-rRluc_A311.

First, AD-gRNA with codon transformation was designed based on the 5'-antisense framework (ADg-rRluc_A311; FIG. 29). In order to evaluate the codon conversion induced by ADg-rRluc_A311, the editing efficiency at A311 was analyzed after the in vitro editing reaction. Similar to the results observed for ADg-rGFP, A311 could be efficiently and site-directedly edited in the resulting sequencing chromatogram (FIG. 28b). That is, by the above reaction, Rluc-W104X mRNA in which A311 was converted to 1311 was obtained. Next, in order to demonstrate whether codon conversion caused by AD-gRNA can control active luciferase expression, in vitro translational reaction was performed using Rluc-W104X after the editing reaction, and then a luciferase assay was performed (FIG. 28c). Luminescence emission spectral analysis of the sample was performed after in vitro translation reaction with wild type luciferase mRNA (Rluc-WT black), Rluc-W104X (blue), or Rluc-W104X (purple) edited in vitro. As a result, active luciferase expression could not be observed when unedited Rluc-W104X transcript was used. In contrast, a typical luminescence emission spectrum was detected from samples translated using the Rluc-W104X transcript after the editing reaction. In addition, its luminescence intensity was equivalent to that obtained using wild type Rluc mRNA (Rluc-WT). These results clearly show that the AD-gRNA strategy can be effectively applied to regulate functional protein expression.

Figure 30:
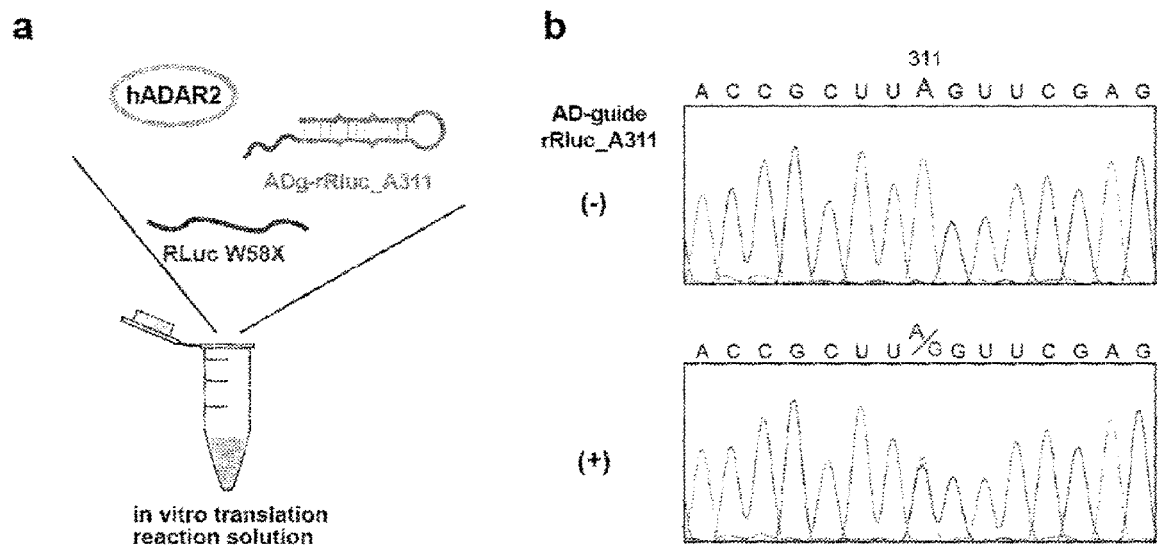
FIG. 30 illustrates an experiment which investigated the capability of AD-gRNA even under more complicated circumstances; (a) shows an experimental system for performing translation/editing reaction simultaneously using ADg-rRluc_A311, Rluc-W104X, and hADAR2; (b) shows editing efficiency of A311 of ADg-rRluc_A311; The upper panel shows the case without guide RNA, and the lower panel shows the case using ADg-rRluc_A311.

Furthermore, to investigate the possibility of AD-gRNA in a more complex environment, a simultaneous editing reaction was performed (FIG. 30a). In this experiment, ADg-rRluc_A311. Rluc-W104X, and hADAR2 were mixed together with the reaction components required for in vitro translation, and then reacted for 30 min. The editing efficiency and the luciferase activity were then analyzed. After completion of the reaction, the editing efficiency of Rluc-W104X at A311 was 47% (FIG. 30b). Luciferase activity was also observed in the simultaneous reaction, and this luminescence intensity was almost half of the value detected by the single reaction (FIG. 28c).

Figure 31:
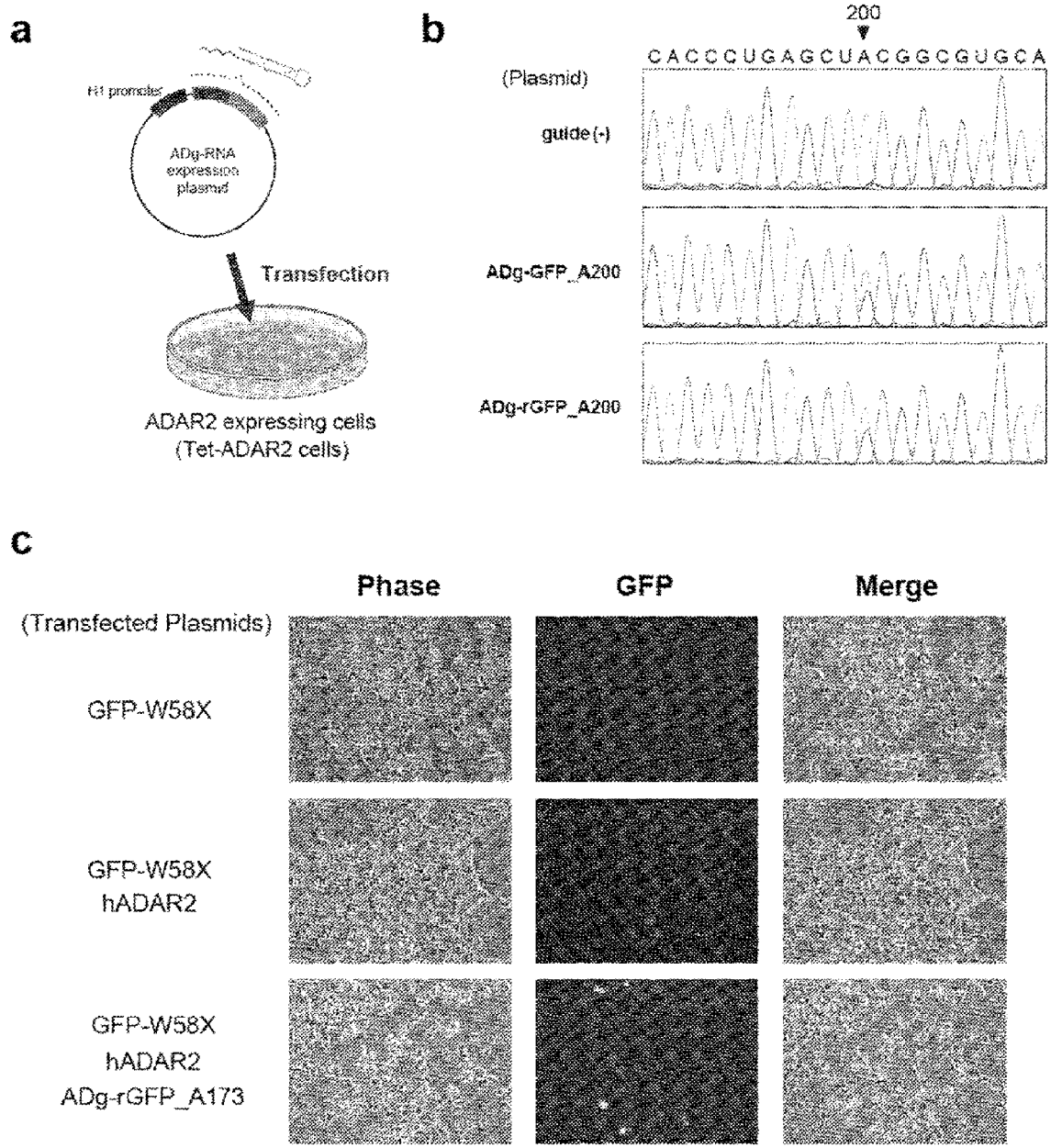
FIG. 31 shows application of AD-gRNA for inducing a site-directed RNA mutation and regulation of intracellular target protein expression; (a) shows site-directed RNA mutagenesis by simple plasmid transfection in hADAR2-expressing cells; (b) shows confirmation of the specific editing-inducing activity of ADg-GFP_A200 and ADg-rGFP_A200 in tet-ADAR 2 cells; (c) illustrates an intracellular codon repair experiment.
Figure 32:
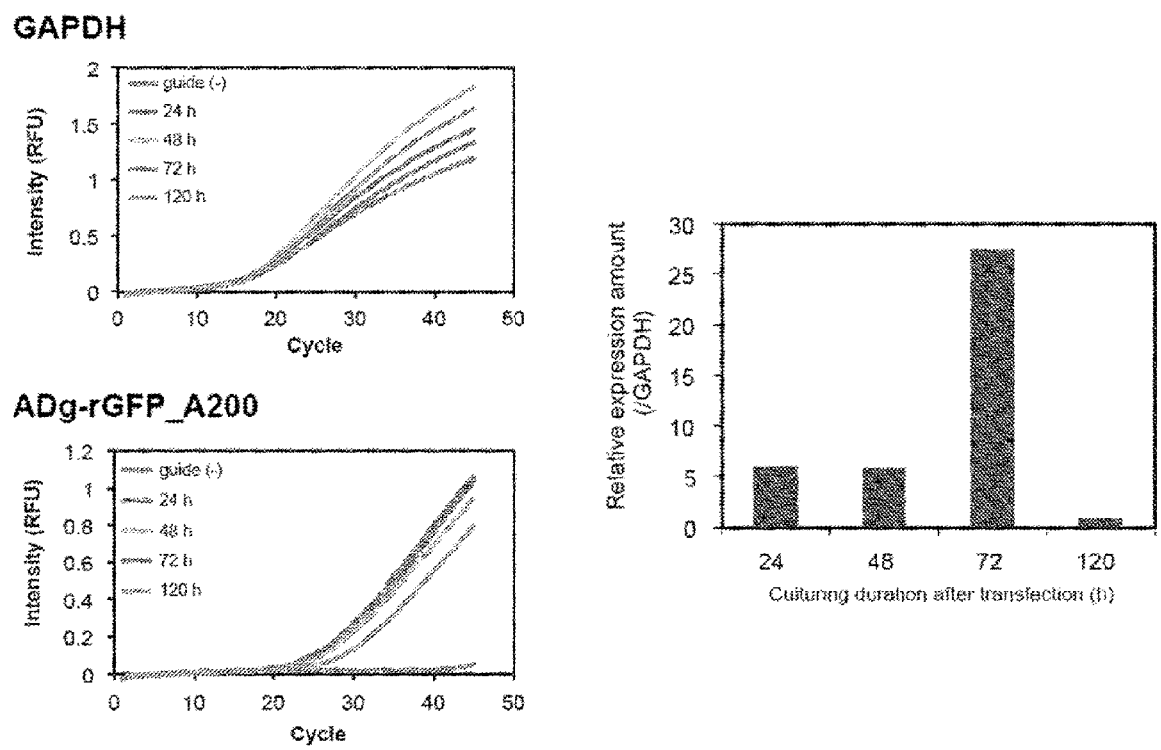
FIG. 32 shows RT and quantitative PCR (qPCR) results of intracellular ADg-GFP A200 in tet-ADAR 2 cells.
Figure 33:
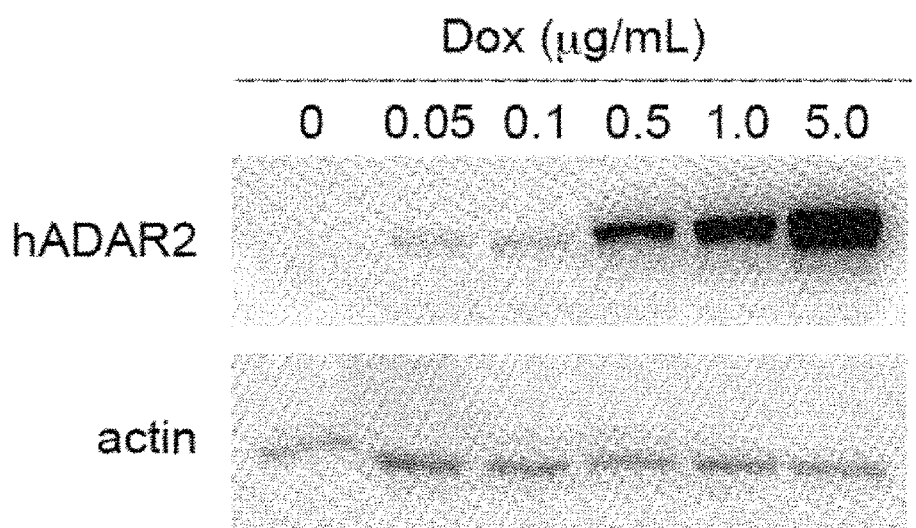
FIG. 33 shows Western blot analysis results of hADAR2 expression in tet-ADAR2 cells.

Subsequently, intracellular RNA mutagenesis was performed based on the AD-gRNA strategy. The most important advantage of AD-gRNA is its capability to induce the editing activity of native hADAR2. Thus, induction of the intracellular target RNA mutation does not require foreign protein, and can be achieved only by introduction of AD-gRNA into cells expressing hADAR2. To demonstrate this, the tet-ADAR2 cell line (Non-Patent Literature 32) capable of co-expressing hADAR2 and AcGFP under the control of the doxycycline (Dox) inducible promoter was used as the hADAR2 expression model cell (FIG. 31a). In this experiment, it was investigated whether ADg-GFP_A200 and ADg-rGFP_A200 already characterized in previous studies can guide the editing activity of hADAR2 in tet-ADAR 2 cells to AcGFP mRNA. In this experiment, as a method for introducing AD-gRNA into cells, a method of expressing by AD plasmid vector was used. In order to show whether the usefulness of the AD-gRNA strategy is comparable to conventional siRNA or miRNA technology, pSupeme, which expresses short-chain RNA with commonly used pol III, was used as the expression vector (FIG. 31a). Expression plasmids of various AD-gRNAs were constructed using the above-described short-chain RNA expression vectors. Expression of hADAR2 and AD-gRNA was confirmed by using Western blotting and real-time PCR (FIGS. 32 and 33). To analyze the efficiency of AD-gRNA-inducible A-I RNA compilation, GFP mRNA was extracted from tet-ADAR2 cells transduced with plasmid and co-cultured with Dox, and subjected to direct sequencing after RT-PCR. As a result, editing of the target site A200 by transduction of the AD-gRNA expression plasmid was detected (FIG. 31). FIG.

Figure 34:
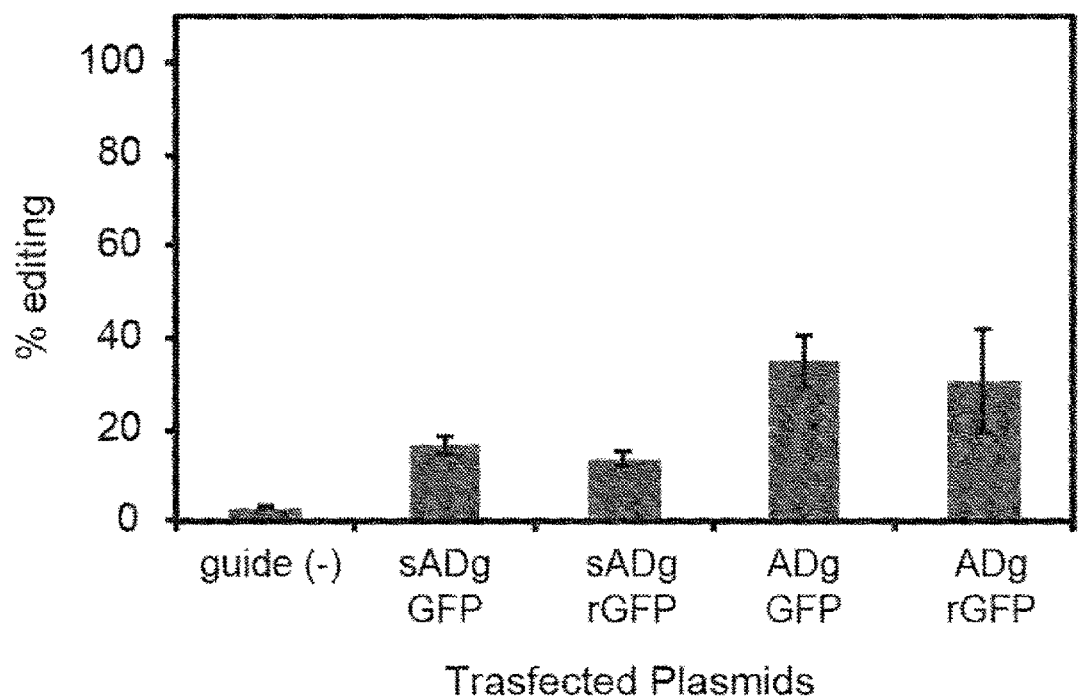
FIG. 34 shows editing efficiency induced by tet-ADAR2 intracellular AD-gRNAs.

31b shows the results of confirming the specific editing-inducing activity of ADg-GFP-A200 and ADg-rGFP_A200 in tet-ADAR2 cells. The panels each show a sequence chromatogram of GFP cDNA obtained from cells without plasmid transfection (guide [-], the upper panel), with the introduction and culturing of the expression plasmid of ADg-GFP-A200 (the middle panel), and of ADg-rGFP_A200 (the lower panel). In the figure, the target base adenosine (A200) is indicated by an arrowhead. Editing efficiencies at nucleotide A200 from cells expressing ADg-GFP_A200 and ADg-rGFPA_200 were 34.9% and 30.5%, respectively (FIGS. 31 and 34). In addition, no clear off-target editing (nonspecific editing that is not at the target site) was detected in any of the extracted AcGFP mRNA adenosine. Thus, these results indicate that AD-gRNA works well in hADAR2 expressing cells. The most important point from these results is that intracellular site-directed RNA mutagenesis can be performed by simple plasmid transduction of AD-gRNA.

In addition, intracellular codon repair experiments were performed to demonstrate that functional expression of intracellular proteins can be regulated by the AD-gRNA strategy. In order to visualize the regulation of functional expression of intracellular proteins induced by AD-gRNA induced codon repair, mutant A173GFP mRNA (GFP-W58X RNA) introduced with a stop codon by mutating G173 in codon Trp 58 was used as a reporter gene (Non-Patent Literatures 25 and 33). Also, ADg-rGFP.A173 was designed to repair this stop codon to the Trp codon, and the corresponding expression plasmid was constructed using the pSUPER neo vector. For expression of hADAR2 and GFP-W58X, an expression plasmid was constructed based on the pcDNA 3.1 vector, which is commonly used for protein expression, and these plasmids were transduced into co-HEK293 cells, and after cultured for 48 hours, intracellular fluorescence was detected with a fluorescence microscope. Positive cells with clear fluorescence were not detected using control cells lacking AD-gRNA expression transduced with GFP-W58X and/or hADAR2 plasmid (FIG. 31c). In contrast, several cells with bright fluorescence were identified by transducing AD-gRNA expression plasmids (FIG. 31c). From the above results, it was shown that biosynthesis of mature GFP can be regulated by introducing RNA a mutation by ADg-rGFP_A173. The results clearly show usefulness of RNA mutation induction to regulate the function of the target protein based on the AD-gRNA strategy.

Various methods of intracellular A-I RNA editing as described above can be an important breakthrough for establishing practical site-directed RNA mutagenesis. Previously, artificial gRNA was used to direct the RNA modification activity of natural riboprotein (Non-Patent Literatures 19 to 21). However, A-I RNA editing in vivo is performed only with ADAR protein, and gRNA inducing ADAR has not been found in nature. Thus, it was impossible to directly apply the gRNA strategy according to the conventional method to induction of A-I RNA editing. Site-specific RNA editing was previously accomplished using useful etitases consisting of artificial gRNA and modified ADAR protein (Non-Patent Literatures 22, 23, 24). However, these methods lose the advantage of the conventional gRNA strategy of achieving the objective only by introducing gRNA using the endogenous modification mechanism. Thus, constructing a novel gRNA that can induce the editing activity of endogenous ADAR freely at the target site was believed to construct a site-directed RNA mutation introduction method using the endogenous A-I RNA editing mechanism.

In the present invention, AD-gRNA can be easily designed based on the secondary structure of a natural or artificial editing substrate having a hADAR2 expression site. In the case of GluR2 RNA, the region bound by dsRBD of hADAR2 has been clarified by structural analysis by NMR (Non-Patent Literature 34). Judging from the structural information, the GluR2 RNA is divided into two parts, one divided part is considered to be a target RNA having an editing site, and the other is considered to be a prototype type AD-gRNA consisting of an ADAR binding region and an antisense region (FIG. 21b). In theory, the edited substrate structure is reconstructed by recombining the divided RNAs. Thus, AD-gRNA can induce A-I editing by hADAR2 against any of the target base adenosines by altering the antisense region to match the target sequence. Indeed, AD-gRNA targeting various sites on GFP and Luc mRNA was constructed with this design. In addition, from the results of the present invention, the flanking specificity of RNA edition induced by AD-gRNA was very similar to that observed in natural substrates (FIGS. 25 and 26). This indicates that the complex consisting of AD-gRNA and RNA forms a structure similar to the natural editing substrate structure.

The AD-gRNA of the present invention was constructed using a basic skeleton in which a dividing line between both RNA components was immobilized at a position 3 nucleotides (nt) downstream of the target editing site (FIG. 21b). When this dividing line is 0 nt or 1 nt, the editing efficiency decreased, but nearly constant editing efficiency was observed at distances of 2-5 nt away (FIG. 35). These observations indicate that in this AD-gRNA design, in order to efficiently drive the reaction with hADAR2, a double strand structure containing two or more base pairings between the target editing site and the ADAR binding domain can be said to be necessary. Thus, 3 bp framework was used in this experiment. As another method, the editing efficiency can be changed to some extent by changing the dividing line, so the possibility of using different basic skeletons in AD-gRNA construction was shown.

Normally, the antisense region is located on the 3' side of this design based on the GluR2 RNA, but in the design of AD-gRNA, the position can be located both 3' and 5' sides of the ADAR binding region. It is believed that the position of the antisense region is considered to be interchangeable as a result of increased rotational freedom of the ADAR binding region caused by loss of phosphodiester bond in the target RNA. This concept is supported by different editing behavior of ADg-rGFPex as observed when the sequence is additionally introduced to the 3~ side that base pairing with the target RNA is caused, and that the degree of rotational freedom of the ADAR binding region is suppressed (FIG. 27). Indeed, the editing efficiency of 5'-antisense AD-gRNA was more efficient than 3'-antisense AD-gRNA. In the case of a trans-type substrate consisting of AD-gRNA and target RNA, 3'-antisense AD-gRNA may induce a more favorable structure for editing induction of hADAR.

Because hADAR2 preferentially edits adenosine in dsRNA, simple antisense RNA also has strong potential to be used as guide RNA. The antisense region of ADg-GFP_A200 shows the capability to induce A-I editing (FIG. 21c), but its efficiency was significantly lower than observed with complete AD-gRNA with ADAR binding region introduced. This result shows that ADg-RNA has high pluripotency for inducing efficient editing.

However, nonspecific editing can occur in the antisense region depending on the surrounding sequence of the target. Specifically, in the dsRNA structure, nt 11 bases apart from the target base adenosine are located on the sterically same surface. Thus, adenosine present at this position may be nonspecifically edited by induced ADAR. In addition, the editing pattern induced by AD-gRNA is highly dependent on hADAR2 specific properties. For example, if a target site is present in a contiguous adenosine sequence, adenosine adjacent to that target site is edited simultaneously (FIGS. 25, 26). It is therefore considered difficult to highly improve the editing specificity at the adjacent site over the inherent properties of native hADAR2 using the AD-gRNA design of the present invention. It has been reported that unwanted editing by ADAR can be effectively suppressed by introducing mismatched nt at the complementary position to adenosine of interest or by modifying adjacent nucleotides of the antisense region (Non-Patent Literature 23). Given the similarity of reaction specificities observed with this artificial editase, it seems possible to apply these strategies for AD-gRNA induced RNA editing to regulate target selectivity. Conversely, by utilizing the flanking specificity of native hADAR2, it is possible to edit multiple adenosines at once.

According to the present invention, this result of successfully modifying the ADAR binding region (FIG. 24) strongly suggests the possibility of constructing AD-gRNA using an ADAR binding region different from the present invention from natural editing substrate RNAs such as the GluR2 Q/R site (Non-Patent Literature 35) and the NEIL1 K/R site (Non-Patent Literature 36). It is known that the GluR2R/G site is also compiled by hADAR1, another RNA-editing enzyme. Since hADAR1 has a domain structure similar to that of hADAR2 (Non-Patent Literatures 13 and 37), the design strategy of the present invention can be applied not only to hADAR2 guide RNA but also to hADAR1 guide RNA. Thus, it was considered that the AD-gRNA developed in the present invention can directly induce the editing activity of hADAR. Thus, an editing induction assay using hADAR1 was performed. As a result, although the efficiency decreased as compared to the case of hADAR2, it was confirmed that editing guidance is certainly possible. This guide RNA design is showed to be effective to both hADAR1 and hADAR2.

Target selectivity and efficiency are considered to be the two most important requirements for being generally applicable mutagenesis methods. The AD-gRNA according to the present invention was effective both in vitro and intracellularly, and showed site-selective activity, but by further optimizing it, it is expected that it is possible to improve the activity of AD-gRNA according to its intended use. The diversity of functional adjustment by the design of the present invention is very useful for improving editing efficiency and avoiding nonspecific editing.

Intracellular site-directed RNA editing can be accomplished simply by expressing AD-gRNA in hADAR2 expressing cells. Moreover, it is evident that in the codon repair experiments (in vitro and intracellular) according to the present invention, the AD-gRNA strategy of the present invention can be applied to change codons and ultimately change the function of the target protein. Theoretically, 12 amino acids (Ser, Thr, His, Lys, Arg. Asp, Glu, Asn, Gln, Tyr, Ile and Met/start) out of all 20 amino acids can be changed by the A-I mutation generated in the coding region of mRNA. These codon transformations include metal chelating sites (generally His, Asp and Glu) and phosphorylation sites (Ser, Thr and Tyr), so that A-I RNA editing is likely to strongly control the functions of various intracellular proteins such as enzyme catalysts and protein phosphorylation signal transduction. Thus, the AD-gRNA strategy of the present invention has great potential as a new site-directed RNA mutation induction method applicable to control of various biological processes.

In summary, the novel gRNA system of the present invention can induce A-I mutation by guiding hADAR2 to the target site. AD-gRNA can specifically introduce the A-I mutation at the target site programmed into the antisense region. Moreover, the method for introducing a site-directed RNA mutation of the present invention can be accomplished merely by introducing gRNA into ADAR expressing cells. Thus, the gRNA strategy of the present invention provides a basic framework that is simple in design, easy to use, and necessary for establishing general RNA mutation induction.

Hereinafter, the present invention will be described in more detail with reference to examples, but the following examples are intended to more specifically explain the present invention, and do not limit the present invention in any sense in any way. Of course, any improvements, modifications, etc. derived or originated from the following examples are included in the scope of the present invention.

EXAMPLE 1

Synthesis of 3-Target Editing Guide RNA

The reaction solution containing 100 mM of the synthetic oligo DNA (1) (guide RNA_D 3_tempT7F) and 100 mM of the synthetic oligo DNA (2) (guide RNA D 3_tempR) was treated at 95° C. for 3 min. and subsequently reduced to 25° C. for 15 min, and then annealing reaction was carried out to obtain DNA (guide RNA_D3_tempF/R). Subsequently, 2.5 mM dNTP and 5000 U/mL Klenow fragment were added (final concentration: guide RNA_D3 tempF/R 2 mM, dNTP 0.2 mM, Klenow fragment 2.5 U) and elongated at 25° C. for 30 min, and DNA was purified by phenol/chloroform extraction and ethanol precipitation. RNA (3'-target editing guide RNA 1) was synthesized by in vitro transcription (37° C. for 3 hours) using the obtained DNA as a template and T7-Scribe Standard RNA IVT KIT. Thereafter. DNAse (final concentration: 2 U) was added, the mixture was treated at 37° C. for 15 min. and the RNA was purified by phenol/chloroform extraction and ethanol precipitation. The resulting RNA was purified with 8 M Urea PAGE (8%), extracted by grinding/dipping, and purified by 0.22 mm filter (DU-RAPORE) and gel filtration (BIO RAD).

In other words, the template DNA used to synthesize 3'-target editing guide RNA in vitro was synthesized using synthetic oligo DNA (1) guide RNA_D3_tempT7F and synthetic oligo DNA (2) guide RNA_D3_tempR. The base sequence of each synthesized oligo DNA used is as follows.

```
                                          (SEQ ID NO: 1)
(1) guide RNA_D3_tempT7F (48 mer)
CTAATACGACTCACTATAGGGTGGAATAGTATACCATTCGTGGTATAG
```

```
                                          (SEQ ID NO: 2)
(2) guide RNA_D3_tempR (44 mer)
TGACCACCCTGAGCTGCGGAGGTGGGATACTATACCACGAATGG
```

EXAMPLE 2

Synthesis of 3'-Target Editing Guide RNA

A reaction solution containing 100 mM of synthetic oligo DNA (3) (guide RNA_D0_tempT7F) and 100 mM of synthetic oligo DNA (4) (guide RNA_D0_tempR) was treated in substantially the same manner as in Example 1 to obtain RNA (3'-editing guide RNA2).

The base sequences of synthetic oligo DNA (3) (guide RNA_D0_tempT7F) and synthetic oligo DNA (4) (guide RNA_D0_tempR) are as follows.

(SEQ ID NO: 3)
(3) guide RNA_D0_tempT7F (51 mer)
CTAATACGACTCACTATAGGTGGGTGGAATAGTATACCATTCGTGGTATAG (SEQ ID NO: 4)
(4) guide RNA_D0_tempR (44 mer)
TGACCACCCTGAGCTGGGTAGGTGGGATACTATACCACGAATGG

EXAMPLE 3

Synthesis of 5-Target Editing Guide RNA

A reaction solution containing 100 mM of synthetic oligo DNA (5) (guide RNA_D3r_tempT7F) and 100 mM of synthetic oligo DNA (6) (guide RNA_D3r_tempR) was treated in substantially the same manner as in Example 1 to obtain RNA (3-editing guide RNA3).

The base sequences of synthetic oligo DNA (5) (guide RNA_D3r_tempT7F) and synthetic oligo DNA (6) (guide RNA_D3r_tempR) are as follows.

(SEQ ID NO: 5)
(5) guide RNA_D3r_tempT7F (45 mer)
CTAATACGACTCACTATAGGGAAGCACTGCACGCCGCAGCGGGTG (SEQ ID NO: 6)
(6) guide RNA_D3r_tempR (49 mer)
AGGTGGGATACTATACCACGAATGGTATACTATTCCACCCGCTGCGGCG

EXAMPLE 4

Synthesis of 5-Target Editing Guide RNA

A reaction solution containing 100 mM of synthetic oligo DNA (7) (guide RNA_D0r_tempT7F) and 100 mM of synthetic oligo DNA (8) (guide RNA_D0r_tempR) was treated in substantially the same manner as in Example 1 to obtain RNA (3'-editing guide RNA 4).

The base sequences of the synthetic oligo DNA (7) (guide RNA_D0r_tempT7F) and the synthetic oligo DNA (8) (guide RNA_D0r_tempR) are as follows.

(SEQ ID NO: 7)
(7) guide RNA_D0r_tempT7F (45 mer)
CTAATACGACTCACTATAGGGAAGCACTGCACGCCGCGGTGGGTG (SEQ ID NO: 8)
(8) guide RNA_D0r_tempR (52 mer):
GGTAGGTGGGATACTATACCACGAATGGTATACTATTCCACCCACCGCGG
CG

EXAMPLE 5

Synthesis of GFP RNA (Target RNA)

Amplification was performed using GFP-Gq-TK plasmid as a template, with PCR (1 cycle (98° C. for 10 sec, 55° C. for 30 sec. 68° C. for 30 sec) 30 cycles) in a reaction solution containing 100 mM AcGFP_sRNA 01_T7F01 primer, 100 mM AcGFP_sRNA 01_R01 primer, and 2.5 mM dNTP, 1.25 U/mL Prime Star GXL (final concentration: GFP-Gq-TK Plasmid 4.0 pg/mL, AcGFP_sRNA 01_T7 F/R 0.3 mM, dNTP 0.2 mM, PrimeStar GXL 2.5 U). The amplified PCR product was purified by phenol/chloroform extraction and ethanol precipitation. Using the obtained DNA as a template and T7-Scribe Standard RNA IVT KIT, RNA was synthesized by in vitro transcription (37° C., 3 hours). Thereafter, DNAse (final concentration: 2 U) was added and processed (37° C., 15 min), and RNA was purified by phenol/chloroform extraction and ethanol precipitation. The resulting RNA was purified with 8M Urea PAGE (8%), extracted by grinding/dipping, and purified by 0.22 mm filter (DURAPORE) and gel filtration (BIO RAD).

The base sequence of the AcGFP_sRNA01_T7F01 primer is as follows.

(SEQ ID NO: 9)
CTAATACGACTCACTATAGGGCCACCCTGGTGACCACCC

The base sequence of the AcGFP_sRNA01_R01 primer is as follows.

(SEQ ID NO: 10)
GCGCGCGACTTGTAGTTGCC

EXAMPLE 6

Complex Formation Reaction Between Target Editing Guide RNA and Substrate RNA (Target RNA)

Annealing reaction (80° C. for 3 min→25° C. for 15 min.) of purified target editing guide RNA (final concentration: 0.45 mM) and target RNA (GFP sRNA 01) (final concentration: 0.45 mM) was performed in annealing buffer (150 mM NaCl, 10 mM Tris-HCl (pH 7.6)). After the reaction, formation of complex of target RNA (GFP RNA) and target editing guide RNA was confirmed with 8% Native PAGE.

The base sequence of GFP sRNA 01 is as follows.

(SEQ ID NO: 11)
GFP sRNA 01:
5'-GGGUGAAUGGCCACAAGUUCAGCGUGAGCGGCGAGGGCGAGGGCGAU

GCCACCUACGGCAAGCUGACCCUGAAGUUCAUCUGCACCACCGGCAAGCU

GCCUGUGCCCUGGCCCACCCUGGUGACCACCCUGAGCUACGGCGUGCAGU

GCUUCUC-3'

EXAMPLE 7

Complex Formation Reaction Between Target Editing Guide RNA and Substrate RNA (Target RNA)

Annealing reaction (80° C. for 3 min→25° C. for 15 min.) of purified target editing guide RNA (final concentration: 0.45 mM) and target RNA (GFP sRNA 01) (final concentration: 0.45 mM) was performed in annealing buffer (150 mM NaCl, 10 mM Tris-HCl (pH 7.6)). After the reaction, formation of complex of target RNA (GFP RNA) and target editing guide RNA was confirmed with 8% Native PAGE.

EXAMPLE 8

Evaluation of Editing Guide Capability of Editing Guide RNA

The 5-target editing guide RNA 1) purified in Example 1 or the 3'-target editing guide RNA 3 (each final concentration: 0.45 mM) purified in Example 3 and the target RNA (GFP RNA) synthesized in Example 5 (Final concentration: 0.45 mM) were subjected to an annealing reaction (80° C. for 3 min→25° C. for 15 min.) to obtain RNA complexes, respectively. The resulting RNA complex (0.45 mM) was diluted with TE Buffer to 50 mM. After dilution, purified recombinant hADAR2 (final concentration: 0.8 mM) was added to RNA complex (final concentration: 5 nM), and editing reaction was carried out (37° C., 1 hour). After the editing reaction, RNA complex 1 or RNA complex 2 was purified by phenol/chloroform extraction and ethanol precipitation, respectively. The resulting precipitate of each RNA complex was dissolved in 5 mL of TE Buffer and reverse transcription reaction was carried out using Prime Script Reverse Transcription Kit and AcGFP_sRNA_R01 primer (final concentration: 2.5 mM) (rapid quenching at 65° C. for 5 min, 42° C. for 45 min, 70° C. for 15 min.). PCR (1.25 U/mL Prime Star GXL, AcGFP_sRNA_T7F01 primer, cGFP_sRNA_R01 primer, 2.5 mM dNTP) (one cycle (98° C. for 10 sec. 55° C. for 15 sec, 68 sec for 20 sec), 25 cycles) was performed using the obtained cDNA as a template to amplify the double-stranded DNA. After that, DNA base sequence analysis was performed using the amplified DNA and the Big Dye Terminator v3.1 Cycle Sequencing Kit. An editing ratio was calculated from the peak ratio (G/A+G) of A (T) and G (C) of the target editing site of the obtained chromatographic chart. The edit rate of each of RNA complex 1 and RNA complex 2 was 88.1% and 91.2%. In contrast, the control of the target RNA alone was 2.7%.

EXAMPLE 9

The editing ratio was calculated for a complex obtained by subjecting 3'-target RNA [XLVIA-0 to XLVIA-5] and 5'-target editing guide RNA [XLVA-0 to XLVA-5] to annealing reaction in a manner substantially the same as in Example 8. The results are shown in Table 1 below showing the change of the editing rate over time.

TABLE 1

| Time | 3'-Target RNA - 3'-Target RNA (XLVA + XLVIA) | | | | | |
|---|---|---|---|---|---|---|
| (min.) | 0 | 1 | 2 | 3 | 4 | 5 |
| 0.5 | 3.3 | 3 | 4.3 | 3.3 | 5.3 | 6.7 |
| 5 | 3.3 | 7.8 | 13.5 | 14.2 | 25.4 | 24.4 |
| 10 | 3.4 | 9.5 | 22.8 | 20.9 | 30.4 | 37.8 |
| 15 | 3.3 | 16.3 | 32.1 | 30.8 | 43.7 | 44.3 |
| 30 | 8.9 | 25.5 | 44.6 | 44.6 | 57.9 | 52.4 |
| 60 | 3.2 | 33.9 | 59.2 | 61.9 | 67.2 | 65 |
| 120 | 2.3 | 44.1 | 70.6 | 74.9 | 62.4 | 67.2 |
| 180 | 3 | 45.6 | 73.9 | 76.8 | 79.6 | 74.8 |

EXAMPLE 10

Materials used in the following examples are as follows. DNA oligonucleotide and synthetic RNA were purchased from Hokkaido System Science Co, Ltd. (Hokkaido, Japan) and Sigma genosys (Hokkaido, Japan). The sequences of all DNA oligonucleotides and synthetic RNAs are listed in Tables 2 to 6.

TABLE 2

DNA oligonucleotides for in vitro synthesis of ADq-RNA

| target | name | sequence (5'→3') | SEQ ID NO: |
|---|---|---|---|
| ADg-GFP_A200 | ADg-GFP_A200_T7F | CTAATACGACTCACTATAGGGTGGAATAGTATAACAATATGC | 12 |
| | ADg-GFP_A200_RV | TGACCACCCTGAGCTGCGG | 13 |
| ADg-rGFP_A200 | ADg-rGFP_A200_T7F | CTAATAGGACTCACTATAGGGAAGCACTGCACGCCGCAGCGGGTGGAATAG | 14 |
| | ADg-rGFP_A200_RV01 | AGGTCGGATACTATAACAACATTTAGCATATTGTTATACTATTCCACCC | 15 |
| | ADg-rGFP_A200_RV02 | AGGTGGGATACTATAACAAGATTTAGC | 16 |
| ADg-rRluc_A311 | ADg-rRluc_A311_T7F | CTAATAGGACTCACTATAGGCTTCAGCAGGTCGAACCAAGGGGTGGAATAGTATAC | 17 |
| | ADg-rRluc_A311_RV | AGGTGGGATACTATACCACGAATGGTATAGTATTCCACCC | 18 |
| sADg-GFP_A200 | sAD9-GFP_A200_T7F | CTAATACGACTGACTATAGGGTGGAATAGTATACCATTCGTGCTATAG | 19 |
| | sADg-GFP_A200_RV | TGACCACCCTGAGGTGCGGAGGTGGGATACTATACCACGAATGG | 20 |
| sADg-rGFP_A200 | sADg-rGFP_A200_T7F | CTAATACGACTCACTATAGGGAAGCACTGCACGCCGCAGCGCGTC | 21 |
| | sADg-rGFP_A200_RV | AGGTGGGATACTATACCACGAATGGTATACTATTCCACCCGCTGCGGCG | 22 |
| eSL_AAA | eSL_AAA_Eco_FW | GCTAGGAATTCCGCCTCGAGTCCGTTAAAGTGGGTGGAATAGTATACCATTCGTGG | 23 |
| | eSL_AAA_Sph_RV | GATAAGCATGCGCCAAGCTTCGTCAGAGTAGGTGGGATACTATAC-CACGAATGGTATAC | 24 |
| eSLr_AAA | eSLr_AAA_Eco_FW | GCTAGGAATTCCGCCTCGAGTCCGTTTCTGTGGGTGGAATAGTATACCATTCGTGG | 25 |
| | eSLr_AAA_Sph_RV | GATAAGCATGCGCCAAGCTTGGTCTTTGTAGGTCGGATACTATAC-CACGAATGGTATAC | 26 |
| | eSL_AAA_T7F | CTAATACGAGTCACTATAGGGGCGAAAGGGGGATG | 27 |
| | eSL_AAA_RV | GCATGCGCCAAGCTTC | 28 |
| sADg-rGFP_AAA | sADg-rGFP_AAA_T7F | CTAATACGACTCACTATAGGGAAGCACTGCACGCC | 29 |
| | sADg-rGFP_AAA_RV | AGGTGGGATACTATACCACGAATGGTATACTATTC-CACCCGCAGAGGCGTCCAGTGCTTC | 30 |
| ADg (L1) | sADg-rGFP_A200_01_T7F | CTAATACGACTCACTATAGGGAAGCACTGCACGCCGCAGTGGGTG | 31 |
| | sADg-rGFP_A200_01_RV | GTAGGTGGGATACTATACCACGAATGGTATACTATTCCACCCACTGCGGCG | 32 |
| ADg (L2) | sADg-rGFP_A200_02_T7F | CTAATACGACTGACTATAGGGAAGCACTCCACGCCGCAGTGGGTG | 33 |
| | sADg-rGFP_A200_02_RV | TAGGTGGGATACTATACCACGAATGGTATACTATTCCACCCACTGCGGCG | 34 |
| ADG (L4) | sADg-rGFP_A200_04_T7F | GTAATACGACTCACTATAGGGAAGCACTGCACGCCGCAGCTGGTC | 35 |
| | sADg-rGFP_A200_04_RV | GGTGGGATACTATACCACGAATGGTATACTATTCCACCAGGTGCGGCG | 36 |

TABLE 2-continued

DNA oligonucleotides
for in vitro synthesis of ADg-RNA

| target | name | sequence (5'→3') | SEQ ID NO: |
|---|---|---|---|
| ADg (L5) | sADg-rGFP_A200_05_T7F | CTAATACGACTCACTATAGGGAAGCACTGCACGCCGCAGCTCGTG | 37 |
|  | sADg-rGFP_A200_05_RV | GTGGGATACTATACCACGAATGGTATACTATTCCACGAGCTGCGGCG | 38 |
| sAD-rGFPex_AAA | sADg-rGFPex_AAA_RV | CCTGAAGGTGGGATACTATACCACG | 39 |
| GFPs RNA | GFPs RNA_T7F | GTAATACGACTCACTATAGGGTGAATGGCCACAAGTTCAG | 40 |
|  | GFPs RNA_RV | TAGCGTGAGAAGCACTGCAC | 41 |
| Rluc W104X RNA | Rluc W104X_Eco_FW | GCTAGGAATTCACCATGGGTTGCAAGGTGTAC | 42 |
|  | Rluc W104X_Bam_RV | GAAGGATCCTTACTGCTCGTTCTTC | 43 |
|  | Rluc W1040_FW | CTCACCCCTTAGTTCGAGGTG | 44 |
|  | Rluc W104X_R01 | CAGCTCGAACTAAGCGGTGAG | 45 |
|  | Rluc W104X_Koz_T7F | CTAATACGACTCACTATAGGGACCATGGCTTCCAAGGTGTAC | 46 |
|  | Rluc W104X_R02 | TTACTGCTCGTTCTTCAGCACG | 47 |
| GFP mut | GFPmut RV | GAGAAGCACTGCACGCCTTTGCTCAGGCTGCTG | 48 |

TABLE 3

DNA oligonucleotides
for construction of expression plasmid

| target | name | sequence (5'→3') | SEQ ID NO: |
|---|---|---|---|
| ADg-GFP_A200 | ADg-GFP_A200 F1 | GGGTGGAATAGTATAACAATATGCTAAATGTTGTTATAGTATCC | 49 |
|  | ADg-GFP_A200 R1 | TGACCACCCTGAGCTGCGGAGGTGGGATACTATAACAAC | 50 |
|  | ADg-GFP_A200 F2 | CTAAGATCTGGGTGGAATAGTATAACAATATG | 51 |
|  | ADg-GFP_A200 R2 | CTAAAGCTTAAAAATGACCACCCTGAGGTGCG | 52 |
| ADg-rGFP_A200 | ADg-rGFP_A200 F1 | GGGAAGCACTCCAGGCCGCAGCGGGTGGAATAGTATAACAATATG | 53 |
|  | ADg-rGFP_A200 R1 | AGGTGGGATAGTATAACAACATTTAGCATATTGTTATACTATTC | 54 |
|  | ADg-rGFP_A200 F2 | CTAAGATGGGAAGCACTGCACGCC | 55 |
|  | ADg-rGFP_A200 R2 | CTAAAGCTTAAAAAAGGTGGGATAGTATAAC | 56 |
| sADg-GFP_A200 | sADgGFP F | GCTAGAGATCTGGGTGGAATAGTATACCATTCGTG | 57 |
|  | sADgGFP R | GCTAGAAGCTTAAAAATGACCACCCTGAGCTG | 58 |
| sADg-rGFP_A200 | sADgrGFP F | GATAAAGATCTGGGAAGCACTCCACG | 59 |
|  | sADgrGFP R | GCTAGAAGGTTAAAAAAGGTGGGATACTATACCACG | 60 |
| ADg-rGFP_A173 | ADg-rGFP_A173 F | GCTATAGATCTCTCACCAGGGTGGGCCAGGGGGTG-GAATAGTATAAC | 61 |
|  | ADg-rGFP_A173 R | CCGATAAGCTTAAAAGGTGGGATACTATAACAACATTTAGCAT-ATTGTTATACTATTCCACCC | 62 |
| GFP mRNA W58X | 5'-GFP F | CCATGCTCGAGGGGCCGATGGTGAGC | 63 |
|  | 5'-GFPW58X R | CAGGGTGGGCTAGGGCACAGG | 64 |
|  | 3'-GFPW58X F | CCTGTGCCCTAGCCCACCCTG | 65 |
|  | 3'-GFP R | GGTACAAGCTTTCACTTGTACAGCTCATCCA | 66 |

TABLE 4

DNA oligonucleotides for RT-PCR

| | name | sequence (5'→3') | SEQ ID NO: |
|---|---|---|---|
| RT | oligodT | GGCCACGCGTCCACTAGTACTTTTTTTTTTTTTTTTT | 67 |
| nested PCR 1st | GFP R1 for edit check | GGCCACGCGTCGACTAGTAC | 68 |
| nested PCR 2nd | GFP R2 for edit check | TCACTTGTACAGCTCATCCA | 69 |

TABLE 4-continued

DNA oligonucleotides for RT-PCR

| name | sequence (5'→3') | SEQ ID NO: |
|---|---|---|
| nested PCR 1st and 2nd | GFP F for edit check | CTAATACGACTCACTATAGG GATGGTGAGCAAGGGCGCC | 70 |

TABLE 5

DNA oligonucleotides for qPCR

| target | name | sequence (5'→3') | SEQ ID NO: |
|---|---|---|---|
| ADg-GFP_A200 | sADgrGFP F for qPCR | GAAGCACTGCACGCCG | 71 |
| | sADgrGFP R for qPCR | GGTGGGATACTATACCACG | 72 |
| GAPDH | GapDH F for qPCR | CCTGCACCACCAACTGCTTAGC | 73 |
| | GapDH R for qpCR | GATGGCATGGACTGTGGTCATGAC | 74 |

TABLE 6 sequences of RNA

| NAME | length (nt) | Sequence (5'→3') | SEQ ID NO: |
|---|---|---|---|
| ADg-GFP_A200 RNA | 66 | GGGUGGAAUAGUAUAACAAUAUGCUAAAUGUUGUUAUAGUAUCGCACCUCCGCAGCUCAGGGUGGUCA | 75 |
| 3'-antisense RNA | 19 | CCGCAGCUCAGGGUGGUCA | 76 |
| 5'-antisense RNA | 22 | GGGAAGCACUGCACGCCGCAGC | 77 |
| ADg-rGFP_A200 RNA | 71 | GGGAAGCACUGCACGCCGCAGCGGUGGAAUAGUAUAAGAAUAUGCUAAAUGUUGUUAUAGUAUCGCACCU | 78 |
| AD-guide rRluc_A311 RNA | 62 | GGGUUGAGCAGCUCGAACCAAGGGGUGGAAUAGUAUACCAUUCGUGGUAUAGUAUCCCACCU | 79 |
| sADg-GFP_A200 RNA | 59 | GGGUGGAAUAGUAUACCAUUCGUGGUAUAGUAUCCCACCUCCGCAGCUCAGGGUGGUCA | 80 |
| sADg-rGFP_A200 RNA | 62 | GGGAAGCACUGCACGCCCCAGCCGGUGGAAUAGUAUACCAUUCGUGGUAUAGUAUCCCACCU | 81 |
| sADg-rGFP_AAA | 62 | GGGAAGCAGUGCACGCCUCUGCGGGUGGAAUAGUAUACCAUUCGUGGUAUAGUAUCCCACCU | 82 |
| sADg-rGFPex_AAA | 85 | GGGAAGCACUGCACGCCUCUGCGGGUGGAAUAGUAUACCAUUCGUGGUAUAGUAUCCCACCUUCAGG | 83 |
| sADg-rGFP_A200_0 | 65 | GGGAAGCACUGCACGCCGCGGUGGGUGGAAUAGUAUACCAUUCGUGGUAUAGUAUCCCACCUACC | 84 |
| ADg (L1) | 64 | GGGAAGGAGUGCACGCCGCAGUGGGUGGAAUAGUAUACCAUUCGUGGUAUAGUAUCCCACCUAC | 85 |
| ADg (L2) | 63 | GGGAAGCACUGCACGCCGCAGUGGGUGGAAUAGUAUACCAUUCGUGGUAUAGUAUCCCACCUA | 86 |

TABLE 6-continued sequences of RNA

| NAME | length (nt) | Sequence (5'→3') | SEQ ID NO: |
|---|---|---|---|
| ADg (L4) | 61 | GGGAAGCACUGCACGCCGCAGCUGGUGGAAUAGUAUACCAUUCGUG-GUAUAGUAUCCCACC | 87 |
| ADg (L5) | 60 | GGGAAGCACUGCACGCCGCAGCUCGUGGAAUAGUAUACCAUUCGUG-GUAUAGUAUCCCAC | 88 |
| ADg-rGFP_A173 | 69 | GUCACCAGGGUGGGCCAGGGGGUGGAAVAGUAUAACAAUAUGCUAAAU-GUUGUUAUAGUAUCCCACCUU | 89 |
| sADgGFP | 61 | GGGUGGAAUAGUAUACCAUUCGUGGUAUAGUAUCCCACCUCCGCAG-CUCAGGGUGGUCAUU | 90 |
| sADgrGFP | 64 | GGGAAGCACUGCACGCCGCAGCGGGUGGAAUAGUAUACCAUUCGUG-GUAUAGUAUCCCACCUUU | 91 |
| GFP RNA | 720 | AUGGUGAGCAAGGGCGCCGAGCUGUUCACCGGCAUCGUGCCCAUC-CUGAUGGAGCUGAAUGGCGAUGUGAAUGGC-CACAAGUUCAGCGUGAGCGGCGAGGGCGAGGGCGAUGCCACCUACGGCAAGCUGACCCUGAAGUUCAUCUGCAC-CACCGGCAAGCUGCCUGUGCCCUGGCCCACCCUGGUGACCACCCUGAGC-UACGGCGUGCAGUGCUUCUCACGCUACCCCGAUCACAUGAAGCAGCACGACUUCUU-CAAGAGCGCCAUGCCUGAGGGCUACAUCCAGGAGCGCACCAUCUUCUUCGAG-GALGACGGCAACUACAAGUCGCGCGCCGAGGUGAAGUUCGAGGGCGAUACCCUGGUGAAUCG-CAUCGAGCUGACCGGCACCGAUUUCAAGGAGGAUGGCAACAUC-CUGGGCAAUAAGAUGGAGUACAACUACAACGCCCACAAUGUGUACAUCAUGACCGACAAGGC-CAAGAAUGGCAUCAAGGUGAACUUCAAGAUCCGCCACAACAUCGAG-GAUGGCAGCGUGCAGCUGGCCGACCACUACCAGCAGAAUACCCCCAUCGGCGAUGGCCCU-GUGCUGCUGCCCGAUAACCACUACCUGUCCACCCAGAGCGCCCUGUC-CAAGGACCCCAACGAGAAGCGCGAUCACAUGAUGUACUUCGGCUUCGUGACCGCCGCCGC-CAUCACCCACGGCAUGGAUGAGCUGUACAAGUGA | 92 |
| GFPs RNA | 160 | GGGUGAAUGGCCACAAGUUCAGCGUGAGCGGCGAGGGCGAGGGCGAUCC-CACCUACGGCAAGCUGACCCUGAAGUUCAUCUGCACCACCGGCAAGCUGCCU-GUGGCCUGGCCCACCCUGGUGACCACCCUGAGCUACGGCGUGCAGUGCUUCU-CACGCUA | 93 |
| Rluc W104X RNA | 942 | GGGACCAUGGCUUCCAAGGUGUACGACCCCGAGCAACGCAAACGCAUGAU-CACUGGGCCUCAGUGGUGGGCUCGCUGCAAGCAAAUGAACGUGCUGGACUCC-UUCAUCAACUACUAUGAUUCCGAGAAGCACGCCGAGAACGCCGUGAUUUUUGUG-CAUGGUAACGCUGGCUCGAGGUACCUGUGGAGGCACGUCGUGCCUCA-CAUCGAGCCCGUGGCUAGAUGCAUCAUGCCUGAUCUGAUCGGAAUGGGUAAGU-CCGGCAAGAGCGGGAAUGGCUCAUAUCGCCUCCUGGAUCACUAGAAGUACCUCACCGC-UUAGUUCGAGCUGCUGAACCUUCCAAAGAAAAUCAUCUUUGUGGGC-CACGACUGGGGGGCUUGUCUGGCCUUUCACUACUCCUACGAGCACCAAGACAAGAU-CAAGGCCAUCGUCCAUGCUGAGAGUGUCGUGGACGUGAUCGAGUC-CUGGGACGAGUGGCCUGACAUCGAGGAGGAUAUCGCCCUGAU-CAAGAGCGAAGAGGGCGAGAAAAUGGUGCUUGAAUAACUUCUUCGUGGAGACCAUGCUCCCAAGCAAGAU-CAUGCGGAAACUGGAGCUGAGGAGUUCGCUGCCUACCUGGAGCCAUU-CAAGGAGAAGGGC | 94 |

TABLE 6-continued sequences of RNA

| NAME | length (nt) | Sequence (5'→3') | SEQ ID NO: |
|---|---|---|---|
| | | GAGGUUAGACGGCCUACCCUCUCCUGGCCUCGCGAGAUCGCUCUCGUUAAGGG<br>AGGCAAGCCCGACGUCGUCCAGAUUGUCCGCAACUACAACGCCUACCUUUGGG<br>CCAGCGAGGAUCUGCCUAAGAUGUUCAUCGAGUCCGACCCUGGGUUCUUUUCC<br>AACGCUAUUGUCGAGGGAGCUAAGAAGUUCCCUAACACCGAGUUCGUGAAGGU<br>GAAGGGCCUCCACUUCAGCCAGGAGGACGCUCCAGAUGAAAUGGGUAAGUACA<br>UCAAGAGCUUCGUGGAGCGCGUGCUGAAGAACGAGCAGUAA | |
| eSL_AAA RNA | 196 | GGGGGCGAAAGGGGGAUGUGCUGCAAGGCGAUUAAGUUGGGUAACGCCAGGGU<br>UUUCCCAGUCACGACGUUGUAAAACGACGGCCAGUGAAUUCCGCCUCGAGUCC<br>GUUAAAGUGGGUGGAAUAGUAUACCAUUCGUGGUAUAGUAUCCCACCUACUCU<br>GACGAAGCUUGGCGCAUGC | 95 |
| eSLr_AAA RNA | 196 | GGGGGCGAAAGGGGGAUGUGCUGCAAGGCGAUUAAGUUGGGUAACGCCAGGGU<br>UUUCCCAGUCACGACGUUGUAAAACGACGGCCAGUGAAUUCCGCCUCGAGUCC<br>GUUUCUGUGGGUGGAAUAGUAUACCAUUCGUGGUAUAGUAUCCCACCUACAAA<br>GACGAAGCUUGGCGCAUGG | 96 |
| GFPmut RNA | 154 | GGGUGAAUGGCCACAAGUUCAGCGUGAGCGGCGAGGGCGAGGGCGAUGCCACC<br>UACGGCAAGCUGACCCUGAAGUUCAUCUGCACCACCGGCAAGCUGCCUGUGCC<br>CUGGCCCACCCUGGUGACCACCCUGAGCAAAGGCGUACAGUGCUUCUC | 97 |
| AcGFP W58X RNA | 720 | AUGGUGAGCAAGGGCGCCGAGCUGUUCACCGGCAUCGUGCCCAUCCUGAUCGA<br>GCUGAAUGGCGAUGUGAAUGGCCACAAGUUCAGCGUGAGCGGCGAGGGCGAGG<br>GCGAUGCCACCUACGGCAAGCUGACCCUGAAGUUGAUCUGGACCACCGGCAAG<br>CUGCCUGUGCCCUAGCCCACCCUGGUGACCACCCUGAGCUACGGCGUGCAGUG<br>CUUCUCACGCUACCCCGAUCACAUGAAGCAGCACGACUUCUUCAAGAGCGCCA<br>UGCCUGAGGGCUACAUCCAGGAGCGCACCAUCUUUCUUCGAGGAUGACGGCAA<br>CUACAAGUCGCGCGCCGAGGUGAAGUUCGAGGGCGAUACCCUGGUGAAUCGCA<br>UCGAGGUGACCGGCACCGAUUUCAAGGAGGAUGGCAACAUCCUGGGCAAUAAG<br>AUGGAGUACAACUACAACGCCCACAAUGUGUACAUCAUGACCGACAAGGCCAA<br>GAAUGGCAUCAAGGUGAACUUCAAGAUCCGCCACAACAUCGAGGAUGGCAGCG<br>UGCAGCUGGCCGACCACUACCAGCAGAAUACCCCCAUCGGCGAUGGCCCUGUG<br>CUGCUGCCCGAUAACCACUACCUGUCCACCCAGAGCCCCCUGUCCAAGGACCC<br>CAACGAGAAGCGCGAUCACAUGAUCUACUUCGGCUUCGUGACCGCCGCCGCCA<br>UCACCCACGGCAUGGAUGAGCUGUACAAGUGA | 98 |

Method for Preparing AD-gRNA and Target RNA

First, AD-gRNA was synthesized by the in vitro transcription method. A template dsDNA for in vitro transcription was synthesized by a common method using synthetic oligonucleotides. In general, 1 µM of the forward DNA oligonucleotide containing a T7 promoter sequence and 1 µM of a reverse DNA oligonucleotide were mixed in an annealing buffer (50 mM Tris-HCl [pH 7.6], 50 mM NaCl), after which an annealing reaction was performed by denaturing at 90° C. for 3 min, followed by cooling at room temperature for 15 min. To generate the dsDNA template, the annealed product was elongated using Klenow polymerase (New England BioLabs). The obtained dsDNA was purified by phenol/chloroform extraction and ethanol precipitation. Using this purified dsDNA as a template, an in vitro transcription reaction was performed using the AmpliScribe T7 kit (Epicenter Biotechnologies) according to the manufacturer's protocol. The reaction solution was subjected to phenol/chloroform extraction and ethanol precipitation, and denatured on 5% polyacrylamide gel containing 8 M urea to purify AD-gRNAs. The target RNA was prepared by PCR using dsDNA template by a standard PCR reaction (PrimeSTAR GXL DNA polymerase (Takara Bio)). Subsequently, in vitro transcription and purification were performed as described above. The sequences of all DNA oligonucleotides and RNA samples are shown in Tables 2 to 6.

Preparation Method of Recombinant hADAR2

Recombinant hADAR2 was prepared by amplifying the coding region for human ADAR2 from cDNA clone (clone ID 6014605. Open Biosystems) by PCR, cloning the N-terminal His-Express tagged fusion protein, and transforming it into INVScl yeast cells using the Frozen-EZ Yeast Transformation 11 Kit (Zymo Research). The obtained transformants were cultured in a liquid medium, and the recombinant hADAR2 was purified using a HisTrap HP column (GE Healthcare). Fractions containing hADAR2 were collected and dialyzed against a buffer for storage (10 mM Tris-HCl [pH 7.5], 150 mM NaCl, 5% glycerol, 1 mM DTT) using a 50-kDa molecular weight cutoff Float-A-Lyzer G 2 Spectra/Por). Purified hADAR2 was quantified using DC protein Assay Kit (BioRad) according to the manufacturer's protocol.

EXAMPLE 11

In Vitro Editing Assay

Complexes of gRNAs and target RNA were prepared by heating 900 nM AD-gRNA and 300 nM target RNA at 80° C. for 3 min. and then slowly cooling in an annealing buffer (10 mM Tris-HCl [pH 7.6], 150 mM NaC) to 25° C. at a rate of 1° C./10 sec. The editing reaction was carried out as follows: 5 nM of the obtained complex and purified hADAR2 with various concentrations were mixed in 20 µl of a reaction buffer (20 mM HEPES-KOH [pH 7.5], 100 mM NaCl, 2 mM MgCl 2, 0.5 mM DTT, 0.01% Triton X-100, 5% glycerol, 1 U/µl Murine RNAse Inhibitor [New England BioLabs]), and then incubated at 37° C. for 2 hours. After completion of the reaction, the reacted RNA was subjected to phenol/chloroform extraction/ethanol precipitation. Thereafter, the RNA pellet was dissolved in 5 µl TE buffer. To obtain cDNA from the reacted RNA from the purified RNA, it was reverse transcribed using PrimeScript II Reverse Transcription Kit (Takara Bio). cDNA was PCR-amplified using PrimeSTAR GXL DNA polymerase (Takara Bio) according to a standard protocol. Male and female efficiencies at each site were analyzed by direct sequencing as follows. 10 ng of gel purified PCR product was sequenced with a reverse primer and the BigDye Terminator Cycle Sequencing Kit (Applied Biosystems), and then sequencing chromatography was performed with 3130 Genetic Analyzer (Applied Biosystems). The editing ratio at each site was calculated as follows: A/(A+G) (where A and G are peak heights of adenosine and guanosine measured by Sequence Scanner software ver. 1.0 (Applied Biosystems)).

EXAMPLE 12

In Vitro Codon Repair Experiments Using a Luciferase Reporter Assay Coupled with In Vitro Translation The reporter for the in vitro codon repair experiment was designed based on *Renilla* luciferase mRNA (Rluc-WT). This reporter mRNA (Rluc-W104X) was prepared by mutating G 311 to A311 in Trp 104 (UGG) using QuikChange Site-Directed Mutagenesis Kit (Stratagene). With this Rluc-W104X reporter, the full length, wild type Rluc transcript was synthesized and A311 was edited to I 311. In vitro compilation reaction and translation reaction were carried out continuously. First, 5 µM Rluc-W104X and 15 µM ADg-rLuc_A311 were annealed by heating together at 80° C. for 3 min in an annealing buffer and then slow cooling to 25° C. at a rate of 1° C./10 sec. Thereafter, 0.5 µM of the reporter/gRNA complex was treated in a reaction buffer at 37° C. for 2 hours to perform an editing reaction with 1.25 µM hADAR2. In parallel, a control sample (without gRNA) was treated in the same reaction.

The edited RNA sample was extracted with phenol/chloroform and recovered by ethanol precipitation. To assess whether active Rluc could be translated from edited reporter mRNA, an in vitro translation was performed in 20 µl of rabbit reticulocyte lysate, using 1 µg of reporter RNA obtained from the editing reaction. After 1 hour of translation at 37° C., chemiluminescence was performed using the Dual-Luciferase Reporter Assay System (Promega) according to the manufacturing protocol, and luminescence was measured with a spectrophotometer. When performing the reaction at the same time, 5 µM Rluc-W104X, 15 µM ADg-rLuc_A311, and 1.25 µM hADAR2 were thoroughly mixed with 20 µl of rabbit reticulocyte lysate and incubated at 37° C. for 20 min. Luciferase assay was then performed under the conditions described above.

EXAMPLE 13

Preparation of AD-gRNA Expression Plasmid

An AD-gRNA expression plasmid was constructed using pSUPER.neo (Oligoengine), which is used for expressing intracellular RNAs such as short hairpin RNAs and miR-NAs, based on the HI RNA polymerase III promoter. While preparing DNA insert-encoding AD-gRNAs, tetra uridine was inserted into the 3' end of the AD-gRNA sequence to terminate pol III transcription at a specified position. Cloning into vectors was facilitated by introducing Hind III and Bgl II restriction sites at the 5' and 3' ends, respectively. The DNA inserts were prepared using synthetic oligonucleotides shown in Tables 2 to 6. Each DNA insert was cloned into the pSuper.neo vector and the sequences of the resulting plasmids were confirmed by DNA-sequencing analysis. Finally, expression plasmid used for transcription was prepared using a Plasmid Mini Kit (Qiagen) according to the manufacturer's protocol.

EXAMPLE 14

Cell Culture

HEK 293 cells were collected in Dulbecco's Modified Eagle Medium (DMEM; Sigma) supplemented with 10% fetal bovine serum. Tet-ADAR2 cells, in which hADAR2 and AcGFP were simultaneously expressed from a bidirectional promoter under the control of the Tet-on system, were established in the inventors' laboratory. tet-ADAR2 cells were cultured as monolayers in DMEM supplemented with 10% Tet system-approved fetal bovine serum (Clontech), 1 µg/mL puromycin and 100 µg/mL G418 (Sigma) at 37° C. in the presence of 5% $CO_2$. The expression of ADAR2 and AcGFP was induced by culturing tet-ADAR2 cells in the above medium supplemented with 5 µg/mL of Dox.

EXAMPLE 15

Analysis of Intracellular Activity of AD-Guide RNAs

Tet-ADAR2 cells ($1.6 \times 10^5$) were added to 35-mm dishes containing a medium containing 5 µg/mL Dox. When the cells reached about 80% confluence, they were transfected with 2 µg of AD-gRNA using X-treme GENE HP DNA Transfection Reagent (Roche). After transfection for 72 hours, the editing efficiency at A100 in AcGFP RNA, which was simultaneously expressed with hADAR2 in tet-ADAR2 cells, was analyzed as follows. Total RNA was extracted from the transfected cells using Sepasol RNA I Super G (Nacalai Tesque) according to the manufacturer's protocol. Thereafter, the RNA samples (30 µg) were treated with 10 U DNase I (Takara Bio) at 37° C. for 3 hours, followed by phenol/chloroform extraction and ethanol precipitation. Purified RNA (0.5 µg) was reverse transcribed using the adapter link oligo (dT) 17 primer and Transcriptor High Fidelity cDNA Synthesis Kit (Roche) according to the manufacturer's protocol. Using the obtained total RNA as a template. AcGFP cDNA was amplified by PCR using AcGFP-specific primers (AcGFP_F and AcGFP_R). The efficiency of AI RNA editing at the A100 site was analyzed by direct sequencing, followed by quantification of the relative heights of the A and G peaks, after which each editing ratio was calculated on the basis of the peak height of G divided by that of (A+G).

EXAMPLE 16

Intracellular Codon Repair Experiments with AD-gRNAs

In the in vitro codon repair experiments, the mutant GFP mRNA (AcGFP-W58X) in which G173 was changed to A173 and codon W58 of the stop codon was mutated was designed to determine whether AD-gRNA could regulate functional gene expression in cells. The AcGFP-W58X expression plasmid was constructed based on the pcDNA 3.1 expression vector (Invitrogen). In addition, hADAR2 expression plasmid was constructed by cloning PCR-amplified hADAR2 cDNA into pcDNA 3.1. 100 ng each of hADAR2, AcGFP-W58X and AD-gRNA expression vectors were co-transfected into sub-confluent HEK 293 cells. The editing efficiency was analyzed 72 hours after transfection. The recovery of intracellular GFP fluorescence was analyzed with a fluorescence microscope.

EXAMPLE 17

Figure 36:
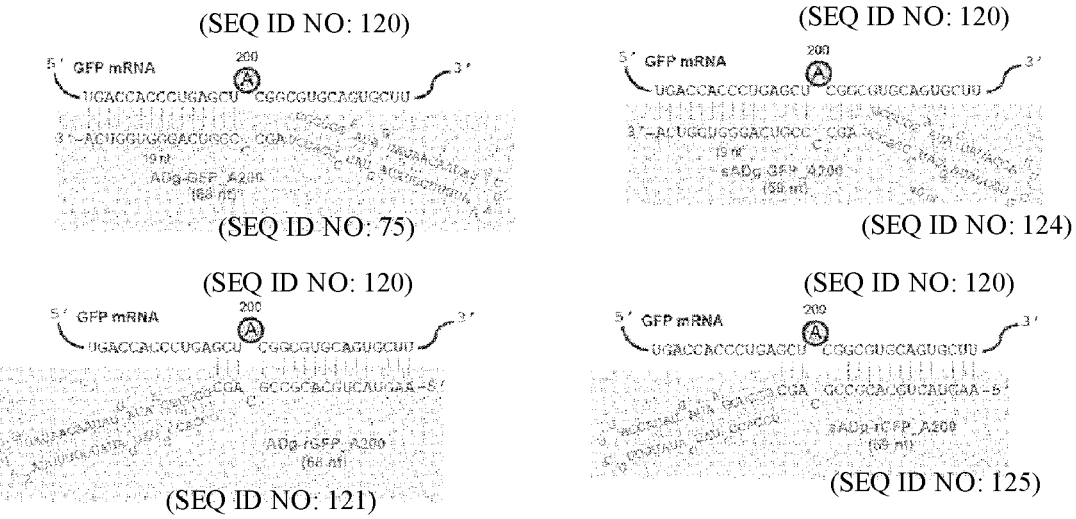
FIG. 36 shows sequences of four editing guide RNAs (ADg-GFP_A200, ADg-rGFP_A200, sADg-GFP_A200, sADg-rGFP_A200) used in the experiment.
Figure 37:
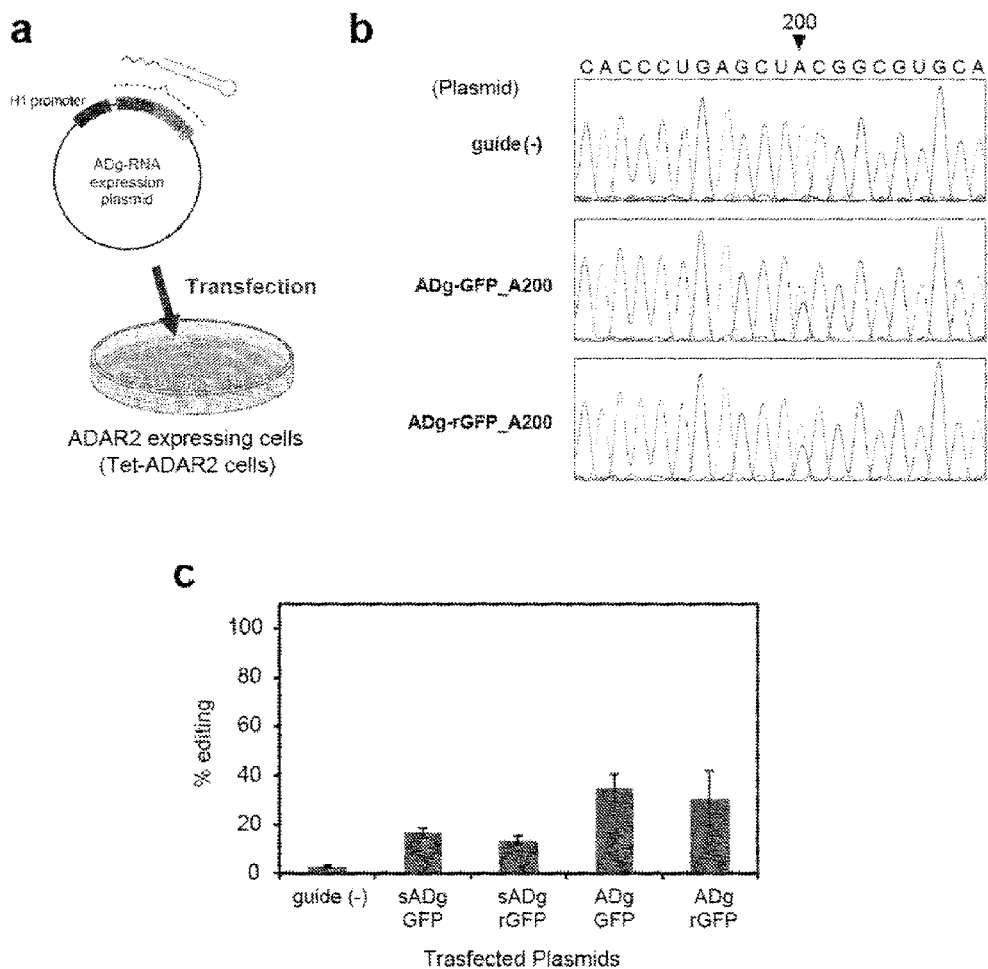
FIG. 37 shows RNA mutagenesis by the above editing guide RNA: (a) is a diagram showing an outline of experiments; (b) is a diagram showing the results of compilation and analysis of GFP mRNA by direct sequencing; (c) is a graph showing the editing percentage of A200 obtained from the peak height.

This example is an example of verifying whether the editing guide RNA according to the present invention functions in cultured cells into which intracellular RNA mutation has been introduced. First, intracellular expression plasmids of four editing guide RNAs (ADg-GFP-A200, ADg-rGFP_A200, sADg-GFP-A200, sADg-rGFP_A200: see FIG. 36) which showed editing-inducing activity in vitro were constructed. As an expression vector, commercially available pSUPER.neo (Oligoengine) was used. In addition, tet-ADAR2 cells (a cell line constructed by incorporating an ADAR2 expression gene in HEK 293 cells, expressing ADAR 2 and GFP dependent on doxycycline concentration) were used as ADAR expressing cells. After tet-ADAR2 cells were cultured in the presence of doxycycline to induce expression of ADAR2 and GFP, various editing guide RNA expression plasmids were introduced (FIG. 37a). After cultivation, the editing ratio of the target site A200 (see FIG. 21) was analyzed based on the edit analysis result of GFP mRNA by direct sequencing. In other words, the GFP mRNA extracted from the cells was reverse transcribed, and the sequence analysis was carried out. As a result, in the A200 of the GFP RNA extracted from the cells, a signal of editing was detected only when the editing guide RNA was introduced (FIG. 37b). In addition, as a result of calculation from the ratio (G/A+G) of the height of the peak of the chromatographic chart at that time, the editing ratio at that time was about 40% edited in a high sample (FIG. 37c). From the above results, it was demonstrated that editing guide RNA can induce intracellular ADAR and introduce mutation at a target site. In addition, this result also shows that, if cells expressing ADAR, mutagenesis can be performed in a targeted manner only by plasmid introduction.

EXAMPLE 18

Since inosine (I) on mRNA is recognized as guanosine (G) at the time of translation, the function of intracellular target protein can be controlled by codon modification by this A-I mutation. Thus, in this example, it was clarified whether the method of introducing a RNA mutation according to the present invention can control expression of protein function.

Figure 38:
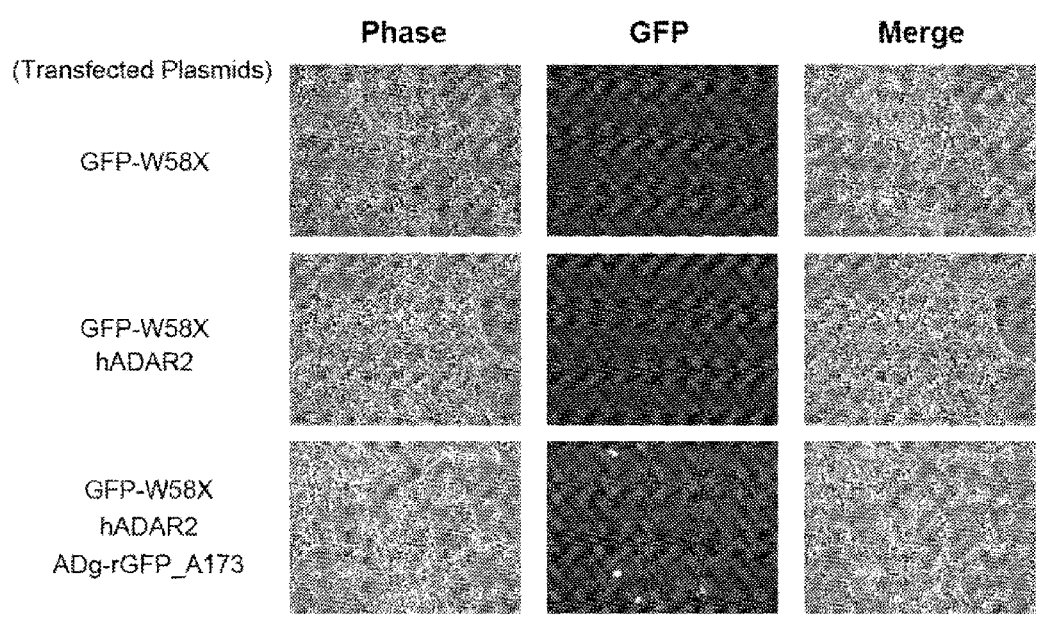
FIG. 38 is a view showing the transmitted light of the cells after the introduction of the editing guide RNA and observation results by a fluorescence microscope.

Specifically, a reporter mRNA (GFP W58X mRNA) in which the 58$^{th}$ Trp codon (UGG) of GFP mRNA (720 nt) was modified to a stop codon (UAG) was used to mutagenize the stop codon into UIG so as to verify whether mature GFP is translated in cells (FIG. 37a). First, in order to modify the target termination codon to the Trp codon, an editing guide RNA (ADg-rGFP A173) targeting A173 was designed and an intracellular expression plasmid was constructed using pSuper.neo. After that, cotransfection was carried out with ADAR2 expression plasmid (pcDNA3.1 (−) Hygro_His-ADAR2), reporter RNA expression plasmid (pcDNA3.1 (−) Hygro_AcGFPW 58X), and HEK 293 cells. After cultivation, cells emitting fluorescence by editorial induction were confirmed by fluorescence microscopy. As a result, cells emitting intense fluorescence were detected only in the cell group into which the editing guide RNA expression plasmid was introduced (FIG. 38). The above results demonstrate that expression of the target protein can be controlled by introducing an RNA mutation using the editing guide RNA.

EXAMPLE 19

$4.0 \times 10^5$ Tet-ADAR 2 cells were cultured in Tet serum medium containing 1 µg/mL puromycin, 100 µg/mL G418, and 5.0 µg/mL Dox in a collagen-coated 35-mm dish under the conditions of 37° C. and 5.0% $CO_2$. Cells cultured to 80% confluence were subcultured to a 6-well plate at $1.6 \times 10^5$ cells/well. After incubation for 48 hours, each guide RNA expression plasmid (pSuper-guide 3-mini, pSuper-guide 3r-mini, pSuper-guide 3-Glu, pSuper-guide 3r-Glu) was transfected using FuGENE HP Transfection Reagent (Roche), and transfected for 72 hours. Thereafter. RNA was all extracted using 1000 µL of Cepazole RNA I Super G (Nacalai), and DNase treatment was performed for 1 hour at 37° C. using 10 U Recombinant DNase I (TaKaRa). RNA products were all purified by phenol/chloroform treatment, and ethanol precipitation in the presence of sodium acetate. A reverse transcription reaction was carried out for the following conditions: denaturing at 80° C. for 3 min, rapid cooling and annealing at 65° C. for 10 min, elongation reaction at 55° C. for 300 min, and heating at 85° C. for 5 min, using 0.5 µg of total RNA, 2.5 µM Oligo (dT) 17, and Transcriptor First Strand cDNA Synthesis Kit (Roche) to synthesize cDNA. 1st PCR (denaturation at 98° C. for 10 sec, annealing at 55° C. for 15 sec, elongation reaction at 68° C. for 60 sec, 35 cycles) was carried out using the sample diluted 10 times as a template with 0.25 µM AcGFP RNAf T7F01 primer, 0.25 µM 3'-ADP primer, 0.25 U PrimeStar GXL DNA polymerase (TaKaRa). Using the 1st PCR product diluted 400 times as a template, Nested PCR (denaturation at 98° C. for 10 sec, annealing at 55° C. for 15 sec, elongation reaction at 68° C., 60 sec, 24 cycles) was carried out with 0.25 µM RNAf T7F01 primer and 0.25 µM AcGFP- RNAf-R 01 primer. After the PCR reaction, a sequencing reaction (denaturation at 96° C. for 10 sec. annealing at 50° C. for 5 sec, elongation reaction at 60° C. for 30 sec, 25 cycles) was carried out using Big Dye Terminator v3.1 Cycle Sequencing Kit (Applied Biosystems™) and 0.165 µM RNAf T7F01 primer using the amplification product diluted 10 times. The editing ratio was calculated from the obtained peak height ratio G/(G+A). The subsequent operation (after RNA extraction) was performed in the same manner as described above.

EXAMPLE 20

$1.6 \times 10^5$ HEK 293 cells were cultured in serum medium at 35° C./GLASS BASE DISH (Glass 12φ) (Iwaki) for 48 hours under conditions of 37° C. and 5.0% $CO_2$. Thereafter, 700 ng each of ADAR2 expression plasmid pcDNA3.1 (−) Hygro_His-ADAR2, substrate RNA expression plasmid pcDNA3.1 (−) Hygro_AcGFPW58X and each guide RNA expression plasmid pSuper-neo-guide 3r-miniW 58X or pSuper-neo-guide 3r-GluW 58X were transduced using X-tremeGENE HP DNA Transfection Reagent (Roche) and cultured for 72 hours. After that, the cells were washed with D-PBS (−) (Nacalai) and then observed using a confocal fluorescence microscope.

EXAMPLE 21

Figure 23:
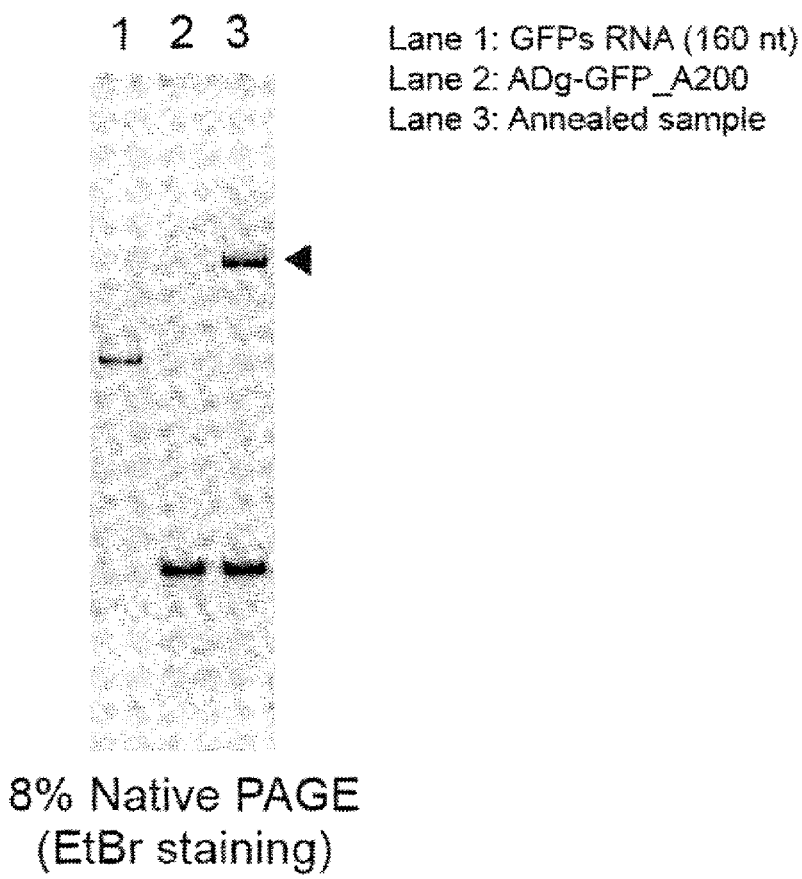
FIG. 23 shows gel mobility shift assay results for confirming formation of a complex of an AD-gRNA and a target RNA.

In this example, formation of a complex of AD-gRNA and target RNA was confirmed by a gel-mobility shift assay (FIG. 23). After annealing the ADg-GFT A200 (900 nM) and the GFP mRNA fragment (300 nM; 160 nt) at 80° C. for 3 min, it was gradually cooled in the annealing buffer (10 mM Tris-HCl [pH 7/6], 150 mM NaCl) to 25° C. at a rate of 1° C. for 10 sec. After cooling slowly, it was electrophoresed with 8% polyacrylamide and stained with ethidium bromide. The first lane shows GFP RNA, the second lane shows ADg-GFP-A200, and the third lane shows samples annealed. The shifted band can be considered to be the obtained conjugate as indicated by arrowhead marks.

EXAMPLE 22

In this example, the construction of AD-gRNA using a framework based on edited GAuR2 RNA was confirmed (FIG. 24). The in vitro compilation activity of sADg-GFP_A200 and sADg-rGFP A200 was obtained by calculating the editing ratio from the A and G peaks in the sequencing chromatogram of GFP cDNA. The sequencing chromatogram was obtained by in vitro compilation reaction without gRNA (upper panel), or sADg-GFP_A200 (middle panel) or sADg-rGFP A200 (lower panel) after RT-PCR. Results are presented as mean and standard deviation values from 3 independent experiments.

EXAMPLE 23

In this example, editing specificity was analyzed using cis-substrate RNA (FIG. 25). In order to investigate the editing specificity of substrate RNA, eSL_AAA RNA and eSLr_AAA RNA were designed based on the substrate hairpin structure using the following mutation.

The eSL_AAA RNA was generated by mutating the nucleotide adjacent to the targeted editing site to adenosine and introducing uridine into the complementary position of this mutant adenosine to promote base pairing. eSLr_AAA RNA was generated by replacing three adenosines containing the target base adenosine of eSL_AAA RNA with complementary nt. The actual sequences of eSL_AAA RNA and eSLr_AAA RNA are shown in FIG. 25(a). In the figure, in order to facilitate recognition of each adenosine, the target editing site is shown at the nt position (0), the adjacent 5'-adenosine is shown at the nt position (−1), and the 3'-adenosine is shown at the nt position (+1).

Using these substrate RNAs, an in vitro editing reaction with hADAR2 was performed according to the method of FIG. 23a. Next, the editing efficiency of the target adenosine was analyzed by the direct sequencing method with varying reaction time. The obtained sequence chromatogram is shown in FIG. 25(b). In the figure, the position of each adenosine is represented by the corresponding nt position number. In addition, the editing ratio calculated from the peak height was plotted for each reaction time on a graph. In the figure, circles indicate editing percentages observed at the nt position (0), square marks and triangle marks represent editing percentages observed at the nt positions (−1) and (+0), respectively. The data are the mean and standard deviation of the results of three independent experiments.

EXAMPLE 24

In this example, in order to evaluate the flanking specificity of AD-gRNA induced RNA compilation, GFP mut RNA was generated by mutating adjacent nt adjacent to A200 in GFP mRNA to adenosine. In FIG. 26, ntA200 was defined as nt position 0, and 5' side and 3' side adenosines were defined as nt−1 and nt+1, respectively. For ADg-RNA, ADg-rGFT_AAA was constructed according to the sequence design of ADg-rGFP_A200. FIG. 26a shows the sequence design around the targeted editing site on GFPmut RNA and the actual nucleotide sequence of ADg-rGFP_AAA. In order to analyze the editing efficiency at each site, an in vitro editing reaction was performed according to FIG. 23. Changes in editing efficiency according to differences in editing time were plotted on a graph. In the graph, the circle, triangle, and square marks represent editing percentages at nt positions 0, +1 and −1, respectively. The data are the mean and standard deviation of the results of three independent experiments.

EXAMPLE 25

In the present example, the adjacent specificity of AD-g RNA-induced RNA editing and the effect on editing efficiency when base pairing was additionally introduced were analyzed. The degree of rotational freedom of the ADAR binding site (FIG. 25) in sADg-rGFP_AAA was investigated to see whether it could be suppressed by additionally introducing base pairing on the 3' side. 5 nt (5'-UCAGG-3') was further introduced on the 3' side of sADg-rGFP_AAA to design to extend base pairing region (boxed region). In vitro editing reaction with hADAR2 was performed under the same conditions as in Example 24, and the editing percentage at each site was analyzed.

EXAMPLE 26

In this example, a simultaneous in vitro editing/translation reaction was performed. FIG. 30a is a schematic view of the reaction. FIG. 30b shows the results of analyzing the editing efficiency at A311 by direct sequencing after the reaction. The top panel shows the sequence chromatogram without guide RNA, and the bottom panel shows the sequence chromatogram of ADg-rRluc_A311.

EXAMPLE 27

In this example, ADg-GFP A200 in tet-ADAR 2 cells was subjected to RT-PCR and quantitative PCR (qPCR). Subconfluent proliferating tet-ADAR2 cells were transfected with the AD-gRNA expression plasmid vector. After incubation for each time, total RNA was extracted and reverse transcription was performed using a random hexamer primer (dN 6 primer) using Transcriptor High Fidelity cDNA Synthesis Kit (Roche). qPCR was performed using qADg_F and qADg_R primers for specific amplification of ADg-GFP-A200 using Power SYBR (R) Green PCR Master Mix (Applied Biosystems). Glyceraldehyde 3-phosphate dehydrogenase (GAPDH) was also quantified using GAPDA-QF and GAPDH-QR primers as an internal standard for quantifying the total RNA amount. The conditions of qPCR are as follows: preheating for denaturation (95° C. for 10 min) and amplification by LightCycler Nano System (Roche) (95° C., 15 sec; 60° C., 1 min: 55 cycles). Using an analysis software, a tolerance threshold (Ct: crossing threshold) was calculated from the fluorescence amplification plot by the 2nd derivative maximum method. The tolerance threshold difference (ΔCt) of each sample was calculated as follows:

ΔCt=Ct(AD-gRNA)−Ct(GAPDH)

The relative expression level of ADg-RNA was estimated by R=2^-ΔCt and displayed on a graph.

EXAMPLE 28

In this example, hADAR2 expression in tet-ADAR2 cells was analyzed by western blotting (FIG. 33). Tet-ADAR2 cells were cultured in media containing doxycycline (Dox) at 0, 0.05, 0.1, 0.5, and 1.5 ug/mL, and subconfluent cells were collected. After counting with a hematocytometer, 6.4×104 cells were lysed with 20 μL SDS-PAGE sample buffer (50 mM Tris-HCl [pH 7.6], 2% SDS, 6% β-mercaptoethanol, 10% glycerol). 5 uL of each cell lysate sample was subjected to SDS-PAGE electrolysis using an 8% polyacrylamide gel to separate proteins and electrophoresed on the PVDF membrane. In order to standardize the amount of lysate loaded, the membrane was cut so that hADAR2 and D-actin could be analyzed simultaneously on the same membrane. Each membrane section was cultured with a primary antibody against hADAR2 (anti-ADARB1, Sigma) and a primary antibody rabbit-derived anti-actin antibody against D-actin, Sigma), followed by addition of horseradish peroxide-conjugated anti-rabbit IgG (Sigma) to react with the secondary antibody. Thereafter, chemiluminescence reaction with EzWestLumi plus (ATTO) was performed, and the band of the protein was detected with LuminoGraph I (ATTO).

EXAMPLE 29

This example shows the editing efficiency induced by AD-gRNA in tet-ADAR2 cells.

EXAMPLE 30

This example shows the editing efficiency of AD-gRNA generated at different sites of the editing substrate RNA. FIG. 35(a) shows the dividing line of the hairpin substrate for generating AD-gRNA. (b) shows the sequence of the target RNA (GFP mRNA) and the sequence of the 5'-antisense ADg-RNA constructed from the framework by dividing at the site shown in (a). ADg (L3) is the same as sADg-rGFP_A200 used in the experiment shown in Example 14. In (c), in order to evaluate the editing-inducing activity of each RNA, the editing assay was performed under the same conditions as shown in Example 16. Changes in editing efficiency at A200 according to reaction time were plotted on a graph. The data represents the average value of the two experiments and the standard deviation value.

INDUSTRIAL APPLICABILITY

The method for introducing a site-directed RNA mutation according to the present invention can easily design and construct any target RNA in which its target base adenosine is present as well as target editing guide RNA for such target RNA. It is thus possible to easily design and construct a double-stranded complex of a target RNA which induces ADAR function and its target editing guide RNA. Thus, in the present invention, by allowing ADAR to act on such a double-stranded complex, it is possible to induce its RNA editing capability and convert the target base adenosine to inosine. Furthermore, since the present invention can be used not only in vitro but also in living bodies, it can be used as a useful and important tool in research and development of drug discovery.

The method for introducing a site-directed RNA mutation according to the present invention can be applied to mutations of amino acids involved in expression of functions of intracellular proteins such as sugar chain modification sites, phosphorylation sites, and metal coordination, and thus can provide a new methodology to temporarily control the function of intracellular proteins. The present invention provides molecular science technology that can greatly contribute to research and development in the life science field by generalizing an in vivo protein function control method by an RNA mutation introduction technique using target editing guide RNA.

Also, nucleic acid preparations have so far been developed, utilizing the suppression of the expression of a target protein by siRNA or the function control of a target protein by functional RNA called aptamer. On the other hand, we have not yet seen examples of drugs that convert mRNA information and modify the function of the target protein. Thus, the present invention provides novel nucleic acid pharmaceuticals exhibiting unprecedented functions and efficacy having possibility to generate drugs for, for example, neurological disorders, such as anti-muscular dystrophy drugs, anti-multiple sclerosis drugs, anti-Alzheimer's drugs, anti-nervous tissue degenerative drugs, and anti-Parkinson's disease, and anticancer drugs.

EXPLANATION OF REFERENCES

10 5'-target side complementary region
12 terminal target complementary region
14 guide side target complementary region
20 antisense region
22 terminal target recognition region
24 Core side target recognition region
26 ADAR binding region
27 guide side divided region
28 ADAR binding core region
50 3'-target complementary region
52 terminal target complementary region
54 guide side target complementary region 60 antisense region
62 terminal target recognition region
64 core side target recognition region 66 ADAR binding region
67 guide side divided region
68 ADAR binding core region

What is claimed is:

1. A method for introducing a site-directed RNA mutation comprising:

reacting a 3'-target RNA represented by formula [XXXVIA]:

[XXXVIA]

3'∼∼ʲN1---ʲNm—A—ᵍN1ᵍN2---ᵍNn—1ᵍNn∼∼5' with a 5'-target editing guide RNA represented by [XXXVIIA], which comprises a base sequence of SEQ ID NO: 99 (GGGUGGAAUA GUAUACCAUU CGUGGUAUAG UAUCCCACCU) between ʲN$_{n+p}$ and ᵏN$_1$:

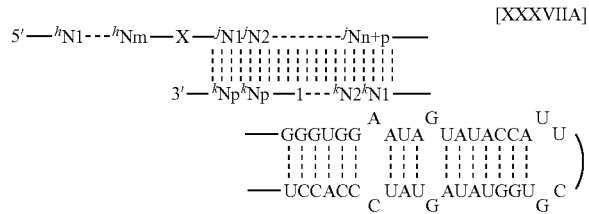

[XXXVIIA]

to obtain a 3'-target RNA-5'-target editing guide RNA complex being represented by formula [XXXVIIIA], which comprises a base sequence of SEQ ID NO: 99 (GGGUGGAAUA GUAUACCAUU CGUG-GUAUAG UAUCCCACCU) between ʲN$_{n+p}$ and ᵏN$_1$:

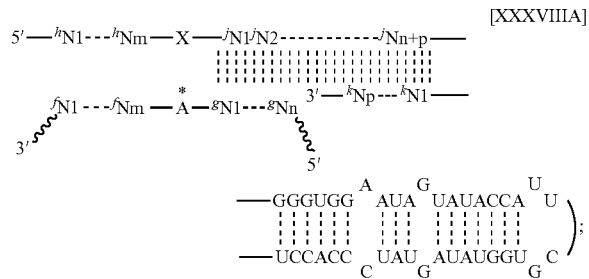

[XXXVIIIA]

obtaining a 3'-edited target RNA represented by formula [XXXIXA]:

[XXXIXA]

3'∼∼ʲN1...ʲNm-I-ᵍN1ᵍN2...ᵍNn-1ᵍNn ∼∼5' in which a target base adenosine (A*) of the resulting 3'-target RNA-5'-target editing guide RNA complex is converted to inosine (I*) by A-I editing by action of double-stranded specific adenosine deaminase (ADAR); wherein, the 3'-target RNA comprises a guide-side target complementary region, a target base adenosine and a terminal-side target complementary region, and in formula [XXXVIA], a symbol of ʲN1 ... ʲNm corresponds to the terminal-side target complementary region of the 3'-target RNA and indicates a base sequence constructed from the same or different bases, and a symbol of ʲN is a base selected from adenine, cytosine, guanine and uracil, and a symbol of m indicates a number of bases of the terminal-side target complementary region in a range of 40 to 20, a symbol of ᵍN1ᵍN2 ... ᵍNn-1ᵍNn corresponds to the guide-side target complementary region of the 3'-target RNA and indicates a base from the same or different bases and a symbol of ᵍN is a base selected from adenine, cytosine, guanine and uracil, and a symbol of n indicates a number of bases of the guide-side target complementary region in a range of 1 to 10, and A* indicates the target base adenine existing at a target editing position; and the 5'-target editing guide RNA comprises a terminal-side target recognition region, a target editing inducing base, a core-side target recognition region, an ADAR binding core region and a guide-side decoupling region, and in formula [XXXVIIA], X is cytosine, guanine or adenine and corresponds to the target editing inducing base, the base sequence of SEO ID NO:99 corresponds to the ADAR binding core region, a symbol of 3'-ᵏN$_p$ᵏN$_{p-1}$ ... ᵏN$_2$ᵏN$_1$ corresponds to the guide-side decoupling region of the 5'-target editing guide RNA and indicates a base sequence constructed from the same or different bases, and a symbol of ᵏN is a base elected from adenine, cytosine, guanine and uracil, and a symbol of p indicates a number of bases of the guide-side decoupling region in a range of 10 or less, a symbol of ʰN1 ... ʰNm corresponds to the terminal-side target recognition region of the 5'-target editing guide RNA and indicates a base sequence constructed from the same or different bases, and a symbol of ʰN is a base selected from adenine, cytosine, guanine and uracil, and a symbol of m indicates the same meaning as described above, and a number of bases in the terminal-side target recognition region is the same number of bases in the base sequence of the terminal-side target complementary region of the 3'-target RNA, and each base in the terminal-side target recognition region forms a base-pair with the corresponding base of the terminal-side target complementary region of the 3'-target RNA, a symbol of ʲN1ʲN2 ... ʲNn+p corresponds to a base sequence of a X adjacent partial region and an ADAR adjacent partial region in the core-side target recognition region of the 5'-target editing guide RNA and indicates a base sequence constructed from the same or different bases, and a symbol of ʲN is a base selected from adenine, cytosine, guanine and uracil, a symbol of n indicates the same meaning as described above and is the same number of bases in a base sequence of the X adjacent partial region of the core-side target recognition region, a symbol of p indicates the same meaning as described above, and is the same number of bases in a base sequence of the ADAR adjacent partial region of the core-side target recognition region, and a base sequence of the X adjacent partial region forms a base-pair with a base sequence of the guide-side target complementary region of the 3'-target RNA, and a base sequence of the guide-side decoupling region forms a base-pair with a base sequence of the ADAR adjacent partial region in the core-side target recognition region as forming the 3'-target RNA-5'-target editing guide RNA complex.

2. The method according to claim 1, wherein n is 3 and p is 0.

3. The method according to claim 1, wherein, the action of ADAR is derived from intravital ADAR mechanism.

* * * * *

```
                              SEQUENCE LISTING

<160> NUMBER OF SEQ ID NOS: 137

<210> SEQ ID NO 1
<211> LENGTH: 48
<212> TYPE: DNA
<213> ORGANISM: Artificial Sequence
<220> FEATURE:
<223> OTHER INFORMATION: guide RNA_D3_tempT7F
<220> FEATURE:
<221> NAME/KEY: misc_feature
<223> OTHER INFORMATION: Synthetic oligo DNA for template DNA to
      synthesize 3'-target editing guide RNA

<400> SEQUENCE: 1
ctaatacgac tcactatagg gtggaatagt ataccattcg tggtatag                    48

<210> SEQ ID NO 2
<211> LENGTH: 44
<212> TYPE: DNA
<213> ORGANISM: Artificial Sequence
<220> FEATURE:
<223> OTHER INFORMATION: guide RNA_D3_tempR
<220> FEATURE:
<221> NAME/KEY: misc_feature
<223> OTHER INFORMATION: Synthetic oligo DNA for template DNA to
      synthesize 3'-target editing guide RNA

<400> SEQUENCE: 2
tgaccaccct gagctgcgga ggtgggatac tataccacga atgg                        44

<210> SEQ ID NO 3
<211> LENGTH: 51
<212> TYPE: DNA
<213> ORGANISM: Artificial Sequence
<220> FEATURE:
<223> OTHER INFORMATION: guide RNA_D0_tempT7F
<220> FEATURE:
<221> NAME/KEY: misc_feature
<223> OTHER INFORMATION: Synthetic oligo DNA for template DNA to
      synthesize 3'-target editing guide RNA

<400> SEQUENCE: 3
ctaatacgac tcactatagg tgggtggaat agtataccat tcgtggtata g                51

<210> SEQ ID NO 4
<211> LENGTH: 44
<212> TYPE: DNA
<213> ORGANISM: Artificial Sequence
<220> FEATURE:
<223> OTHER INFORMATION: guide RNA_D0_tempR
<220> FEATURE:
<221> NAME/KEY: misc_feature
<223> OTHER INFORMATION: Synthetic oligo DNA for template DNA to
      synthesize 3'-target editing guide RNA

<400> SEQUENCE: 4
tgaccaccct gagctgggta ggtgggatac tataccacga atgg                        44

<210> SEQ ID NO 5
<211> LENGTH: 45
<212> TYPE: DNA
<213> ORGANISM: Artificial Sequence
<220> FEATURE:
<223> OTHER INFORMATION: guide RNA_D3r_tempT7F
<220> FEATURE:
```

```
<221> NAME/KEY: misc_feature
<223> OTHER INFORMATION: Synthetic oligo DNA for template DNA to
      synthesize 5'-target editing guide RNA

<400> SEQUENCE: 5
ctaatacgac tcactatagg gaagcactgc acgccgcagc gggtg          45

<210> SEQ ID NO 6
<211> LENGTH: 49
<212> TYPE: DNA
<213> ORGANISM: Artificial Sequence
<220> FEATURE:
<223> OTHER INFORMATION: guide RNA_D3r_tempR
<220> FEATURE:
<221> NAME/KEY: misc_feature
<223> OTHER INFORMATION: Synthetic oligo DNA for template DNA to
      synthesize 5'-target editing guide RNA

<400> SEQUENCE: 6
aggtgggata ctataccacg aatggtatac tattccaccc gctgcggcg      49

<210> SEQ ID NO 7
<211> LENGTH: 45
<212> TYPE: DNA
<213> ORGANISM: Artificial Sequence
<220> FEATURE:
<223> OTHER INFORMATION: guide RNA_D0r_tempT7F
<220> FEATURE:
<221> NAME/KEY: misc_feature
<223> OTHER INFORMATION: Synthetic oligo DNA for template DNA to
      synthesize 5'-target editing guide RNA

<400> SEQUENCE: 7
ctaatacgac tcactatagg gaagcactgc acgccgcggt gggtg          45

<210> SEQ ID NO 8
<211> LENGTH: 52
<212> TYPE: DNA
<213> ORGANISM: Artificial Sequence
<220> FEATURE:
<223> OTHER INFORMATION: guide RNA_D0r_tempR
<220> FEATURE:
<221> NAME/KEY: misc_feature
<223> OTHER INFORMATION: Synthetic oligo DNA for template DNA to
      synthesize 5'-target editing guide RNA

<400> SEQUENCE: 8
ggtaggtggg atactatacc acgaatggta tactattcca cccaccgcgg cg  52

<210> SEQ ID NO 9
<211> LENGTH: 39
<212> TYPE: DNA
<213> ORGANISM: Artificial Sequence
<220> FEATURE:
<223> OTHER INFORMATION: AcGFP_sRNA01_T7F01
<220> FEATURE:
<221> NAME/KEY: misc_feature
<223> OTHER INFORMATION: Forward primer for synthesis of target GFP RNA

<400> SEQUENCE: 9
ctaatacgac tcactatagg gccaccctgg tgaccaccc                 39

<210> SEQ ID NO 10
<211> LENGTH: 20
<212> TYPE: DNA
<213> ORGANISM: Artificial Sequence
<220> FEATURE:
<223> OTHER INFORMATION: AcGFP_sRNA01_R01
<220> FEATURE:
```

```
<221> NAME/KEY: misc_feature
<223> OTHER INFORMATION: Reverse primer for synthesis of target GFP RNA

<400> SEQUENCE: 10
gcgcgcgact tgtagttgcc                                                    20

<210> SEQ ID NO 11
<211> LENGTH: 154
<212> TYPE: RNA
<213> ORGANISM: Artificial Sequence
<220> FEATURE:
<223> OTHER INFORMATION: target RNA
<220> FEATURE:
<221> NAME/KEY: misc_feature
<223> OTHER INFORMATION: Base sequence of a complex of target-editing
      guide RNA with substrate RNA (target RNA)

<400> SEQUENCE: 11 ggguugaaugg ccacaaguuc agcgugagcg gcgagggcga gggcgaugcc accuacggca      60
agcugacccu gaaguucauc ugcaccaccg gcaagcugcc ugugcccugg cccacccugg     120
ugaccacccu gagcuacggc gugcagugcu ucuc                                 154

<210> SEQ ID NO 12
<211> LENGTH: 42
<212> TYPE: DNA
<213> ORGANISM: Artificial Sequence
<220> FEATURE:
<223> OTHER INFORMATION: DNA oligonucleotide for in vitro synthesis of
      ADg-RNA (ADg-GFP_A200_T7F)

<400> SEQUENCE: 12
ctaatacgac tcactatagg gtggaatagt ataacaatat gc                           42

<210> SEQ ID NO 13
<211> LENGTH: 19
<212> TYPE: DNA
<213> ORGANISM: Artificial Sequence
<220> FEATURE:
<223> OTHER INFORMATION: DNA oligonucleotide for in vitro synthesis of
      ADg-RNA (ADg-GFP_A200_RV)

<400> SEQUENCE: 13
tgaccaccct gagctgcgg                                                     19

<210> SEQ ID NO 14
<211> LENGTH: 51
<212> TYPE: DNA
<213> ORGANISM: Artificial Sequence
<220> FEATURE:
<223> OTHER INFORMATION: DNA oligonucleotide for in vitro synthesis of
      ADg-RNA (ADg-rGFP_A200_T7F)

<400> SEQUENCE: 14
ctaatacgac tcactatagg gaagcactgc acgccgcagc gggtggaata g                 51

<210> SEQ ID NO 15
<211> LENGTH: 49
<212> TYPE: DNA
<213> ORGANISM: Artificial Sequence
<220> FEATURE:
<223> OTHER INFORMATION: DNA oligonucleotide for in vitro synthesis of
      ADg-RNA (ADg-rGFP_A200_RV01)

<400> SEQUENCE: 15
aggtgggata ctataacaac atttagcata ttgttatact attccaccc                    49
```

<210> SEQ ID NO 16
<211> LENGTH: 27
<212> TYPE: DNA
<213> ORGANISM: Artificial Sequence
<220> FEATURE:
<223> OTHER INFORMATION: DNA oligonucleotide for in vitro synthesis of
      ADg-RNA (ADg-rGFP_A200_RV02)

<400> SEQUENCE: 16
aggtgggata ctataacaac atttagc                                            27

<210> SEQ ID NO 17
<211> LENGTH: 56
<212> TYPE: DNA
<213> ORGANISM: Artificial Sequence
<220> FEATURE:
<223> OTHER INFORMATION: DNA oligonucleotide for in vitro synthesis of
      ADg-RNA (ADg-rRluc_A311_T7F)

<400> SEQUENCE: 17
ctaatacgac tcactatagg gttcagcagc tcgaaccaag gggtggaata gtatac            56

<210> SEQ ID NO 18
<211> LENGTH: 40
<212> TYPE: DNA
<213> ORGANISM: Artificial Sequence
<220> FEATURE:
<223> OTHER INFORMATION: DNA oligonucleotide for in vitro synthesis of
      ADg-RNA (ADg-rRluc_A311_RV)

<400> SEQUENCE: 18
aggtgggata ctataccacg aatggtatac tattccaccc                              40

<210> SEQ ID NO 19
<211> LENGTH: 48
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-GFP_A200_T7F)

<400> SEQUENCE: 19
ctaatacgac tcactatagg gtggaatagt ataccattcg tggtatag                     48

<210> SEQ ID NO 20
<211> LENGTH: 44
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-GFP_A200_RV)

<400> SEQUENCE: 20
tgaccaccct gagctgcgga ggtgggatac tataccacga atgg                         44

<210> SEQ ID NO 21
<211> LENGTH: 45
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_T7F)

<400> SEQUENCE: 21
ctaatacgac tcactatagg gaagcactgc acgccgcagc gggtg                        45

<210> SEQ ID NO 22
<211> LENGTH: 49
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_RV)

<400> SEQUENCE: 22
aggtgggata ctataccacg aatggtatac tattccaccc gctgcggcg            49

<210> SEQ ID NO 23
<211> LENGTH: 56
<212> TYPE: DNA
<213> ORGANISM: Artificial Sequence
<220> FEATURE:
<223> OTHER INFORMATION: DNA oligonucleotide for in vitro synthesis of
      ADg-RNA (eSL_AAA_Eco_FW)

<400> SEQUENCE: 23
gctaggaatt ccgcctcgag tccgttaaag tgggtggaat agtataccat cgtgg     56

<210> SEQ ID NO 24
<211> LENGTH: 59
<212> TYPE: DNA
<213> ORGANISM: Artificial Sequence
<220> FEATURE:
<223> OTHER INFORMATION: DNA oligonucleotide for in vitro synthesis of
      ADg-RNA (eSL_AAA_Sph_RV)

<400> SEQUENCE: 24
gataagcatg cgccaagctt cgtcagagta ggtgggatac tataccacga atggtatac  59

<210> SEQ ID NO 25
<211> LENGTH: 56
<212> TYPE: DNA
<213> ORGANISM: Artificial Sequence
<220> FEATURE:
<223> OTHER INFORMATION: DNA oligonucleotide for in vitro synthesis of
      ADg-RNA (eSLr_AAA_Eco_FW)

<400> SEQUENCE: 25
gctaggaatt ccgcctcgag tccgtttctg tgggtggaat agtataccat cgtgg     56

<210> SEQ ID NO 26
<211> LENGTH: 59
<212> TYPE: DNA
<213> ORGANISM: Artificial Sequence
<220> FEATURE:
<223> OTHER INFORMATION: DNA oligonucleotide for in vitro synthesis of
      ADg-RNA (eSLr_AAA_Sph_RV)

<400> SEQUENCE: 26
gataagcatg cgccaagctt cgtctttgta ggtgggatac tataccacga atggtatac  59

<210> SEQ ID NO 27
<211> LENGTH: 36
<212> TYPE: DNA
<213> ORGANISM: Artificial Sequence
<220> FEATURE:
<223> OTHER INFORMATION: DNA oligonucleotide for in vitro synthesis of
      ADg-RNA (eSL_AAA_T7F)

<400> SEQUENCE: 27
ctaatacgac tcactatagg gggcgaaagg gggatg                          36

<210> SEQ ID NO 28

```
<211> LENGTH: 16
<212> TYPE: DNA
<213> ORGANISM: Artificial Sequence
<220> FEATURE:
<223> OTHER INFORMATION: DNA oligonucleotide for in vitro synthesis of
      ADg-RNA (eSL_AAA_RV)

<400> SEQUENCE: 28
gcatgcgcca agcttc                                                    16

<210> SEQ ID NO 29
<211> LENGTH: 35
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_AAA_T7F)

<400> SEQUENCE: 29
ctaatacgac tcactatagg gaagcactgc acgcc                               35

<210> SEQ ID NO 30
<211> LENGTH: 60
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_AAA_RV)

<400> SEQUENCE: 30
aggtgggata ctataccacg aatggtatac tattccaccc gcagaggcgt gcagtgcttc    60

<210> SEQ ID NO 31
<211> LENGTH: 45
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_01_T7F)

<400> SEQUENCE: 31
ctaatacgac tcactatagg gaagcactgc acgccgcagt gggtg                    45

<210> SEQ ID NO 32
<211> LENGTH: 51
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_01_RV)

<400> SEQUENCE: 32
gtaggtggga tactatacca cgaatggtat actattccac ccactgcggc g             51

<210> SEQ ID NO 33
<211> LENGTH: 45
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_02_T7F)

<400> SEQUENCE: 33
ctaatacgac tcactatagg gaagcactgc acgccgcagt gggtg                    45

<210> SEQ ID NO 34
<211> LENGTH: 50
```

```
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_02_RV)

<400> SEQUENCE: 34
taggtgggat actataccac gaatggtata ctattccacc cactgcggcg          50

<210> SEQ ID NO 35
<211> LENGTH: 45
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_04_T7F)

<400> SEQUENCE: 35
ctaatacgac tcactatagg gaagcactgc acgccgcagc tggtg               45

<210> SEQ ID NO 36
<211> LENGTH: 48
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_04_RV)

<400> SEQUENCE: 36
ggtgggatac taccacga atggtatact attccaccag ctgcggcg              48

<210> SEQ ID NO 37
<211> LENGTH: 45
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_05_T7F)

<400> SEQUENCE: 37
ctaatacgac tcactatagg gaagcactgc acgccgcagc tcgtg               45

<210> SEQ ID NO 38
<211> LENGTH: 47
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFP_A200_05_RV)

<400> SEQUENCE: 38
gtgggatact ataccacgaa tggtatacta ttccacgagc tgcggcg             47

<210> SEQ ID NO 39
<211> LENGTH: 25
<212> TYPE: DNA
<213> ORGANISM: Artificial Sequence
<220> FEATURE:
<223> OTHER INFORMATION: DNA oligonucleotide for in vitro synthesis of
      ADg-RNA (sADg-rGFPex_AAA_RV)

<400> SEQUENCE: 39
cctgaaggtg ggatactata ccacg                                     25

<210> SEQ ID NO 40
<211> LENGTH: 40
<212> TYPE: DNA
```

<213> ORGANISM: Artificial Sequence
<220> FEATURE:
<223> OTHER INFORMATION: DNA oligonucleotide for in vitro synthesis of
      ADg-RNA (GFPs RNA_T7F)

<400> SEQUENCE: 40
ctaatacgac tcactatagg gtgaatggcc acaagttcag                           40

<210> SEQ ID NO 41
<211> LENGTH: 20
<212> TYPE: DNA
<213> ORGANISM: Artificial Sequence
<220> FEATURE:
<223> OTHER INFORMATION: DNA oligonucleotide for in vitro synthesis of
      ADg-RNA (GFPs RNA_RV)

<400> SEQUENCE: 41
tagcgtgaga agcactgcac                                                20

<210> SEQ ID NO 42
<211> LENGTH: 32
<212> TYPE: DNA
<213> ORGANISM: Artificial Sequence
<220> FEATURE:
<223> OTHER INFORMATION: DNA oligonucleotide for in vitro synthesis of
      ADg-RNA (Rluc W104X_Eco_FW)

<400> SEQUENCE: 42
gctaggaatt caccatggct tccaaggtgt ac                                  32

<210> SEQ ID NO 43
<211> LENGTH: 25
<212> TYPE: DNA
<213> ORGANISM: Artificial Sequence
<220> FEATURE:
<223> OTHER INFORMATION: DNA oligonucleotide for in vitro synthesis of
      ADg-RNA (Rluc W104X_Bam_RV)

<400> SEQUENCE: 43
gaaggatcct tactgctcgt tcttc                                          25

<210> SEQ ID NO 44
<211> LENGTH: 21
<212> TYPE: DNA
<213> ORGANISM: Artificial Sequence
<220> FEATURE:
<223> OTHER INFORMATION: DNA oligonucleotide for in vitro synthesis of
      ADg-RNA (Rluc W104X_FW)

<400> SEQUENCE: 44
ctcaccgctt agttcgagct g                                              21

<210> SEQ ID NO 45
<211> LENGTH: 21
<212> TYPE: DNA
<213> ORGANISM: Artificial Sequence
<220> FEATURE:
<223> OTHER INFORMATION: DNA oligonucleotide for in vitro synthesis of
      ADg-RNA (Rluc W104X_R01)

<400> SEQUENCE: 45
cagctcgaac taagcggtga g                                              21

<210> SEQ ID NO 46
<211> LENGTH: 42
<212> TYPE: DNA
<213> ORGANISM: Artificial Sequence

```
<220> FEATURE:
<223> OTHER INFORMATION: DNA oligonucleotide for in vitro synthesis of
      ADg-RNA (Rluc W104X_Koz_T7F)

<400> SEQUENCE: 46
ctaatacgac tcactatagg gaccatggct tccaaggtgt ac                          42

<210> SEQ ID NO 47
<211> LENGTH: 22
<212> TYPE: DNA
<213> ORGANISM: Artificial Sequence
<220> FEATURE:
<223> OTHER INFORMATION: DNA oligonucleotide for in vitro synthesis of
      ADg-RNA (Rluc W104X_R02)

<400> SEQUENCE: 47
ttactgctcg ttcttcagca cg                                               22

<210> SEQ ID NO 48
<211> LENGTH: 33
<212> TYPE: DNA
<213> ORGANISM: Artificial Sequence
<220> FEATURE:
<223> OTHER INFORMATION: DNA oligonucleotide for in vitro synthesis of
      ADg-RNA (GFPmut_RV)

<400> SEQUENCE: 48
gagaagcact gcacgccttt gctcagggtg gtc                                   33

<210> SEQ ID NO 49
<211> LENGTH: 44
<212> TYPE: DNA
<213> ORGANISM: Artificial Sequence
<220> FEATURE:
<223> OTHER INFORMATION: DNA oligonucleotide for construction of
      expression plasmid (ADg-GFP_A200 F1)

<400> SEQUENCE: 49
gggtggaata gtataacaat atgctaaatg ttgttatagt atcc                       44

<210> SEQ ID NO 50
<211> LENGTH: 39
<212> TYPE: DNA
<213> ORGANISM: Artificial Sequence
<220> FEATURE:
<223> OTHER INFORMATION: DNA oligonucleotide for construction of
      expression plasmid (ADg-GFP_A200 R1)

<400> SEQUENCE: 50
tgaccaccct gagctgcgga ggtgggatac tataacaac                             39

<210> SEQ ID NO 51
<211> LENGTH: 32
<212> TYPE: DNA
<213> ORGANISM: Artificial Sequence
<220> FEATURE:
<223> OTHER INFORMATION: DNA oligonucleotide for construction of
      expression plasmid (ADg-GFP_A200 F2)

<400> SEQUENCE: 51
ctaagatctg ggtggaatag tataacaata tg                                    32

<210> SEQ ID NO 52
<211> LENGTH: 32
<212> TYPE: DNA
<213> ORGANISM: Artificial Sequence
<220> FEATURE:
```

<223> OTHER INFORMATION: DNA oligonucleotide for construction of
      expression plasmid (ADg-GFP_A200 R2)

<400> SEQUENCE: 52
ctaaagctta aaaatgacca ccctgagctg cg                                    32

<210> SEQ ID NO 53
<211> LENGTH: 45
<212> TYPE: DNA
<213> ORGANISM: Artificial Sequence
<220> FEATURE:
<223> OTHER INFORMATION: DNA oligonucleotide for construction of
      expression plasmid (ADg-rGFP_A200 F1)

<400> SEQUENCE: 53
gggaagcact gcacgccgca gcgggtggaa tagtataaca atatg                      45

<210> SEQ ID NO 54
<211> LENGTH: 44
<212> TYPE: DNA
<213> ORGANISM: Artificial Sequence
<220> FEATURE:
<223> OTHER INFORMATION: DNA oligonucleotide for construction of
      expression plasmid (ADg-rGFP_A200 R1)

<400> SEQUENCE: 54
aggtgggata ctataacaac atttagcata ttgttatact attc                       44

<210> SEQ ID NO 55
<211> LENGTH: 27
<212> TYPE: DNA
<213> ORGANISM: Artificial Sequence
<220> FEATURE:
<223> OTHER INFORMATION: DNA oligonucleotide for construction of
      expression plasmid (ADg-rGFP_A200 F2)

<400> SEQUENCE: 55
ctaagatctg ggaagcacug cacgccg                                          27

<210> SEQ ID NO 56
<211> LENGTH: 31
<212> TYPE: DNA
<213> ORGANISM: Artificial Sequence
<220> FEATURE:
<223> OTHER INFORMATION: DNA oligonucleotide for construction of
      expression plasmid (ADg-rGFP_A200 R2)

<400> SEQUENCE: 56
ctaaagctta aaaaggtgg gatactataa c                                      31

<210> SEQ ID NO 57
<211> LENGTH: 35
<212> TYPE: DNA
<213> ORGANISM: Artificial Sequence
<220> FEATURE:
<223> OTHER INFORMATION: DNA oligonucleotide for construction of
      expression plasmid (sADgGFP F)

<400> SEQUENCE: 57
gctagagatc tgggtggaat agtataccat tcgtg                                 35

<210> SEQ ID NO 58
<211> LENGTH: 32
<212> TYPE: DNA
<213> ORGANISM: Artificial Sequence
<220> FEATURE:
<223> OTHER INFORMATION: DNA oligonucleotide for construction of expression plasmid (sADgGFP R)

<400> SEQUENCE: 58
gctagaagct taaaaatgac caccctgagc tg 32

<210> SEQ ID NO 59
<211> LENGTH: 26
<212> TYPE: DNA
<213> ORGANISM: Artificial Sequence
<220> FEATURE:
<223> OTHER INFORMATION: DNA oligonucleotide for construction of
      expression plasmid (sADgrGFP F)

<400> SEQUENCE: 59
gataaagatc tgggaagcac tgcacg 26

<210> SEQ ID NO 60
<211> LENGTH: 36
<212> TYPE: DNA
<213> ORGANISM: Artificial Sequence
<220> FEATURE:
<223> OTHER INFORMATION: DNA oligonucleotide for construction of
      expression plasmid (sADgrGFP R)

<400> SEQUENCE: 60
gctagaagct taaaaaggt gggatactat accacg 36

<210> SEQ ID NO 61
<211> LENGTH: 47
<212> TYPE: DNA
<213> ORGANISM: Artificial Sequence
<220> FEATURE:
<223> OTHER INFORMATION: DNA oligonucleotide for construction of
      expression plasmid (ADg-rGFP_A173 F)

<400> SEQUENCE: 61
gctatagatc tgtcaccagg gtgggccagg gggtggaata gtataac 47

<210> SEQ ID NO 62
<211> LENGTH: 64
<212> TYPE: DNA
<213> ORGANISM: Artificial Sequence
<220> FEATURE:
<223> OTHER INFORMATION: DNA oligonucleotide for construction of
      expression plasmid (ADg-rGFP_A173 R)

<400> SEQUENCE: 62
ccgataagct taaaaggtg ggatactata acaacattta gcatattgtt atactattcc 60
accc 64

<210> SEQ ID NO 63
<211> LENGTH: 26
<212> TYPE: DNA
<213> ORGANISM: Artificial Sequence
<220> FEATURE:
<223> OTHER INFORMATION: DNA oligonucleotide for construction of
      expression plasmid (5'-GFP F)

<400> SEQUENCE: 63
gcatgctcga ggggccgatg gtgagc 26

<210> SEQ ID NO 64
<211> LENGTH: 21
<212> TYPE: DNA
<213> ORGANISM: Artificial Sequence
<220> FEATURE:

```
<223> OTHER INFORMATION: DNA oligonucleotide for construction of
      expression plasmid (5'-GFPW58X R)

<400> SEQUENCE: 64
cagggtgggc tagggcacag g                                              21

<210> SEQ ID NO 65
<211> LENGTH: 21
<212> TYPE: DNA
<213> ORGANISM: Artificial Sequence
<220> FEATURE:
<223> OTHER INFORMATION: DNA oligonucleotide for construction of
      expression plasmid (3'-GFPW58X F)

<400> SEQUENCE: 65
cctgtgccct agcccaccct g                                              21

<210> SEQ ID NO 66
<211> LENGTH: 31
<212> TYPE: DNA
<213> ORGANISM: Artificial Sequence
<220> FEATURE:
<223> OTHER INFORMATION: DNA oligonucleotide for construction of
      expression plasmid (3'-GFP R)

<400> SEQUENCE: 66
ggtacaagct ttcacttgta cagctcatcc a                                   31

<210> SEQ ID NO 67
<211> LENGTH: 37
<212> TYPE: DNA
<213> ORGANISM: Artificial Sequence
<220> FEATURE:
<223> OTHER INFORMATION: DNA oligonucleotide for RT-PCR (oligodT)

<400> SEQUENCE: 67
ggccacgcgt cgactagtac tttttttttt ttttttt                             37

<210> SEQ ID NO 68
<211> LENGTH: 20
<212> TYPE: DNA
<213> ORGANISM: Artificial Sequence
<220> FEATURE:
<223> OTHER INFORMATION: DNA oligonucleotide for RT-PCR (GFP R1 for edit
      check)

<400> SEQUENCE: 68
ggccacgcgt cgactagtac                                                20

<210> SEQ ID NO 69
<211> LENGTH: 20
<212> TYPE: DNA
<213> ORGANISM: Artificial Sequence
<220> FEATURE:
<223> OTHER INFORMATION: DNA oligonucleotide for RT-PCR (GFP R2 for edit
      check)

<400> SEQUENCE: 69
tcacttgtac agctcatcca                                                20

<210> SEQ ID NO 70
<211> LENGTH: 39
<212> TYPE: DNA
<213> ORGANISM: Artificial Sequence
<220> FEATURE:
<223> OTHER INFORMATION: DNA oligonucleotide for RT-PCR (GFP F for edit
      check)
```

```
<400> SEQUENCE: 70
ctaatacgac tcactatagg gatggtgagc aagggcgcc                              39

<210> SEQ ID NO 71
<211> LENGTH: 16
<212> TYPE: DNA
<213> ORGANISM: Artificial Sequence
<220> FEATURE:
<223> OTHER INFORMATION: DNA oligonucleotide for qPCR (sADgrGFP F for
      qPCR)

<400> SEQUENCE: 71
gaagcactgc acgccg                                                       16

<210> SEQ ID NO 72
<211> LENGTH: 19
<212> TYPE: DNA
<213> ORGANISM: Artificial Sequence
<220> FEATURE:
<223> OTHER INFORMATION: DNA oligonucleotide for qPCR (sADgrGFP R for
      qPCR)

<400> SEQUENCE: 72
ggtgggatac tataccacg                                                    19

<210> SEQ ID NO 73
<211> LENGTH: 22
<212> TYPE: DNA
<213> ORGANISM: Artificial Sequence
<220> FEATURE:
<223> OTHER INFORMATION: DNA oligonucleotide for qPCR (GapDH F for qPCR)

<400> SEQUENCE: 73
cctgcaccac caactgctta gc                                                22

<210> SEQ ID NO 74
<211> LENGTH: 24
<212> TYPE: DNA
<213> ORGANISM: Artificial Sequence
<220> FEATURE:
<223> OTHER INFORMATION: DNA oligonucleotide for qPCR (GapDH R for qPCR)

<400> SEQUENCE: 74
gatggcatgg actgtggtca tgac                                              24

<210> SEQ ID NO 75
<211> LENGTH: 68
<212> TYPE: RNA
<213> ORGANISM: Artificial Sequence
<220> FEATURE:
<223> OTHER INFORMATION: sequences of RNA (ADg-GFP_A200 RNA)

<400> SEQUENCE: 75
ggguggaaua guauaacaau augcuaaaug uuguuauagu aucccaccuc cgcagcucag        60
gguggguca                                                               68

<210> SEQ ID NO 76
<211> LENGTH: 19
<212> TYPE: RNA
<213> ORGANISM: Artificial Sequence
<220> FEATURE:
<223> OTHER INFORMATION: sequences of RNA (3'-antisense RNA)

<400> SEQUENCE: 76
```
ccgcagcuca gggugguca                                              19

<210> SEQ ID NO 77
<211> LENGTH: 22
<212> TYPE: RNA
<213> ORGANISM: Artificial Sequence
<220> FEATURE:
<223> OTHER INFORMATION: sequences of RNA (5'-antisense RNA)

<400> SEQUENCE: 77
gggaagcacu gcacgccgca gc                                          22

<210> SEQ ID NO 78
<211> LENGTH: 71
<212> TYPE: RNA
<213> ORGANISM: Artificial Sequence
<220> FEATURE:
<223> OTHER INFORMATION: sequences of RNA (ADg-rGFP_A200 RNA)

<400> SEQUENCE: 78
gggaagcacu gcacgccgca gcggguggaa uaguauaaca auaugcuaaa uguuguuaua    60
guaucccacc u                                                      71

<210> SEQ ID NO 79
<211> LENGTH: 62
<212> TYPE: RNA
<213> ORGANISM: Artificial Sequence
<220> FEATURE:
<223> OTHER INFORMATION: sequences of RNA (AD-guide rRluc_A311 RNA)

<400> SEQUENCE: 79
ggguucagca gcucgaacca aggggugqaa uaguauacca uucgugguau aguaucccac    60
cu                                                                62

<210> SEQ ID NO 80
<211> LENGTH: 59
<212> TYPE: RNA
<213> ORGANISM: Artificial Sequence
<220> FEATURE:
<223> OTHER INFORMATION: sequences of RNA (sADg-GFP_A200 RNA)

<400> SEQUENCE: 80
ggguggaaua guauaccauu cgugguauag uaucccaccu ccgcagcuca gggugguca     59

<210> SEQ ID NO 81
<211> LENGTH: 62
<212> TYPE: RNA
<213> ORGANISM: Artificial Sequence
<220> FEATURE:
<223> OTHER INFORMATION: sequences of RNA (sADg-rGFP_A200 RNA)

<400> SEQUENCE: 81
gggaagcacu gcacgccgca gcggguggaa uaguauacca uucgugguau aguaucccac    60
cu                                                                62

<210> SEQ ID NO 82
<211> LENGTH: 62
<212> TYPE: RNA
<213> ORGANISM: Artificial Sequence
<220> FEATURE:
<223> OTHER INFORMATION: sequences of RNA (sADg-rGFP_AAA)

<400> SEQUENCE: 82
gggaagcacu gcacgccucu gcggguggaa uaguauacca uucgugguau aguaucccac    60
cu                                                                    62

<210> SEQ ID NO 83
<211> LENGTH: 67
<212> TYPE: RNA
<213> ORGANISM: Artificial Sequence
<220> FEATURE:
<223> OTHER INFORMATION: sequences of RNA (sADg-rGFPex_AAA)

<400> SEQUENCE: 83
gggaagcacu gcacgccucu gcggguggaa uaguauacca uucgugguau aguaucccac     60
cuucagg                                                               67

<210> SEQ ID NO 84
<211> LENGTH: 65
<212> TYPE: RNA
<213> ORGANISM: Artificial Sequence
<220> FEATURE:
<223> OTHER INFORMATION: sequences of RNA (sADg-rGFP_A200_0)

<400> SEQUENCE: 84
gggaagcacu gcacgccgcg guggguggaa uaguauacca uucgugguau aguaucccac     60
cuacc                                                                 65

<210> SEQ ID NO 85
<211> LENGTH: 64
<212> TYPE: RNA
<213> ORGANISM: Artificial Sequence
<220> FEATURE:
<223> OTHER INFORMATION: sequences of RNA (ADg (L1))

<400> SEQUENCE: 85
gggaagcacu gcacgccgca guggguggaa uaguauacca uucgugguau aguaucccac     60
cuac                                                                  64

<210> SEQ ID NO 86
<211> LENGTH: 63
<212> TYPE: RNA
<213> ORGANISM: Artificial Sequence
<220> FEATURE:
<223> OTHER INFORMATION: sequences of RNA (ADg (L2))

<400> SEQUENCE: 86
gggaagcacu gcacgccgca gugggguggaa uaguauacca uucgugguau aguaucccac    60
cua                                                                   63

<210> SEQ ID NO 87
<211> LENGTH: 61
<212> TYPE: RNA
<213> ORGANISM: Artificial Sequence
<220> FEATURE:
<223> OTHER INFORMATION: sequences of RNA (ADg (L4))

<400> SEQUENCE: 87
gggaagcacu gcacgccgca gcugguggaa uaguauacca uucgugguau aguaucccac     60
c                                                                     61

<210> SEQ ID NO 88
<211> LENGTH: 60
<212> TYPE: RNA
<213> ORGANISM: Artificial Sequence
<220> FEATURE:

<223> OTHER INFORMATION: sequences of RNA (ADg (L5))

<400> SEQUENCE: 88
gggaagcacu gcacgccgca gcucguggaa uaguauacca uucgugguau aguaucccac    60

<210> SEQ ID NO 89
<211> LENGTH: 69
<212> TYPE: RNA
<213> ORGANISM: Artificial Sequence
<220> FEATURE:
<223> OTHER INFORMATION: sequences of RNA (ADg-rGFP_A173)

<400> SEQUENCE: 89
gucaccaggg ugggccaggg gguggaauag uauaacaaua ugcuaaaugu uguuauagua    60
ucccaccuu    69

<210> SEQ ID NO 90
<211> LENGTH: 61
<212> TYPE: RNA
<213> ORGANISM: Artificial Sequence
<220> FEATURE:
<223> OTHER INFORMATION: sequences of RNA (sADgGFP)

<400> SEQUENCE: 90
ggguggaaua guauaccauu cgugguauag uauccaccu ccgcagcuca gggugucau    60 u    61

<210> SEQ ID NO 91
<211> LENGTH: 64
<212> TYPE: RNA
<213> ORGANISM: Artificial Sequence
<220> FEATURE:
<223> OTHER INFORMATION: sequences of RNA (sADgrGFP)

<400> SEQUENCE: 91
gggaagcacu gcacgccgca gcggguggaa uaguauacca uucgugguau aguaucccac    60
cuuu    64

<210> SEQ ID NO 92
<211> LENGTH: 720
<212> TYPE: RNA
<213> ORGANISM: Unknown
<220> FEATURE:
<223> OTHER INFORMATION: sequences of RNA (GFP RNA)

<400> SEQUENCE: 92
auggugagca agggcgccga gcuguucacc ggcaucgugc ccauccugau cgagcugaau    60
ggcgauguga auggccacaa guucagcgug agcggcgagg gcgagggcga ugccaccuac    120
ggcaagcuga cccugaaguu caucugcacc accggcaagc ugccugugcc cuggcccacc    180
cuggugacca cccugagcua cggcgugcag ugcuucucac gcuacccga ucacaugaag    240 cagcacgacu ucuucaagag cgccaugccu gagggcuaca uccaggagcg caccaucuuc    300
uucgaggaug acggcaacua caagucgcgc gccgagguga aguucgaggg cgauacccug    360
gugaaucgca ucgagcugac cggcaccgau uucaaggagg augcaacau ccugggcaau    420 aagauggagu acaacuacaa cgcccacaau guguacauca ugaccgacaa ggccaagaau    480
ggcaucaagg ugaacuucaa gauccgccac aacaucgagg auggcagcgu gcagcuggcc    540
gaccacuacc agcagaauac ccccaucggc gauggcccug ugcugcugcc cgauaaccac    600
uaccugucca cccagagcgc ccuguccaag gaccccaacg agaagcgcga ucacaugauc    660

```
uacuucggcu ucgugaccgc cgccgccauc acccacggca uggaugagcu guacaaguga    720
```

<210> SEQ ID NO 93
<211> LENGTH: 160
<212> TYPE: RNA
<213> ORGANISM: Unknown
<220> FEATURE:
<223> OTHER INFORMATION: sequences of RNA (GFPs RNA)

<400> SEQUENCE: 93

```
ggguagaaugg ccacaaguuc agcgugagcg gcgagggcga gggcgaugcc accuacggca    60
agcugacccu gaaguucauc ugcaccaccg gcaagcugcc ugugcccugg cccacccugg    120
ugaccacccu gagcuacggc gugcagugcu ucucacgcua                          160
```

<210> SEQ ID NO 94
<211> LENGTH: 942
<212> TYPE: RNA
<213> ORGANISM: Unknown
<220> FEATURE:
<223> OTHER INFORMATION: sequences of RNA (Rluc W104X RNA)

<400> SEQUENCE: 94

```
gggaccaugg cuuccaaggu guacgacccc gagcaacgca aacgcaugau cacugggccu    60
cagugguggg cucgcugcaa gcaaaugaac gugcuggacu ccuucaucaa cuacuaugau    120
uccgagaagc acgccgagaa cgccgugauu uuucugcaug guaacgcugc cuccagcuac    180
cuguggaggc acgucgugcc ucacaucgag cccguggcua gaugcaucau cccugaucug    240 aucggaauugg guaaguccgg caagagcggg aauggcucau aucgccuccu ggaucacuac    300
aaguaccuca ccgcuuaguu cgagcugcug aaccuuccaa agaaaaucau cuuugugggc    360
cacgacuggg gggcuugucu ggccuuucac uacuccuacg agcaccaaga caagaucaag    420
gccaucgucc augcugagag ugucguggac gugaucgagu ccuggacgga gugggccugac   480 aucgaggagg auaucgcccu gaucaagagc gaagagggcg agaaaauggu gcuugagaau    540
aacuucuucg ucgagaccau gcucccaagc aagaucaugc ggaaacugga gccgaggag     600 uucgcugccu accuggagcc auucaaggag aagggcgagg uuagacggcc uacccucucc    660 uggcccucgcg agauccucu cguuaaggga ggcaagcccg acgucgucca gauugccgc    720 aacuacaacg ccuaccuucg ggccagcgac gaucugccua agauguucau cgagucccgac   780 ccuggguucu uuccaacgc uauugucgag ggagcuaaga aguucccuaa caccgaguuc     840
gugaagguga agggccucca cuucagccag gaggacgcuc cagaugaaau ggguaaguac     900
aucaagagcu ucguggagcg cgugcugaag aacgagcagu aa                      942
```

<210> SEQ ID NO 95
<211> LENGTH: 178
<212> TYPE: RNA
<213> ORGANISM: Artificial Sequence
<220> FEATURE:
<223> OTHER INFORMATION: sequences of RNA (eSL_AAA RNA)

<400> SEQUENCE: 95

```
gggggcgaaa ggggaugug cugcaaggcg auuaaguugg guaacgccag gguuuuccca    60
gucacgacgu uguaaaacga cggccaguga auuccgccuc gaguccguua agugggugg    120 aauaguauac cauucguggu auaguauccc accuacucug acgaagcuug gcgcaugc    178
```

<210> SEQ ID NO 96

```
<211> LENGTH: 178
<212> TYPE: RNA
<213> ORGANISM: Artificial Sequence
<220> FEATURE:
<223> OTHER INFORMATION: sequences of RNA (eSLr_AAA RNA)

<400> SEQUENCE: 96
gggggcgaaa gggggaugug cugcaaggcg auuaaguugg guaacgccag gguuuuccca      60
gucacgacgu uguaaaacga cggccaguga auuccgccuc gaguccguuu cuguggguogg     120 aauaguauac cauucguggu auaguauccc accuacaaag acgaagcuug gcgcaugc       178

<210> SEQ ID NO 97
<211> LENGTH: 154
<212> TYPE: RNA
<213> ORGANISM: Artificial Sequence
<220> FEATURE:
<223> OTHER INFORMATION: sequences of RNA (GFPmut RNA)

<400> SEQUENCE: 97 ggguguaaugg ccacaaguuc agcgugagcg gcgagggcga ggcgaugcc accuacggca      60 agcugacccu gaaguucauc ugcaccaccg gcaagcugcc ugugcccugg cccacccugg     120
ugaccacccu gagcaaaggc gugcagugcu ucuc                                 154

<210> SEQ ID NO 98
<211> LENGTH: 720
<212> TYPE: RNA
<213> ORGANISM: Artificial Sequence
<220> FEATURE:
<223> OTHER INFORMATION: sequences of RNA (AcGFP W58X RNA)

<400> SEQUENCE: 98
auggugagca agggcgccga gcuguucacc ggcaucgugc ccauccugau cgagcugaau      60
ggcgauguga auggccacaa guucagcgug agcggcgagg gcgagggcga ugccaccuac     120
ggcaagcuga cccugaaguu caucugcacc accggcaagc ugccugugcc cuagcccacc     180
cuggugacca cccugagcua cggcgugcag ugcuucucac gcuaccccga ucacaugaag     240
cagcacgacu ucuucaagag cgccaugccu gagggcuaca uccaggagcg caccaucuuc     300
uucgaggaug acggcaacua caagucgcgc gccgagguga aguucgaggg cgauacccug     360
gugaaucgca ucgagcugac cggcaccgau uucaaggagg augcaacau ccugggcaau      420 aagauggagu acaacuacaa cgcccacaau guguacauca ugaccgacaa ggccaagaau     480
ggcaucaagg ugaacuucaa gauccgccac aacaucgagg auggcagcgu gcagcuggcc     540
gaccacuacc agcagaauac ccccaucggc gauggcccug ugcugcugcc cgauaaccac     600
uaccugucca cccagagcgc ccuguccaag gaccccaacg agaagcgcga ucacaugauc     660
uacuucggcu ucgugaccgc cgccgccauc acccacggca uggaugagcu guacaaguga     720

<210> SEQ ID NO 99
<211> LENGTH: 40
<212> TYPE: RNA
<213> ORGANISM: Artificial Sequence
<220> FEATURE:
<223> OTHER INFORMATION: ADAR binding core region

<400> SEQUENCE: 99
ggguggaaua guauaccauu cgugguauag uaucccaccu                            40

<210> SEQ ID NO 100
<211> LENGTH: 67
```

<212> TYPE: RNA
<213> ORGANISM: Artificial Sequence
<220> FEATURE:
<223> OTHER INFORMATION: GluR-B pre-mRNA

<400> SEQUENCE: 100
cauuaaggug gguggaauag uauaacaaua ugcucaaugu uguuauagua ucccaccuac    60
ccagacg                                                             67

<210> SEQ ID NO 101
<211> LENGTH: 58
<212> TYPE: RNA
<213> ORGANISM: Artificial Sequence
<220> FEATURE:
<223> OTHER INFORMATION: miniSL

<400> SEQUENCE: 101
cauuaaggug gguggaauag uauaccauuc gugguauagu aucccaccua cccagacg     58

<210> SEQ ID NO 102
<211> LENGTH: 49
<212> TYPE: RNA
<213> ORGANISM: Artificial Sequence
<220> FEATURE:
<223> OTHER INFORMATION: XLV-2

<400> SEQUENCE: 102
ggguggaaua guauaccauu cgugguauag uaucccaccu acccagacg               49

<210> SEQ ID NO 103
<211> LENGTH: 58
<212> TYPE: RNA
<213> ORGANISM: Artificial Sequence
<220> FEATURE:
<223> OTHER INFORMATION: XLA-2

<400> SEQUENCE: 103
cguuuaggug gguggaauag uauaccauuc gugguauagu aucccaccua cccagacg     58

<210> SEQ ID NO 104
<211> LENGTH: 58
<212> TYPE: RNA
<213> ORGANISM: Artificial Sequence
<220> FEATURE:
<223> OTHER INFORMATION: XLA

<400> SEQUENCE: 104
cguuuaggug gguggaauag uauaccauuc gugguauagu aucccaccua cccagacg     58

<210> SEQ ID NO 105
<211> LENGTH: 58
<212> TYPE: RNA
<213> ORGANISM: Artificial Sequence
<220> FEATURE:
<223> OTHER INFORMATION: XLIA

<400> SEQUENCE: 105
cguuucggug gguggaauag uauaccauuc gugguauagu aucccaccua ccaagacg     58

<210> SEQ ID NO 106
<211> LENGTH: 52
<212> TYPE: RNA
<213> ORGANISM: Artificial Sequence
<220> FEATURE:
<223> OTHER INFORMATION: XLVA-0

```
<400> SEQUENCE: 106
cguuucggug gguggaauag uauaccauuc gugguauagu aucccaccua cc        52

<210> SEQ ID NO 107
<211> LENGTH: 51
<212> TYPE: RNA
<213> ORGANISM: Artificial Sequence
<220> FEATURE:
<223> OTHER INFORMATION: XLVA-1

<400> SEQUENCE: 107
cguuucggug gguggaauag uauaccauuc gugguauagu aucccaccua c         51

<210> SEQ ID NO 108
<211> LENGTH: 50
<212> TYPE: RNA
<213> ORGANISM: Artificial Sequence
<220> FEATURE:
<223> OTHER INFORMATION: XLVA-2

<400> SEQUENCE: 108
cguuucggug gguggaauag uauaccauuc gugguauagu aucccaccua           50

<210> SEQ ID NO 109
<211> LENGTH: 49
<212> TYPE: RNA
<213> ORGANISM: Artificial Sequence
<220> FEATURE:
<223> OTHER INFORMATION: XLVA-3

<400> SEQUENCE: 109
cguuucggug gguggaauag uauaccauuc gugguauagu aucccaccu            49

<210> SEQ ID NO 110
<211> LENGTH: 48
<212> TYPE: RNA
<213> ORGANISM: Artificial Sequence
<220> FEATURE:
<223> OTHER INFORMATION: XLVA-4

<400> SEQUENCE: 110
cguuucggug gguggaauag uauaccauuc gugguauagu aucccacc             48

<210> SEQ ID NO 111
<211> LENGTH: 47
<212> TYPE: RNA
<213> ORGANISM: Artificial Sequence
<220> FEATURE:
<223> OTHER INFORMATION: XLVA-5

<400> SEQUENCE: 111
cguuucggug gguggaauag uauaccauuc gugguauagu aucccac              47

<210> SEQ ID NO 112
<211> LENGTH: 11
<212> TYPE: RNA
<213> ORGANISM: Artificial Sequence
<220> FEATURE:
<223> OTHER INFORMATION: XLVIA

<400> SEQUENCE: 112
cuaccaagac g                                                     11

<210> SEQ ID NO 113
<211> LENGTH: 10
```

```
<212> TYPE: RNA
<213> ORGANISM: Artificial Sequence
<220> FEATURE:
<223> OTHER INFORMATION: XLVIA-4

<400> SEQUENCE: 113
uaccaagacg                                                          10

<210> SEQ ID NO 114
<211> LENGTH: 19
<212> TYPE: RNA
<213> ORGANISM: Artificial Sequence
<220> FEATURE:
<223> OTHER INFORMATION: XLIII-1

<400> SEQUENCE: 114
gcuacggcgu gcagugcuu                                                19

<210> SEQ ID NO 115
<211> LENGTH: 59
<212> TYPE: RNA
<213> ORGANISM: Artificial Sequence
<220> FEATURE:
<223> OTHER INFORMATION: XLIII-2

<400> SEQUENCE: 115
aagcacugca cgccgcagcg gguggaauag uauaccauuc gggguauagu aucccaccu     59

<210> SEQ ID NO 116
<211> LENGTH: 19
<212> TYPE: RNA
<213> ORGANISM: Artificial Sequence
<220> FEATURE:
<223> OTHER INFORMATION: XLIII-4
<220> FEATURE:
<221> NAME/KEY: misc_feature
<222> LOCATION: (4)..(4)
<223> OTHER INFORMATION: i

<400> SEQUENCE: 116
gcuacggcgu gcagugcuu                                                19

<210> SEQ ID NO 117
<211> LENGTH: 19
<212> TYPE: RNA
<213> ORGANISM: Artificial Sequence
<220> FEATURE:
<223> OTHER INFORMATION: XLIII-5

<400> SEQUENCE: 117
gcugcggcgu gcagugcuu                                                19

<210> SEQ ID NO 118
<211> LENGTH: 67
<212> TYPE: RNA
<213> ORGANISM: Artificial Sequence
<220> FEATURE:
<223> OTHER INFORMATION: GluR2 pre-mRNA

<400> SEQUENCE: 118
cauuaaggug ggguggaauag uauaacaaua ugcuaaaugu guuuauagua ucccaccuac   60
ccugaug                                                             67

<210> SEQ ID NO 119
<211> LENGTH: 49
<212> TYPE: RNA
```

```
<213> ORGANISM: Artificial Sequence
<220> FEATURE:
<223> OTHER INFORMATION: ADg-RNA fig.21b

<400> SEQUENCE: 119 ggguggaauua guauaacaau augcuaaaug uuguuauagu aucccaccu          49

<210> SEQ ID NO 120
<211> LENGTH: 31
<212> TYPE: RNA
<213> ORGANISM: Artificial Sequence
<220> FEATURE:
<223> OTHER INFORMATION: GFP mRNA

<400> SEQUENCE: 120
ugaccacccu gagcuacggc gugcagugcu u                              31

<210> SEQ ID NO 121
<211> LENGTH: 68
<212> TYPE: RNA
<213> ORGANISM: Artificial Sequence
<220> FEATURE:
<223> OTHER INFORMATION: ADg rGFP A200

<400> SEQUENCE: 121
aaguacugca cgccgcagcg gguggaauag uauaacaaua ugcuaaaugu uguuauagua    60
ucccaccu                                                            68

<210> SEQ ID NO 122
<211> LENGTH: 68
<212> TYPE: RNA
<213> ORGANISM: Artificial Sequence
<220> FEATURE:
<223> OTHER INFORMATION: ADg-GFP A200

<400> SEQUENCE: 122 ggguggaauua guauaacaau augcuaaaug uuguuauagu aucccaccua gccccgucag   60
gguggguca                                                           68

<210> SEQ ID NO 123
<211> LENGTH: 58
<212> TYPE: RNA
<213> ORGANISM: Artificial Sequence
<220> FEATURE:
<223> OTHER INFORMATION: hairpin substrate fig24

<400> SEQUENCE: 123
cauuaaggug gguggaauag uauaccauuc gugguauagu aucccaccua cccugaug      58

<210> SEQ ID NO 124
<211> LENGTH: 59
<212> TYPE: RNA
<213> ORGANISM: Artificial Sequence
<220> FEATURE:
<223> OTHER INFORMATION: sADg-GFP_A200

<400> SEQUENCE: 124 ggguggaauua guauaccauu cgugguauag uaucccaccu agccccguca ggguguca     59

<210> SEQ ID NO 125
<211> LENGTH: 59
<212> TYPE: RNA
<213> ORGANISM: Artificial Sequence
<220> FEATURE:
<223> OTHER INFORMATION: sADg-rGFP_A200
```

<400> SEQUENCE: 125
aaguacugca cgccgcagcg gguggaauag uauaccauuc gugguauagu aucccaccu      59

<210> SEQ ID NO 126
<211> LENGTH: 58
<212> TYPE: RNA
<213> ORGANISM: Artificial Sequence
<220> FEATURE:
<223> OTHER INFORMATION: eSL_AAA

<400> SEQUENCE: 126
cauuaaagug gguggaauag uauaccauuc gugguauagu aucccaccua cucugaug       58

<210> SEQ ID NO 127
<211> LENGTH: 58
<212> TYPE: RNA
<213> ORGANISM: Artificial Sequence
<220> FEATURE:
<223> OTHER INFORMATION: eSLr_AAA

<400> SEQUENCE: 127
cauuucugug gguggaauag uauaccauuc gugguauagu aucccaccua caaagaug       58

<210> SEQ ID NO 128
<211> LENGTH: 31
<212> TYPE: RNA
<213> ORGANISM: Artificial Sequence
<220> FEATURE:
<223> OTHER INFORMATION: GFPmut RNA part

<400> SEQUENCE: 128
ugaccacccu gagcaaaggc gugcagugcu u                                    31

<210> SEQ ID NO 129
<211> LENGTH: 59
<212> TYPE: RNA
<213> ORGANISM: Artificial Sequence
<220> FEATURE:
<223> OTHER INFORMATION: sADg-rGFP_AAA2

<400> SEQUENCE: 129
aaguacugca cgccucugcu ccacccuaug auauggugcu uaccauauga uaagguggg      59

<210> SEQ ID NO 130
<211> LENGTH: 59
<212> TYPE: RNA
<213> ORGANISM: Artificial Sequence
<220> FEATURE:
<223> OTHER INFORMATION: sADg-rGFPex_AAA2

<400> SEQUENCE: 130
aaguacugca cgccucugcu ccacccuaug auauggugcu uaccauauga uaagguggg      59

<210> SEQ ID NO 131
<211> LENGTH: 33
<212> TYPE: RNA
<213> ORGANISM: Artificial Sequence
<220> FEATURE:
<223> OTHER INFORMATION: Rluc W58X part

<400> SEQUENCE: 131
aguaccucac cgcuuaguuc gagcugcuga acc                                  33

<210> SEQ ID NO 132

```
<211> LENGTH: 61
<212> TYPE: RNA
<213> ORGANISM: Artificial Sequence
<220> FEATURE:
<223> OTHER INFORMATION: ADg-rRluc_A311

<400> SEQUENCE: 132
gguucagcag cucgaaccaa gggguggaau aguauaccau ucgugguaua guaucccacc      60
u                                                                    61

<210> SEQ ID NO 133
<211> LENGTH: 59
<212> TYPE: RNA
<213> ORGANISM: Artificial Sequence
<220> FEATURE:
<223> OTHER INFORMATION: ADg(L3)

<400> SEQUENCE: 133
aaguacugca cgccgcagcg gguggaauag uauaccauuc gugguauagu aucccaccu       59

<210> SEQ ID NO 134
<211> LENGTH: 61
<212> TYPE: RNA
<213> ORGANISM: Artificial Sequence
<220> FEATURE:
<223> OTHER INFORMATION: ADg(L1) fig35

<400> SEQUENCE: 134
aaguacugca cgccgcagug gguggaauag uauaccauuc gugguauagu aucccaccua      60
c                                                                    61

<210> SEQ ID NO 135
<211> LENGTH: 60
<212> TYPE: RNA
<213> ORGANISM: Artificial Sequence
<220> FEATURE:
<223> OTHER INFORMATION: ADg(L2) fig35

<400> SEQUENCE: 135
aaguacugca cgccgcagug gguggaauag uauaccauuc gugguauagu aucccaccua      60

<210> SEQ ID NO 136
<211> LENGTH: 58
<212> TYPE: RNA
<213> ORGANISM: Artificial Sequence
<220> FEATURE:
<223> OTHER INFORMATION: ADg(L4) fig35

<400> SEQUENCE: 136
aaguacugca cgccgcagug gguggaauag uauaccauuc gugguauagu aucccacc        58

<210> SEQ ID NO 137
<211> LENGTH: 57
<212> TYPE: RNA
<213> ORGANISM: Artificial Sequence
<220> FEATURE:
<223> OTHER INFORMATION: ADg(L5) fig35

<400> SEQUENCE: 137
aaguacugca cgccgcagug gguggaauag uauaccauuc gugguauagu aucccac         57
```